US011129850B2

(12) United States Patent
Klingemann et al.

(10) Patent No.: US 11,129,850 B2
(45) Date of Patent: Sep. 28, 2021

(54) QUADRICISTRONIC SYSTEM COMPRISING A HOMING RECEPTOR AND CHIMERIC ANTIGEN RECEPTOR FOR STABLE GENETIC MODIFICATION OF CELLULAR IMMUNOTHERAPIES

(71) Applicant: NANTKWEST, INC., San Diego, CA (US)

(72) Inventors: Hans G. Klingemann, San Diego, CA (US); Laurent H. Boissel, San Diego, CA (US); Nathan T. Schomer, San Diego, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

(21) Appl. No.: 16/707,807

(22) Filed: Dec. 9, 2019

(65) Prior Publication Data

US 2020/0101111 A1 Apr. 2, 2020

Related U.S. Application Data

(62) Division of application No. 16/529,029, filed on Aug. 1, 2019.

(60) Provisional application No. 62/713,264, filed on Aug. 1, 2018, provisional application No. 62/713,278, filed on Aug. 1, 2018, provisional application No. 62/713,310, filed on Aug. 1, 2018, provisional application No. 62/713,323, filed on Aug. 1, 2018.

(51) Int. Cl.
| | |
|---|---|
| *A61K 35/17* | (2015.01) |
| *A61P 35/00* | (2006.01) |
| *C12N 15/62* | (2006.01) |
| *A61P 35/02* | (2006.01) |
| *C12N 15/85* | (2006.01) |
| *C07K 14/705* | (2006.01) |
| *A61K 9/00* | (2006.01) |
| *C07K 14/82* | (2006.01) |
| *C07K 14/55* | (2006.01) |
| *C07K 14/725* | (2006.01) |
| *C07K 14/54* | (2006.01) |

(52) U.S. Cl.
CPC ............ *A61K 35/17* (2013.01); *A61K 9/0029* (2013.01); *A61P 35/02* (2018.01); *C07K 14/5443* (2013.01); *C07K 14/55* (2013.01); *C07K 14/7051* (2013.01); *C07K 14/70553* (2013.01); *C07K 14/70564* (2013.01); *C07K 14/70596* (2013.01); *C07K 14/82* (2013.01); *C12N 15/625* (2013.01); *C12N 15/85* (2013.01)

(58) Field of Classification Search
None
See application file for complete search history.

(56) References Cited

U.S. PATENT DOCUMENTS

| | | | |
|---|---|---|---|
| 6,034,072 A | 3/2000 | Ralston et al. | |
| 7,098,008 B2 | 8/2006 | Park et al. | |
| 7,618,817 B2 | 11/2009 | Campbell | |
| 8,034,332 B2 * | 10/2011 | Klingemann | ........ C12N 5/0093 |
| | | | 424/93.21 |
| 8,313,943 B2 | 11/2012 | Campbell | |
| 8,987,417 B2 | 3/2015 | Zwaagstra et al. | |
| 9,061,059 B2 * | 6/2015 | Chakraborty | .......... C07K 16/40 |
| 9,150,636 B2 | 10/2015 | Campbell | |
| 9,181,322 B2 | 11/2015 | Campbell | |
| 9,266,938 B2 | 2/2016 | Ast et al. | |
| 10,138,462 B2 * | 11/2018 | Klingemann | ........ C12N 5/0093 |
| 10,456,420 B2 | 10/2019 | Lee et al. | |
| 10,960,024 B2 | 3/2021 | Klingemann et al. | |
| 2002/0068044 A1 | 6/2002 | Klingemann | |
| 2003/0105292 A1 | 6/2003 | Liaw et al. | |
| 2003/0167531 A1 | 9/2003 | Russell et al. | |
| 2004/0052770 A1 * | 3/2004 | Klingemann | ........ C12N 5/0646 |
| | | | 424/93.7 |

(Continued)

FOREIGN PATENT DOCUMENTS

| | | |
|---|---|---|
| WO | 98/49268 A1 | 11/1998 |
| WO | 99/024566 A1 | 5/1999 |

(Continued)

OTHER PUBLICATIONS

Clark et al., Inferring nonneutral evolution from human-chimp-mouse orthologous gene trios 2003; Science 302 (5652), 1960-1963.*

(Continued)

*Primary Examiner* — Maria G Leavitt

(74) *Attorney, Agent, or Firm* — Martin Fessenmaier; Umberg Zipser LLP

(57) ABSTRACT

Provided herein are modified NK-92® cells comprising one or more nucleic acids encoding i) a homing receptor, ii) Antigen Binding Protein (ABP) or Chimeric Antigen Receptor (CAR) that specifically binds to a target antigen, iii) an Fc Receptor such as CD16 or CD16-158V, and/or iv) a cytokine, wherein the nucleic acid sequence is operably linked to a promoter. Further provided herein are modified NK-92® cells comprising one or more nucleic acids encoding i) IL-12 and/or TGF-beta trap, ii) an Antigen Binding Protein (ABP) or Chimeric Antigen Receptor (CAR) that specifically binds to a target antigen, iii) an Fc Receptor such as CD16 or CD16-158V, and/or iv) a cytokine, wherein the nucleic acid sequence is operably linked to a promoter. Also provided are compositions and kits comprising the modified NK-92® cells, as well as methods of treating cancer using the modified cells.

4 Claims, 34 Drawing Sheets

Specification includes a Sequence Listing.

(56) References Cited

U.S. PATENT DOCUMENTS

| | | |
|---|---|---|
| 2008/0247990 A1 | 10/2008 | Campbell |
| 2013/0040386 A1 | 2/2013 | Campbell |
| 2013/0189268 A1 | 7/2013 | Du et al. |
| 2013/0280285 A1 | 10/2013 | Schonfeld et al. |
| 2014/0099714 A1 | 4/2014 | Klingemann |
| 2014/0242701 A1 | 8/2014 | Shiku et al. |
| 2014/0274909 A1 | 9/2014 | Orentas et al. |
| 2014/0322183 A1 | 10/2014 | Milone et al. |
| 2018/0044424 A1 | 2/2018 | June et al. |
| 2018/0057795 A1 | 3/2018 | Childs et al. |
| 2018/0155439 A1 | 6/2018 | Galipeau et al. |
| 2018/0163176 A1* | 6/2018 | Lee .................... A61K 39/00 |
| 2018/0187149 A1 | 7/2018 | Ma et al. |
| 2018/0207295 A1 | 7/2018 | Fotin-Mleczek et al. |
| 2018/0258397 A1* | 9/2018 | Klingemann .... C07K 14/70535 |
| 2020/0023010 A1 | 1/2020 | Dilillo et al. |
| 2020/0038441 A1 | 2/2020 | Klingemann et al. |
| 2020/0093863 A1 | 3/2020 | Klingemann et al. |

FOREIGN PATENT DOCUMENTS

| | | |
|---|---|---|
| WO | 00/20460 A1 | 4/2000 |
| WO | 03/008583 A2 | 1/2003 |
| WO | 03/035837 A2 | 5/2003 |
| WO | WO2003084570 * | 10/2003 |
| WO | 03/101485 A1 | 12/2003 |
| WO | 2008/157367 A1 | 12/2008 |
| WO | 2014/039523 A1 | 3/2014 |
| WO | 2014/099671 A1 | 6/2014 |
| WO | 2016/176639 A1 | 11/2016 |
| WO | WO2016201304 * | 12/2016 |
| WO | 2017/123548 A1 | 7/2017 |
| WO | 2017/214569 A1 | 12/2017 |
| WO | 2018/076391 A1 | 5/2018 |
| WO | 2019/089813 A1 | 5/2019 |
| WO | 2019/152513 A1 | 8/2019 |
| WO | 2019/226521 A1 | 11/2019 |
| WO | 2019/226708 A1 | 11/2019 |
| WO | 2020/010110 A1 | 1/2020 |
| WO | 2020/028656 A1 | 2/2020 |

OTHER PUBLICATIONS

Engineering lymph node homing of ex vivo-expanded human natural killer cells via trogocytosis of the chemokine receptor CCR7 Blood (2012) 119 (22): 5164-5172.*

Denman et al Membrane-Bound IL-21 Promotes Sustained Ex Vivo Proliferation of Human Natural Killer Cells PLoS ONE Jan. 2012 | vol. 7 | Issue 1 | e30264 pp. 1-12.*

NK-92® ATCC® CRL-2407™ *Homo sapiens* peripheral blood pp. 1-3 downloaded May 28, 2020.*

NK-92® MI ATCC® CRL-2408™ *Homo sapiens* peripheral bloo pp. 1-3 downloaded May 28, 2020.*

NK-92® ATCC® CRL-2407™ b *Homo sapiens* peripheral blood mpp 1-3 downloaded May 28, 2020.*

Seminars in Immunology, vol. 13, 2001: pp. 267-274 Dendritic cell migration to lymph nodes: cytokines, chemokines, and lipid mediators.*

ATCC Genetically modiied natural killer cell line retroviral transduced to express CD-16 (PTA-8836), pp. 1-2; downloaded Nov. 3, 2020.*

ATCC Genetically modiied natural killer cell lines pp. 1-5, downloaded Nov. 3, 2020.*

Ngo, in The Protein Folding Problem and Tertiary Structure Prediction, Merz et al. (eds.), Birkhauser Boston: Boston, MA 1994; pp. 433-495.*

Rudinger (in Peptide Hormones, Parsons (ed.), University Park Press: Baltimore, MD, pp. 1-7-, 1976.*

Abate-Daga et al., "CAR models: next-generation CAR modifications for enhanced T-cell function", Oncolytics (2016) pp. 1-7.

ATCC N K-92 product , Credible leads to incredible; pp. 1-6; downloaded Dec. 5, 2019.

Konstantinidis et al., "Targeting IL-2 to the endoplasmic reticulum confines autocrine growth stimulation to NK-92 cells" Experimental Hematology 33 (2005) 159-164.

International Search Report and Written opinion received for PCT Application Serial No. PCT/US19/44655, dated Dec. 4, 2019, 17 pages.

GenBank MH107787, "Mammalian expression vector pEXPR50, complete sequence", Apr. 11, 2018, https://www.ncbi.nlm nih.gov/nuccore/MH107787.1/, 3 pages.

Non-Final Office Action received for U.S. Appl. No. 16/529,029 dated Dec. 11, 2019, 26 pages.

Swarts et al., "Tumor Microenvironment Complexity: Emerging Roles in Cancer Therapy", Cancer Research, Mar. 13, 2012, vol. 72, pp. 2473-2480 (Cited Form Specification).

Herberman et al., "Natural Killer Cells: Their Role in Defenses Against Disease", Science, Oct. 2, 1981, vol. 214, pp. 24-30 (Cited Form Specification).

Smith et al., "Comparison of Biosequences", Advances in applied mathematics 2, 1981, pp. 482-489 (Cited Form Specification).

Needleman et al., "A General Method Applicable to the Search for Similarities in the Amino Acid Sequence of Two Proteins", J. Mol. Biol., 1970, vol. 48, pp. 443-453 (Cited Form Specification).

Pearson et al., "Improved tools for biological sequence comparison", Biochemistry, Proc. Natl. Acad. Sci. USA, Apr. 1988, vol. 85, pp. 2444-2448 (Cited Form Specification).

Altschul et al., "Gapped Blast and PSI-BLAST: A new generation of protein database search programs", Nucleic Acids Research, 1997, vol. 25, No. 17, pp. 3389-3402 (Cited Form Specification).

Altschul et al., "Basic Local Alignment Tool", J. Mol. Biol., 1990, vol. 215, pp. 403-410 (Cited Form Specification).

Henikoff et al., "Amino acid substitution matrices from protein blocks", Biochemistry, Proc. Natl. Acad. Sci. USA, Nov. 1992, vol. 89, p. 10915-10919 (Cited Form Specification).

Gong et al., "Characterization of a human cell line (NK-92) with phenotypical and functional characteristics of activated natural killer cells", Leukemia, Apr. 1994, vol. 8, No. 4, pp. 652-658 (Cited Form Specification).

Maki et al., "Factors Regulating the Cytotoxic Activity of the Human Natural Killer Cell Line, NK-92", Journal of hematotherapy & Stem Cell Research, 2001, vol. 10, pp. 369-383 (Cited Form Specification).

Suck et al., "NK 92: an 'off the shelf therapeutic' for adoptive natural killer cell based cancer immunotherapy", Cancer Immunol Immunotherapy, Nov. 11, 2015, vol. 65, No. 4, pp. 485-492 (Cited Form Specification).

Klingemann et al., "Purging of malignant cells from blood after short ex vivo incubation with NK-92 cells", Blood, 1996, vol. 87, No. 11, pp. 4913-4914 (Cited Form Specification).

Yan et al., "Antileukemia activity of a natural killer cell line against human leukaemia's", Clinical Cancer Research, Nov. 1998, vol. 4, No. 11, pp. 2859-2868 (Cited Form Specification).

Swift et al., "Natural killer cell lines preferentially kill clonogenic multiple myeloma cells and decrease myeloma engraftment in a bioluminescent xenograft mouse model", Haematologica, Cell Therapy and Immunotherapy, 2012, vol. 97, No. 7, pp. 1020-1028 (Cited Form Specification).

Tam et al., "Immunotherapy of Malignant Melanoma in a SCID Mouse Model Using the Highly Cytotoxic Natural Killer Cell Line NK-92", Journal of Hematotherapy, 1999, vol. 8, pp. 281-290 (Cited Form Specification).

Konstantinidis et al., "Targeting IL-2 to the endoplasmic reticulum confines autocrine growth stimulation to NK-92 cells", Experimental Hematology, 2005, vol. 33. No. 2, pp. 159-164 (Cited Form Specification).

Zwaagstra et al., "Engineering and Therapeutic Application of Single-Chain Bivalent TGF-β Family Traps", Mol. Canc. THer. 2012, vol. 11(7), pp. 1477-1487 (Cited Form Specification).

Batzer et al., "Enhanced evolutionary PCR using oligonucleotides with inosine at the 3'-terminus", Nucleic Acids Research, 1991, vol. 19, No. 18, 1 page (Cited Form Specification).

Ohtsuka et al., "An Alternative Approach to Deoxyoligonucleotides as Hybridization Probes by Insertion of Deoxyinosine at Ambiguous

(56) References Cited

OTHER PUBLICATIONS

Codon Positions", The Journal of Biological Chemistry, Mar. 10, 1985, vol. 260, No. 5, pp. 2605-2608 (Cited Form Specification).
Rossolini et al., Use of deoxyinosine-containing primers vs Degenerate primers for polymerase chain reaction based on Ambiguous sequence information, Molecular and Cellular Probes, 1994, vol. 8, pp. 91-98 (Cited Form Specification).
Yazawa K, Fisher W E, Brunicardi F C: Current Progress in Suicide gene therapy for cancer. World J. Surg. Jul. 2002; 26(7): 783-9.
Wang et al., "Augmented anti-tumor activity of NK-92 cells expressing chimeric receptors of TGF-betaR II and NKG2D", Cancer Immunol Immunother, 2017, vol. 66, No. 4, 12 pages.
Yang et al., "Blocking transforming growth factor-beta signaling pathway augments antitumor effect of adoptive NK-92 cell therapy", International Immunopharmacology, 2013, vol. 17, pp. 198-204.
Non Final Office Action received for U.S. Appl. No. 16/529,029 dated Jun. 8, 2020, 32 pages.
Final Office Action received for U.S. Appl. No. 16/708,082 dated Jun. 5, 2020, 24 pages.
Non Final Office Action received for U.S. Appl. No. 16/775,111 dated Aug. 7, 2020, 32 pages.
International Preliminary Report on Patentability Chapter II received for PCT Application Serial No. PCT/US2019/044655, dated Jul. 24, 2020, 14 pages.
Final Office Action received for U.S. Appl. No. 16/775,111 dated Jan. 11, 2021, 59 pages.
Notice of Allowance received for U.S. Appl. No. 16/529,029 dated Jan. 13, 2021, 16 pages.
International Search Report and Written opinion received for PCT Application Serial No. PCT/US2020/015487 dated Oct. 27, 2020, 11 pages.
Final Office Action received for U.S. Appl. No. 16/529,029 dated Nov. 6, 2020, 36 pages.
Non-Final Office Action received for U.S. Appl. No. 16/708,082 dated Nov. 16, 2020, 405 pages.
Jochems et al., "An NK cell line (haN K) expressing high levels of granzyme and engineered to express the high affinity CD16 allele", Oncotarget 2016;7:86359-86373.
Non Final Office Action received for U.S. Appl. No. 16/775,111 dated Jun. 15, 2021, 34 pages.
Final Office Action received for U.S. Appl. No. 16/708,082 dated Mar. 16, 2021, 44 pages.
Rudikoff et al., "Single amino acid substitution altering antigen-binding specificity" Proc. Natl Acad. Sci., 1982, vol. 79, pp. 1979-1983.
Coleman et al., "Effects of amino acid sequence changes on antibody-antigen interactions", Research in Immunology, 1994, vol. 145, pp. 33-36.
Almagro et al., "Humanization of antibodies", Frontiers in Bioscience, 2008, vol. 13, No. 5, pp. 1619-1633.

Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue", The Journal of Cell Biology,1990, vol. 111, pp. 2129-2138.
Notice of Allowance received for U.S. Appl. No. 16/708,082 dated May 21, 2021, 18 pages.
Notice of Allowance received for U.S. Appl. No. 16/529,029 dated Feb. 9, 2021, 7 pages.
Final Office Action recieved for U.S. Appl. No. 16/529,029 dated Feb. 20, 2020, 21 pages.
Non-Final Office Action recieved for U.S. Appl. No. 16/708,082 dated Feb. 18, 2020, 16 pages.
Hayes et al., "Redirecting Mouse CTL Against Colon Carcinoma: Superior Signaling Efficacy of Single-Chain Variable Domain Chimeras Containing TCR-$\int$ vs FcVRI-$\gamma$", The Journal of Immunology, 2001, vol. 166, No. 1, pp. 182-187 (Specification of U.S. Appl. No. 16/775,111, p. No. 3, Line 3).
Cartellieri et al., "Chimeric antigen receptor-engineered T cells for immunotherapy of cancer", Journal of Biomedicine and Biotechnology, vol. 10, pp. 1-13 (Specification of U.S. Appl. No. 16/775,111, p. No. 3, Line 4).
Bollino et al., "Chimeric antigen receptor-engineered natural killer and natural killer T cells for cancer immunotherapy", Transl. Res., Sep. 2017, vol. 187, 21 pages (Specification of U.S. Appl. No. 16/775,111, p. No. 4, Line 6).
Bruhns et al., "Specificity and addinity of human Fcgamma receptors and their polymorphic variants for human IgG subclasses", Blood, vol. 113, No. 16, pp. 3716-3725 (Specification of U.S. Appl. No. 16/775,111, p. No. 13, Line 20).
Garcia-Sanchez et al. "Cytosine deaminase adenoviral vector and 5-fluorocytosine selectively reduce breast caner cells 1 million-fold when they contaminate hematopoietic cells: a potential purging method for autologous transplantation", Blood, vol. 92, No. 2, 1998, pp. 672-682 (Specification of U.S. Appl. No. 16/775,111, p. No. 19, Line 8).
Touati et al., "A suicide gene therapy combining the improvement of cyclophosphamide tumor cytotoxicity and the development of an anti-tumor immune response", Current Gene Therapy, 2014, vol. 14, pp. 236-246 (Specification of U.S. Appl. No. 16/775,111, p. No. 19, lines 11-12).
Di Stasi et al., "Inducible apoptosis as a safety switch for adoptive cell therapy", N Engl J Med., Nov. 3, 2011, vol. 365, No. 18, pp. 1673-1683 (Specification of U.S. Appl. No. 16/775,111, p. No. 19, lines 12-14).
Morgan Richard A, "Live and Let Die: A New Suicide Gene Therapy Moves to the Clinic", Molecular therapy, Jan. 2012, vol. 20, No. 1, pp. 11-13 (Specification of U.S. Appl. No. 16/775,111, No. 19, lines 14-15).

\* cited by examiner

QUADRICISTRONIC SYSTEM COMPRISING A HOMING RECEPTOR AND CHIMERIC ANTIGEN RECEPTOR FOR STABLE GENETIC MODIFICATION OF CELLULAR IMMUNOTHERAPIES

The present application is a divisional of U.S. patent application Ser. No. 16/529,029 filed Aug. 1, 2019, which claims the benefit of priority to U.S. provisional applications with the Ser. No. 62/713,264, filed Aug. 1, 2018; 62/713,278, filed Aug. 1, 2018, 62/713,310 filed Aug. 1, 2018; and 62/713,323 filed on Aug. 1, 2018. Each of these applications is incorporated by reference herein in its entirety.

SEQUENCE LISTING

The content of the ASCII text file of the sequence listing named 104077_0007PCT_Seq_listing_rev004_ST25, which is 97 KB in size was created on Aug. 1, 2019 and electronically submitted via EFS-Web along with the present application, and is incorporated by reference in its entirety.

FIELD OF THE INVENTION

The field of the invention is engineered cells using the cytotoxic activated Natural Killer cell line (NK-92) as the basis to improve immunotherapies to cancer and tumors.

BACKGROUND

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer immunotherapies based on adoptively transferred tumor-specific cytotoxic lymphocytes hold promise for the treatment of patients with tumor malignancies. Despite this early success in certain cancers, the treatment of tumors remains a challenge, mostly due to the immunosuppressive nature of the tumor microenvironment. See Swarts et al. "Tumor Microenvironment Complexity: Emerging Roles in Cancer Therapy," Cancer Res, vol., 72, pages 2473-2480, 2012. In addition to modified T-cells, immunotherapies based on NK cells are being explored. Natural killer (NK) cells are cytotoxic lymphocytes that constitute a major component of the innate immune system. Natural killer (NK) cells, generally representing about 10-15% of circulating lymphocytes, bind and kill targeted cells, including virus-infected cells and many malignant cells, non-specifically with regard to antigen and without prior immune sensitization. Herberman et al., Science 214:24 (1981). NK-92® is a cytolytic cancer cell line which was discovered in the blood of a subject suffering from a non-Hodgkin's lymphoma and then immortalized ex vivo. NK-92® cells are derived from NK cells, but lack the major inhibitory receptors that are displayed by normal NK cells, while retaining the majority of the activating receptors. NK-92® cells do not, however, attack normal cells nor do they elicit an unacceptable immune rejection response in humans.

A common driver of lymph node metastasis is the hypoxia-driven upregulation of CCR7, a chemokine receptor primarily found in naïve T-cells and dendritic cells. Upregulation of the CCR7 receptor on blood NK cells has previously been demonstrated to improve the homing of NK cells to lymph nodes, allowing them to follow the same path to the lymph node compartments that are common pathways of metastatic spread, but has not yet been demonstrated in a clinically relevant cell line.

Therefore, there is still a need to imprive NK cells and NK cell based therapies, especially in the context of NK cell homing to and modulation of a tumor microenvironment.

BRIEF SUMMARY

Provided herein are modified NK-92® cells comprising a nucleic acid encoding multiple function elements. The functional elements are typically proteins or polypeptides that provide a specific function that improves the effectiveness of the cells as a cell line for immunotherapy. In one aspect, the NK-92® cells comprise a nucleic acid construct encoding four functional elements. In some embodiments, the nucleic acid construct comprises sequences encoding four functional elements operably linked to a promoter (referred to as a "Quadricistronic Construct").

In some embodiments, the first element encoded by the nucleic acid construct is a cytokine that provides selection for NK-92® cells that express the cytokine, such as IL-2 or IL-15. Thus, in some embodiments, the nucleic acid encodes a cytokine such as IL-2 or IL-15. In one embodiment, the IL-2 is expressed with a signal sequence that directs the IL-2 to the endoplasmic reticulum IL-2 ("erIL-2"). In another embodiment, the IL-15 is expressed with a signal sequence that directs the IL-15 to the endoplasmic reticulum IL-15 ("erIL-15").

In some embodiments, the second element encoded by the nucleic acid construct is an Fc receptor. In some embodiments, the Fc receptor is an Fc-gamma receptor (FCγR). In some embodiments, the Fc-gamma receptor is FCγRIII-A (also called CD16), which is a low affinity Fc receptor that binds to IgG antibodies and activates ADCC. In some embodiments, the CD16 receptor comprises a phenylalanine (F) to valine (V) substitution at amino acid position 158 (F158V) of the mature form of the polypeptide (SEQ ID NO: 12) (corresponding to position 176 of the full length form of the polypeptide comprising the signal sequence). In one embodiment, the Fc receptor comprises the nucleic acid sequence of SEQ ID NO:13 or the amino acid sequence of SEQ ID NO:12.

In some embodiments, the first and second elements are present in the nucleic acid construct. Thus, in some embodiments, the nucleic acid construct encodes an Fc receptor (such as CD16) and erIL-2.

In some embodiments, the third element encoded by the nucleic acid construct is a homing receptor. In some embodiments, the homing receptor is a cytokine receptor, a G protein-coupled receptor, a chemokine receptor, a cell adhesion molecule, a selectin, or an integrin. In some embodiments, the homing receptor is operably linked to a promoter that allows transcription of the nucleic acid. The modified NK-92® cells are capable of migrating toward a source of the chemokine that is the ligand for the receptor. Unlike normal blood-derived NK cells, the modified NK-92® cells can be developed into cell lines that are relevant for human clinical trials, which provides a distinct advantage for immunotherapy. Examples of homing receptors include G protein-coupled receptors such as chemokine receptors, including but not limited to CCR1, CCR2, CCR3, CCR4, CCR5, CCR6, CCR7, CCR8, CCR9, CCR10, CXCR1, CXCR2, CXCR3, CXCR4, CXCR5, CXCR6, CXCR7, CX3CR1, XCR1, CCXCKR, D6, DARC, or the receptor for CXCL14; cytokine receptors; cell adhesion molecules such as selectins, including L-selectin (CD62L); integrins such as α4β7 integrin, LPAM-1, and LFA-1. In some embodiments, the homing receptor is a cell adhesion molecule such as LFA-1. In some embodiments, the homing receptor is a selectin, such as L-selectin (CD62L). In some embodiments, the homing receptor is an integrin such as α4β7 integrin, LPAM-1, or VLA-4. In some embodiments, the homing receptor is a C-C or C-X-C chemokine receptor. Thus, in some embodiments, third element encoded by the nucleic acid is a homing receptor described herein.

In some embodiments, the third element encoded by the nucleic acid construct is a secreted cytokine, whereby the cytokine increases or improves the function of the NK-92® cells as immunotherapeutic agents. The cytokine may also modulate the tumor microenvironment. In some embodiments, the secreted cytokine that modulates the tumor microenvironment is IL-12 or IFN-alpha. Thus, in some embodiments, the third element encoded by the nucleic acid construct is a cytokine such as IL-12 or IFN-alpha.

Thus, in some embodiments, the third element encoded by the nucleic acid construct is a chemokine such as XCL1, CCL5, CCL21 or CCL16. In some embodiments, the third element encoded by the nucleic acid construct is a Toll-like Receptor (TLR) agonist.

In one aspect, the third element encoded by the nucleic acid construct is IL-12.

TGF-β expression within tumors is known to suppress the antitumor activity of leukocytes in the tumor microenvironment. Thus, in some embodiments, the third element encoded by the nucleic acid construct is a TGF-beta inhibitor, for example a peptide that inhibits TGF-β. In some embodiments, the third element encoded by the nucleic acid construct is a TGF-beta trap. In some embodiments, the TGF-beta trap comprises the extracellular domain of a TGFβRII molecule. In some embodiments, the TGF-beta trap comprises a single chain dimer of the extracellular domain of a TGFβRII molecule, and most preferably comprises a single chain dimer of the TGF-beta Receptor II ectodomain.

In some embodiments, the NK cells described herein are administered with a TGF-β inhibitor to block TGF-β and help remove immunosuppression. In some embodiments, the NK cells described herein are administered with other immunotherapies to help decrease or eliminate a tumor. For example, TGF-β can be inhibited by intratumoral injection of inhibitory peptides in combination with intratumoral injections of poly(I:C) and an α-CD40 antibody. In some embodiments, the TGF-β inhibitor is combined with IL-2.

In some embodiments, the fourth element encoded by the nucleic acid construct is an antigen binding protein ("ABP"). In some embodiments, the antigen binding protein specifically binds a tumor associated antigen. In some embodiments, the ABP comprises a fragment of an antibody, such as an scFv. In some embodiments, the antigen binding protein comprises or is part of a chimeric antigen receptor (CAR). In some embodiments, the nucleic acid encodes an ABP or CAR that specifically binds CD19, CD20, NKG2D ligands, CS1, GD2, CD138, EpCAM, HER-2, EBNA3C, GPA7, CD244, CA-125, MUC-1, ETA, MAGE, CEA, CD52, CD30, MUCSAC, c-Met, EGFR, FAP, WT-1, PSMA, NY-ESO1, CSPG-4, IGF1-R, Flt-3, CD276, CD123, PD-L1, BCMA, CD33, B7-H4, or 41BB.

In another aspect, the modified NK-92® cells comprise a nucleic acid encoding IL-12. In another aspect, the modified NK-92® cells comprise a nucleic acid encoding a TGF-beta trap. In some embodiments, the TGF-beta trap comprises a single chain dimer of the extracellular domain of a TGFβRII molecule.

In another aspect, the modified NK-92® cells comprise a nucleic acid encoding a cytokine that provides selection or allows survival of NK-92® cells that express the cytokine. In some embodiments, the nucleic acid encodes a cytokine such as IL-2 or IL-15. In one embodiment, the IL-2 is expressed with a signal sequence that directs the IL-2 to the endoplasmic reticulum IL-2 ("erIL-2"). In one embodiment, the IL-15 is expressed with a signal sequence that directs the IL-15 to the endoplasmic reticulum IL-2 ("erIL-15").

In some embodiments, the modified NK-92® cells comprise a nucleic acid encoding an Fc receptor. In some embodiments, the Fc receptor is an Fc-gamma receptor (FCγR). In some embodiments, the Fc-gamma receptor is FCγRIII-A (also called CD16), which is a low affinity Fc receptor that binds to IgG antibodies and activates ADCC. In some embodiments, the CD16 receptor comprises a phenylalanine (F) to valine (V) substitution at amino acid position 158 (F158V) of the mature form of the polypeptide (SEQ ID NO:12) (corresponding to position 176 of the full length form of the polypeptide comprising the signal sequence). In one embodiment, the Fc receptor comprises the nucleic acid sequence of SEQ ID NO:13 or the amino acid sequence of SEQ ID NO:12.

In some embodiments, the modified NK-92® cells comprise a nucleic acid encoding an antigen binding protein ("ABP"). In some embodiments, the antigen binding protein specifically binds a tumor associated antigen. In some embodiments, the ABP comprises a fragment of an antibody, such as an scFv. In some embodiments, the antigen binding protein comprises or is part of a chimeric antigen receptor (CAR). In some embodiments, the nucleic acid encodes an ABP or CAR that specifically binds CD19, CD20, NKG2D ligands, CS1, GD2, CD138, EpCAM, HER-2, EBNA3C, GPA7, CD244, CA-125, MUC-1, ETA, MAGE, CEA, CD52, CD30, MUCSAC, c-Met, EGFR, FAP, WT-1, PSMA, NY-ESO1, CSPG-4, IGF1-R, Flt-3, CD276, CD123, PD-L1, BCMA, CD33, B7-H4, or 41BB.

In another aspect, the modified NK-92® cells comprise a nucleic acid encoding a secreted cytokine that modulates the tumor microenvironment. In some embodiments, the cytokine that modulates the tumor microenvironment is a chemokine such as XCL1, CCL5, CCL21 or CCL16. In some embodiments, the modified NK-92® cells comprise a nucleic acid encoding a Toll-like Receptor (TLR) agonist. In some embodiments, the modified NK-92® cells comprise a nucleic acid encoding a IL-12 or IFN-alpha. In some embodiments, the modified NK-92® cells comprise a nucleic acid encoding a TGF-beta inhibitor, for example a peptide that inhibits TGF-β. In some embodiments, the modified NK-92® cells comprise a nucleic acid encoding a TGF-beta trap. In some embodiments, the TGF-beta trap comprises the extracellular domain of a TGFβRII molecule, or a single chan dimer of the extracellular domain of a TGFβRII molecule.

In one aspect, the modified NK-92® cells comprise one or more, or a plurality, of nucleic acid molecules encoding a homing receptor, an ABP or CAR, an Fc receptor, and/or a cytokine that provides selection or allows survival of NK-92® cells that express the cytokine. Thus, in some embodiments, the modified NK-92® cells comprise nucleic acid molecules encoding a chemokine receptor, a CAR, CD16, and erIL-2. In some embodiments, the modified NK-92® cells comprise nucleic acid molecules encoding CCR7 or CXCR2, a CAR, CD16, and erIL-2. In some embodiments, the modified NK-92® cells comprise nucleic acid molecules encoding IL-12 or a TGF-beta trap, a CAR, CD16, and erIL-2.

In some embodiments, the CAR comprises an intracellular signaling domain from the Fc epsilon receptor gamma (FcεRIγ). In one embodiment, the CAR is transiently expressed by the NK-92® cell. In one embodiment, the CAR is stably expressed by the NK-92® cell.

To date, FcεRIγ-containing CARs have not been utilized in NK-92® cells, other NK cell lines, or endogenous NK cells because other signaling domains (e.g., CD3ζ) were determined to be more efficient, especially when combined with additional signaling domains (second and third generation CARs). Described herein is the unexpected and surprising finding that NK-92® cells expressing a "first-generation" CAR comprising an intracellular domain from FcεRIγ have equal or higher cytotoxic activity against cancer cells expressing the antigen recognized by the CAR than NK-92® cells expressing CARs with a CD3ζ signaling domain alone or in combination with other signaling domains (i.e., second or third generation CARs). In one embodiment, the CD3t signaling domain contemplated herein may comprise a polypeptide sequence having at least 80%, 85%, 90%, 91%, 92%, 93%, 94%, 95%, 96%, 97%, 98% or 99% identity to SEQ ID NO: 40.

In one aspect, an NK-92® cell or cell line expressing a chimeric antigen receptor (CAR) on the surface of the NK-92® cell is described, wherein said CAR comprises a cytoplasmic domain of FcεRIγ. In one embodiment, the cytoplasmic domain of FcεRIγ comprises an amino acid sequence having at least 95% sequence identity to SEQ ID NO: 31.

In some embodiments, the cytoplasmic domain of FcεRIγ is encoded by a nucleic acid having at least 95% sequence identity to SEQ ID NO:32.

In some embodiments, the CAR comprises a hinge region from CD8. In some embodiments, the CAR comprises a transmembrane domain from CD28.

In some embodiments, the NK-92® cell or cell line is genetically modified with a nucleic acid construct that comprises SEQ ID NO:31 (FcεRIγ intracellular cytoplasmic domain), SEQ ID NO:32 (FcεRIγ intracellular signaling domain minus transmembrance domain), SEQ ID NO: 33 (CD8 hinge region), SEQ ID NO: 34 (CD8 hinge region DNA), SEQ ID NO:35 (CD28 transmembrane domain) and/or SEQ ID NO:36 (CD28 transmembrane domain, minus ITAM or intracellular sequence). In one embodiment, the CD8 hinge region, CD28 transmembrane, and FceRI-gamma signaling domain amino acid sequence comprises a polypeptide or a polynucleotide sequence having at least 80%, 85%, 90%, 91%, 92%, 93%, 94%, 95%, 96%, 97%, 98% or 99% identity to SEQ ID NO: 37 or SEQ ID NO: 38. In some embodiments, the nucleic acid construct further comprises a promoter that promotes transcription of the nucleic acid sequences. In some embodiments, the promoter is an inducible promoter. In some embodiments, the nucleic acid construct is a multi-cistronic vector comprising one or more Internal Ribosome Entry Site (IRES) to allow for initiation of translation from an internal region of an mRNA transcribed from the nucleic acid sequences. In some embodiments, the nucleic acid construct comprises a sequence that encodes a 2A peptide, such as a T2A, P2A, E2A, or F2A peptide, in order to produce equimolar levels of polypeptides encoded by the same mRNA. In some embodiments, the nucleic acid construct further comprises a nucleic acid sequence that encodes an antigen binding protein (ABP). In some embodiments, the ABP is an scFv or a codon optimized scFv. In some embodiments, the ABP specifically binds an antigen expressed by a tumor cell. In some embodiments, the ABP is part of a chimeric antigen receptor (CAR). In some embodiments, the construct comprises a nuclei acid that encodes a cytokine, that provides selection or allows survival of NK-92® cells that express the cytokine, such a IL-2. In one embodiment, the cytokine is targeted to the endoplasmic reticulum. In one embodiment, the CAR scFv may comprise a polypeptide sequence having at least 80%, 85%, 90%, 91%, 92%, 93%, 94%, 95%, 96%, 97%, 98% or 99% identity to SEQ ID NO: 39.

In some embodiments, the construct comprises the vector shown in FIG. 10. In some embodiments, the NK-92® cell or cell line is genetically modified to express CD16 on the cell surface. In one embodiment, the NK-92® cell or cell line is genetically modified to express a high affinity CD16 (F158V) on the cell surface.

In one embodiment, the ABP or CAR targets or specifically binds a tumor-associated antigen. In one embodiment, the tumor-associated antigen is selected from the group consisting of CD19, CD20, NKG2D ligands, CS1, GD2, CD138, EpCAM, HER-2, EBNA3C, GPA7, CD244, CA-125, MUC-1, ETA, MAGE, CEA, CD52, CD30, MUC5AC, c-Met, EGFR, FAP, WT-1, PSMA, NY-ESO1, CSPG-4, IGF1-R, Flt-3, CD276, CD123, PD-L1, BCMA, CD33 B7-H4, and 41BB. In one embodiment, the tumor-associated antigen is CD19. In another embodiment, the tumor-associated antigen is CD33.

In one aspect, the present disclosure relates to a NK-92® cell line that is transformed by a nucleic acid encoding a chimeric antigen receptor (CAR) with a cytoplasmic domain of FcεRIγ, wherein the CAR is expressed on the surface of the NK-92® cell. In one embodiment, the nucleic acid is RNA. In one embodiment, the nucleic acid is DNA.

In some embodiments, the NK-92® cell is further modified to express at least one cytokine or variant thereof that provides selection or allows survival of NK-92® cells that express the cytokine. In one embodiment, the at least one cytokine is transiently expressed by the NK-92® cell. In one embodiment, the at least one cytokine is stably expressed by the NK-92® cell.

In some embodiments, the modified NK-92® cells comprise an expression vector comprising one or more, or a plurality, of the nucleic acid molecules described herein. In some embodiments, the nucleic acid molecule is operably linked to a promoter that is capable of initiating transcription of the nucleic acid molecule. In some embodiments, each nucleic acid molecule of the plurality of nucleic acid molecules is operably linked to a separate, distinct and/or different promoter. In some embodiments, one or more of the nucleic acid molecules are operably linked to the same promoter. In one embodiment, the nucleic acid molecules encoding the homing receptor, the CAR, the Fc receptor and the cytokine are operably linked to the same promoter or a single promoter. In some embodiments the promoter is an inducible promoter. In one embodiment, the nucleic acid molecule encoding the cytokine is located downstream or 3' of the nucleic acid molecules encoding the homing receptor, the CAR, and the Fc receptor (e.g., CD16 or high affinity CD16).

In some embodiments, the NK-92® cells express the proteins encoded by the nucleic acid molecules described herein on the cell surface. For example, in some embodiments, the modified NK-92® cells express the homing receptor, the ABP or CAR, and the Fc receptor (e.g., CD16 or high affinity CD16) on the cell surface.

Also provided are compositions and kits comprising the modified NK-92® cells. Provided are methods of making the modified cells and methods of treating cancer using the cells.

In another aspect, methods for treating cancer or reducing the size of a tumor are described. In some embodiments, the methods of treating cancer or reducing the size of a tumor comprise administering to a subject in need thereof a therapeutically effective amount of the modified NK-92® cells described herein, wherein administration treats the cancer or reduces the size of a tumor in the subject. In some embodiments, the methods comprise administering to the subject a therapeutically effective amount of modified NK-92® cells that comprise a nucleic acid encoding a homing receptor, an ABP or CAR that specifically binds to a target antigen, an Fc Receptor such as CD16 or CD16-158V, and/or a cytokine such as erIL-2 or erIL-15. In some embodiments, the methods comprise administering to the subject a therapeutically effective amount of modified NK-92® cells that comprise a nucleic acid encoding a secreted cytokine, an ABP or CAR that specifically binds to a target antigen, an Fc Receptor such as CD16 or CD16-158V, and/or a cytokine such as erIL-2 or erIL-15.

In some embodiments, the NK cells described herein are administered with a TGF-β inhibitor to block TGF-β and help remove immunosuppression. In some embodiments, the NK cells described herein are administered with other immunotherapies to help decrease or eliminate a tumor. For example, TGF-β can be inhibited by intratumoral injection of inhibitory peptides in combination with intratumoral injections of poly(I:C) and an α-CD40 antibody. In some embodiments, the TGF-β inhibitor is combined with IL-2.

In another aspect, use of a composition described herein for treating a disease is provided. In some embodiments, a modified NK-92® cell described herein is provided for use as a medicament for treating a disease. In some embodiments, a modified NK-92® cell described herein is provided for use in the treatment of a disease. In some embodiments, the modified NK-92® cells comprise a nucleic acid encoding a homing receptor, an ABP or CAR that specifically binds to a target antigen, an Fc Receptor such as CD16 or CD16-158V, and/or a cytokine such as erIL-2 or erIL-15. In some embodiments, the modified NK-92® cells comprise a nucleic acid encoding a secreted cytokine, an ABP or CAR that specifically binds to a target antigen, an Fc Receptor such as CD16 or CD16-158V, and/or a cytokine such as erIL-2 or erIL-15. In some embodiments, the disease is cancer.

The details of one or more embodiments are set forth in the accompanying drawings and the description below. Other features, objects, and advantages will be apparent from the description and drawings, and from the claims.

Figure 16:
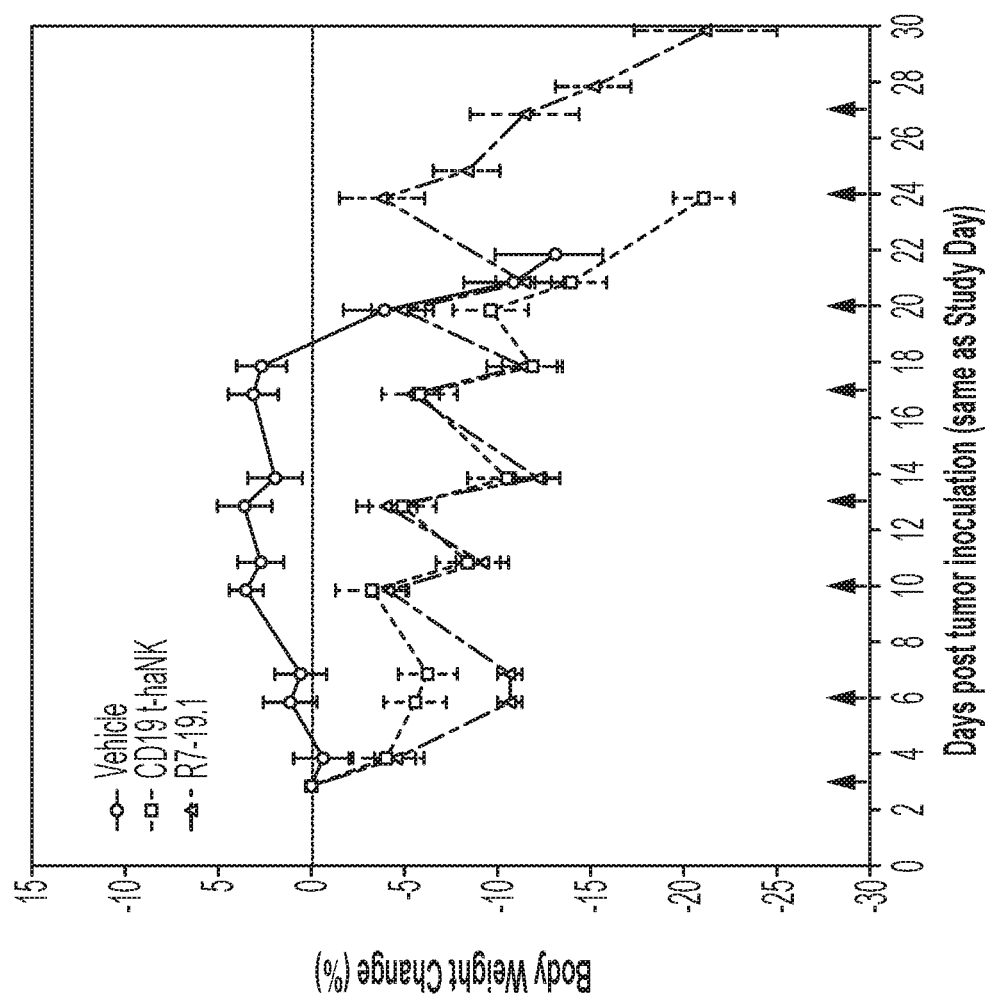

FIG. 16 illustrates the Body weight change in the IV Raji-19.5 tumor model. Body weight change curves (% change over Day 0 body weight) for IV Raji-19.5 tumor bearing animals treated with vehicle, CD19 t-haNK cells, or R7-19.1 cells. Data are Mean±SEM. Red arrows indicate dosing days. The weight measurements taken on dosing days were performed prior to dose administration. For all time points prior to Day 20 the curves for the NK cell treated groups reached statistically significant difference (P<0.05) compared to the vehicle control group by 2-way ANOVA followed by multiple comparison by Tukey test.

Figure 17:
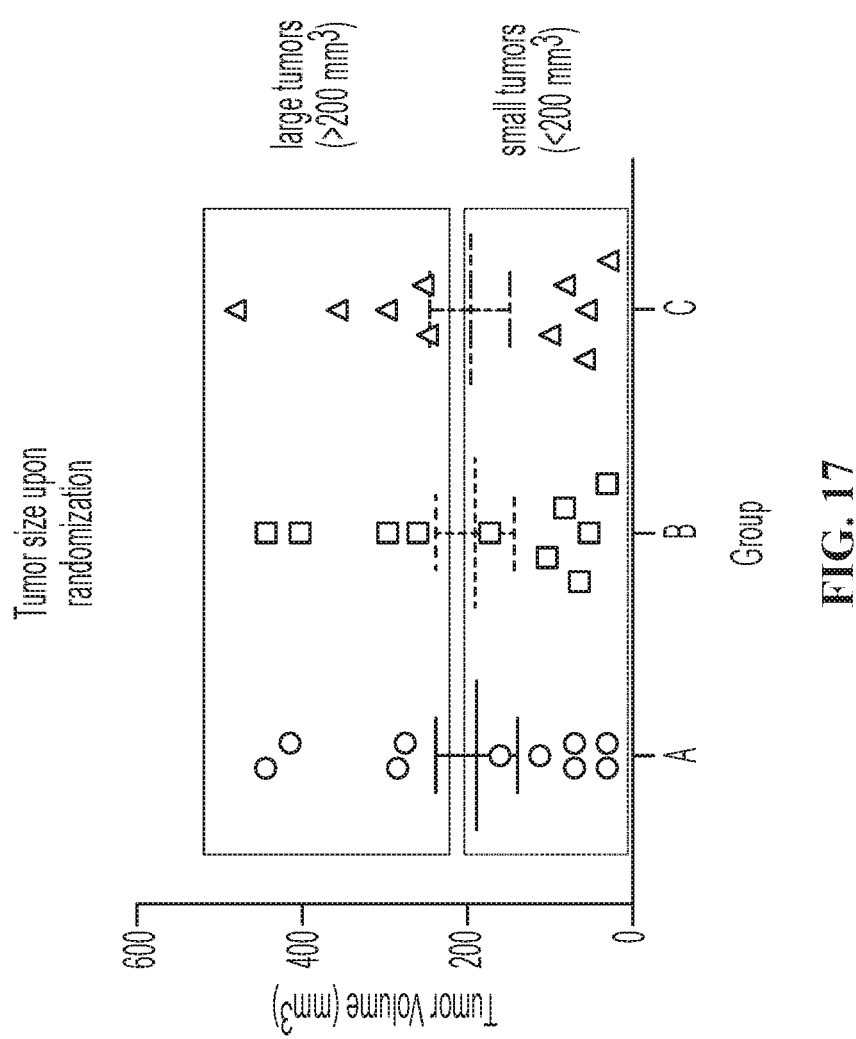

FIG. 17 illustrates the sizes of SC Raji-19.5 tumors upon randomization. Shown are individual tumor sizes upon randomization. The black box encircled large tumors that were >200 mm$^3$ in size, while the blue box encircled small tumors that were <200 mm$^3$. Group mean±SEM is also indicated.

Figure 18:
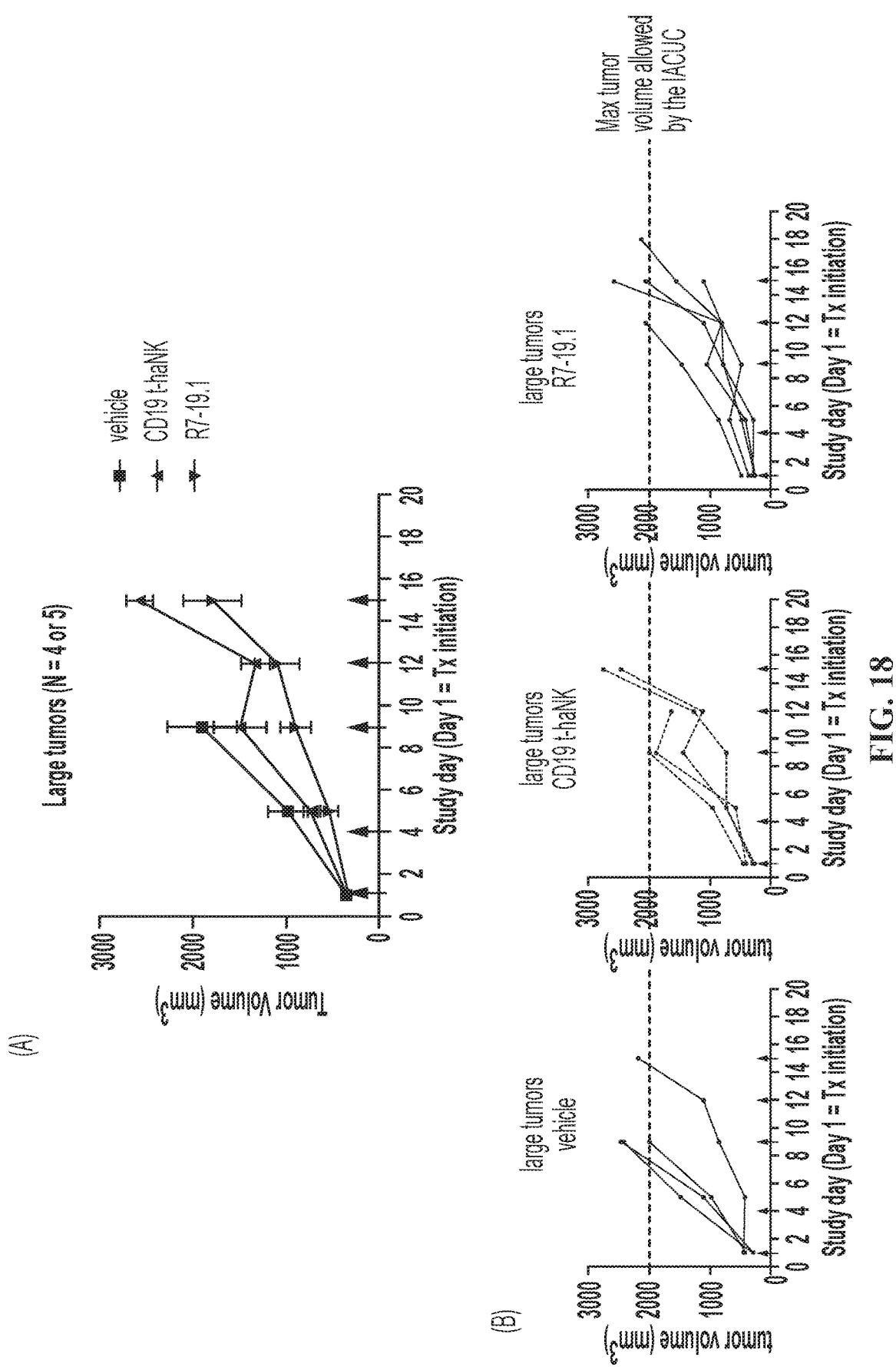

FIG. 18 illustrates tumor growth for the large-tumor sub-population of SC Raji-19.5 tumor-bearing mice. (A) Group analysis. Data are Mean±SEM. Statistical analyses were done using 2-way mixed-effects analysis followed by multiple comparison by Tukey test. No statistical significance was achieved. (B) Individual curves. Red arrows indicate dosing days. Tx: treatment.

Figure 19:
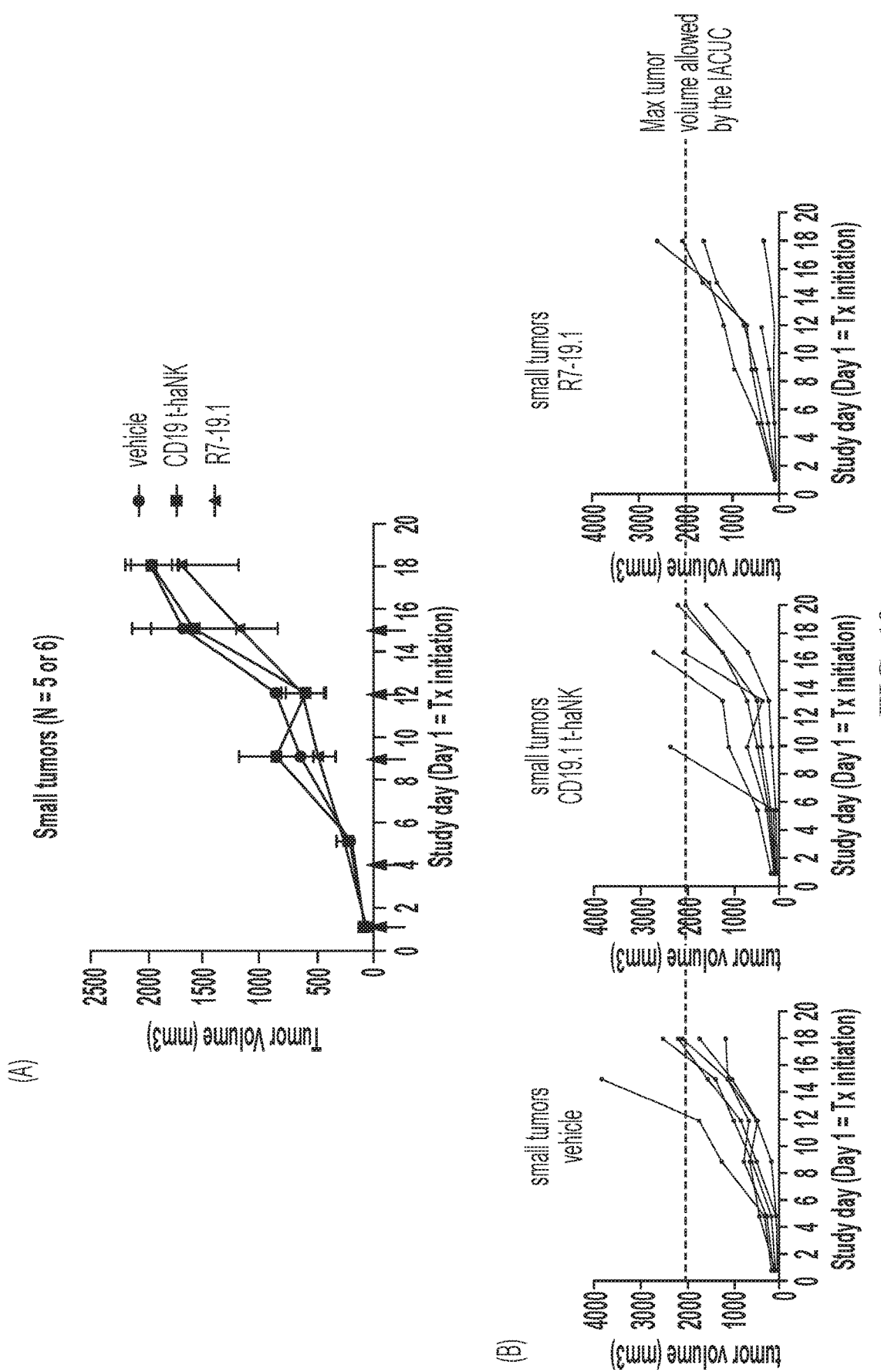

FIG. 19 illustrates tumor growth for the small-tumor sub-population of SC Raji-19.5 tumor-bearing mice. (A) Group analysis. Data are Mean±SEM. Statistical analyses were done using 2-way mixed-effects analysis followed by multiple comparison by Tukey test. No statistical significance was detected between any 2 groups at any time point. (B) Individual curves. Red arrows indicate dosing days. Tx: treatment.

Figure 20:
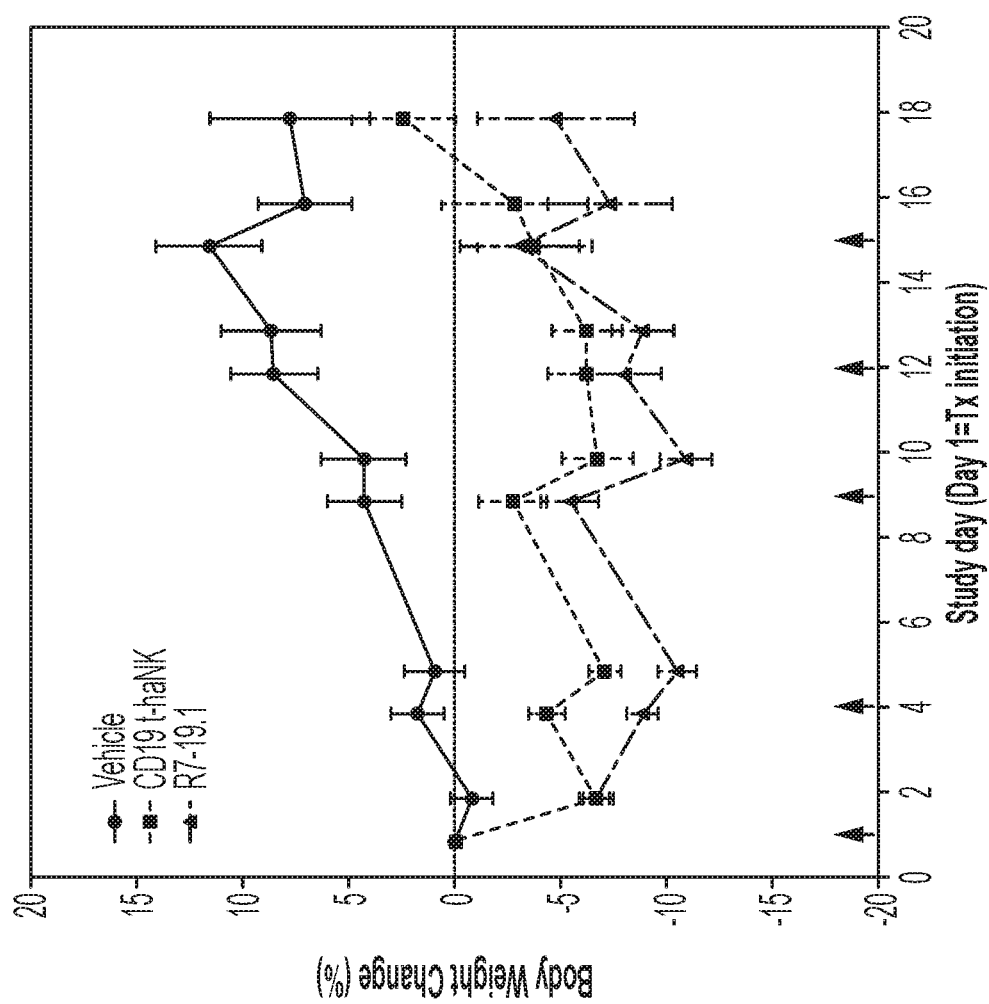

FIG. 20 illustrates body weight change in the SC Raji-19.5 tumor model. Body weight change curves (% change over Day 1 body weight) for SC Raji-19.5 tumor bearing animals treated with vehicle, CD19 t-haNK cells, or R7-19.1 cells. Data are Mean±SEM. Red arrows indicate dosing days. The body weight measurements taken on dosing days were performed prior to dose administration. For all time points prior to Day 16, the curves for the NK cell treated groups reached statistically significant difference compared to the vehicle control group by 2-way mixed-effects analysis followed by multiple comparison by Tukey test.

Figure 21:
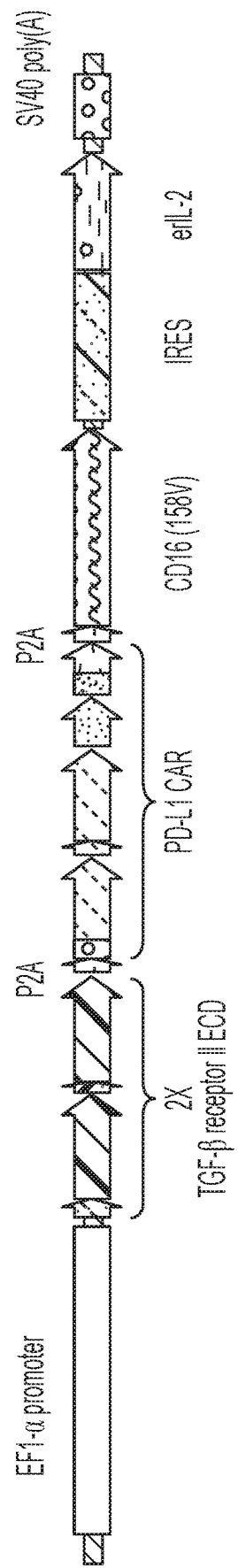

FIG. 21 illustrates one embodiment of a quadri-cistronic TGFβ-trap armored PD-L1 CAR construct.

Figure 22:
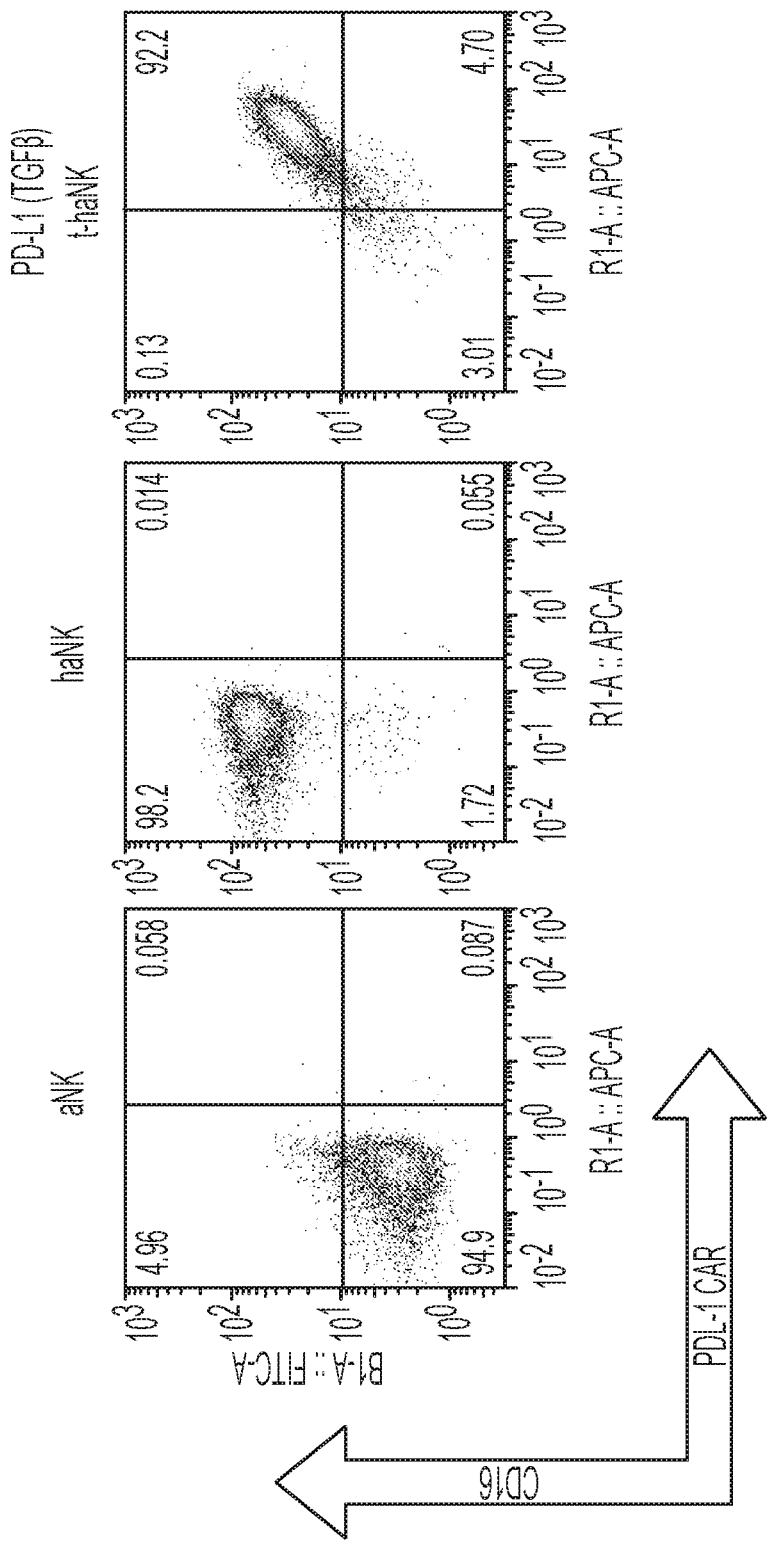

FIG. 22 illustrates expression analysis of PD-L1 CAR and CD16 in PD-L1 (TGFβ-trap) t-haNK Clones.

Figure 23:
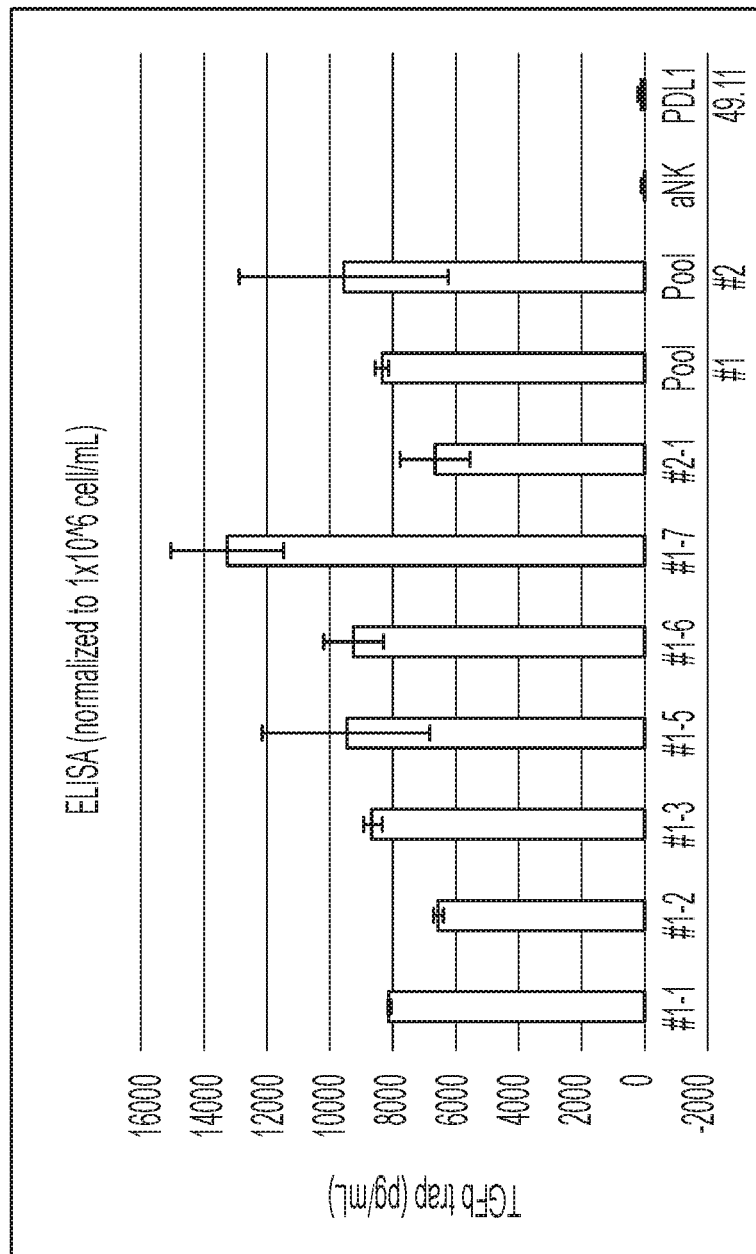

FIG. 23 illustrates TGFb trap is secreted into the culture supernatant of TGFβtrap/PD-L1 t-haNK clones.

Figure 24:
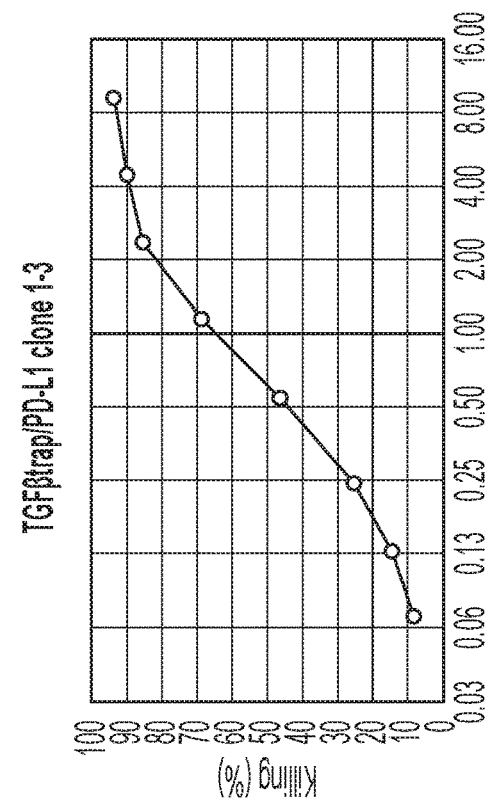
Figure 24:
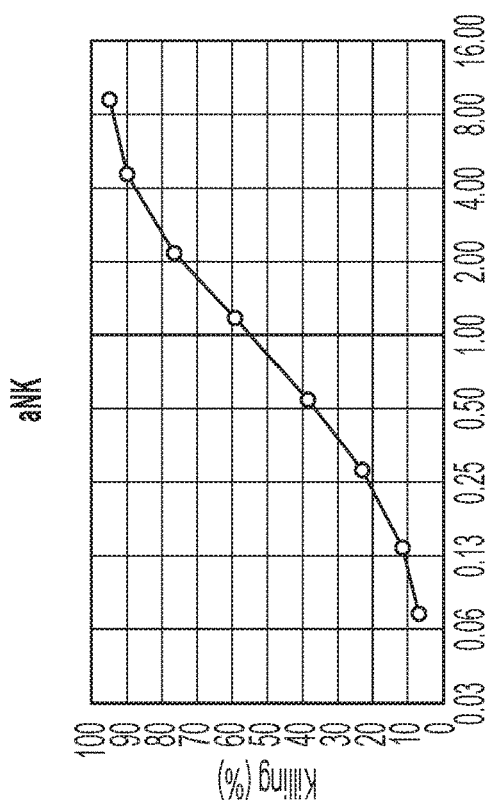

FIG. 24 illustrates cytotoxicity of the quadri-cistronic TGFβ-trap contruct against K562 target cells.

Figure 25:
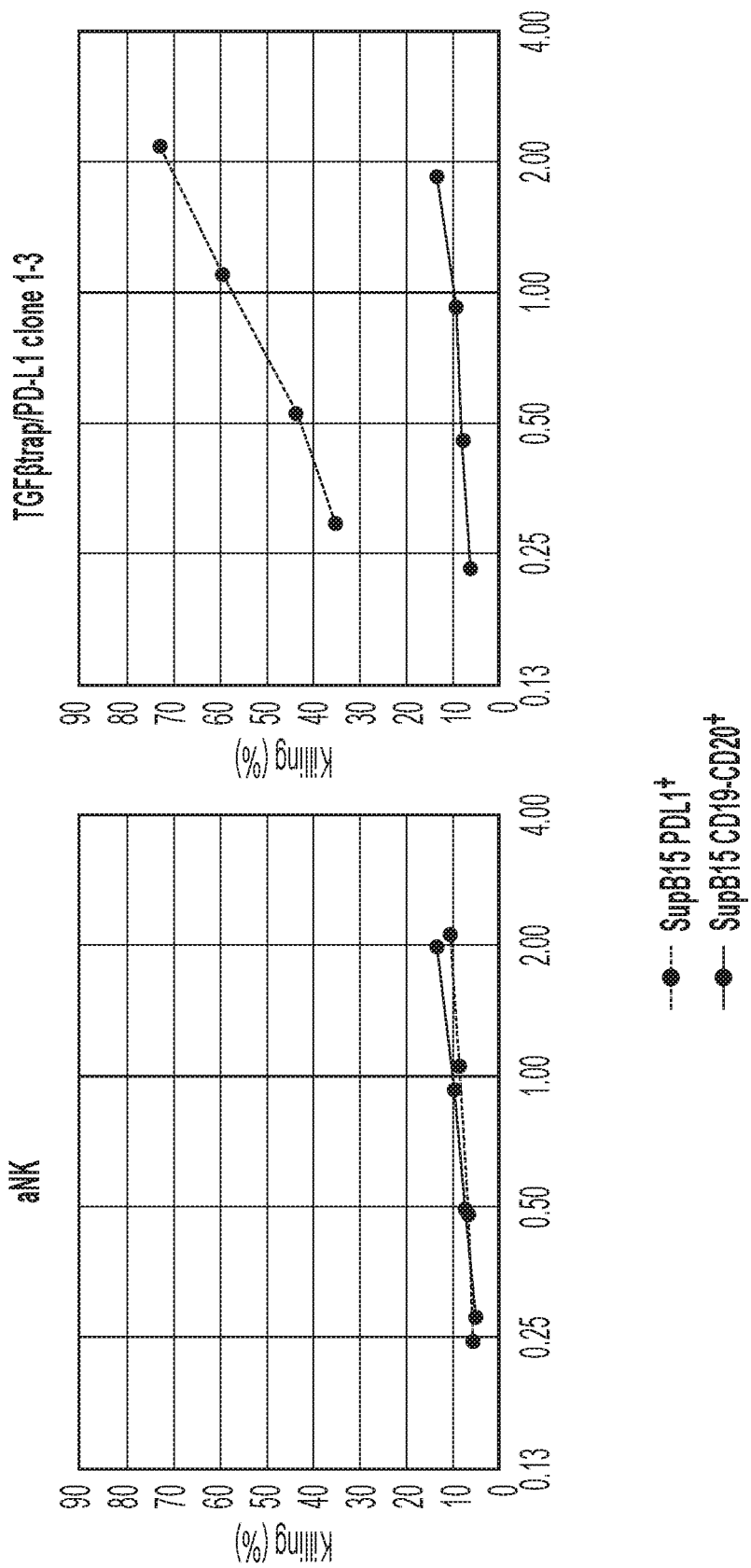

FIG. 25 illustrates CAR killing of the quadri-cistronic TGFβ-trap contruct against SUP-B15 target cells expressing PD-L1.

Figure 26:
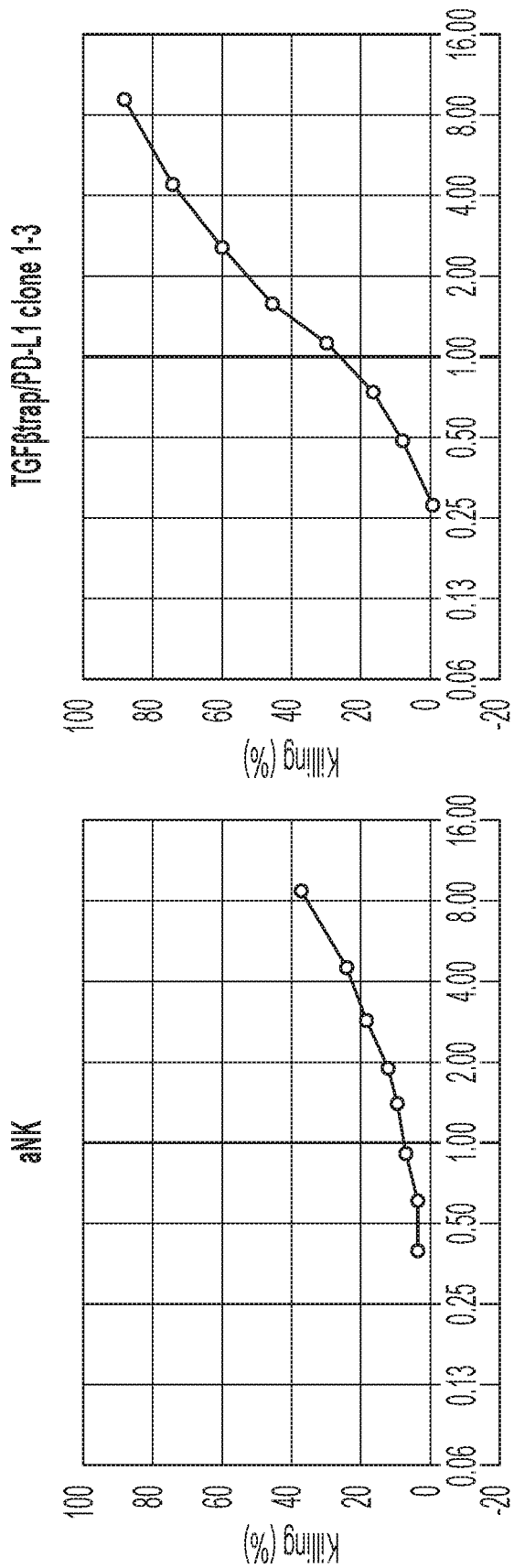

FIG. 26 illustrates CAR killing of the quadri-cistronic TGFβ-trap contruct against MDA-MB 231 target cells.

Figure 27:
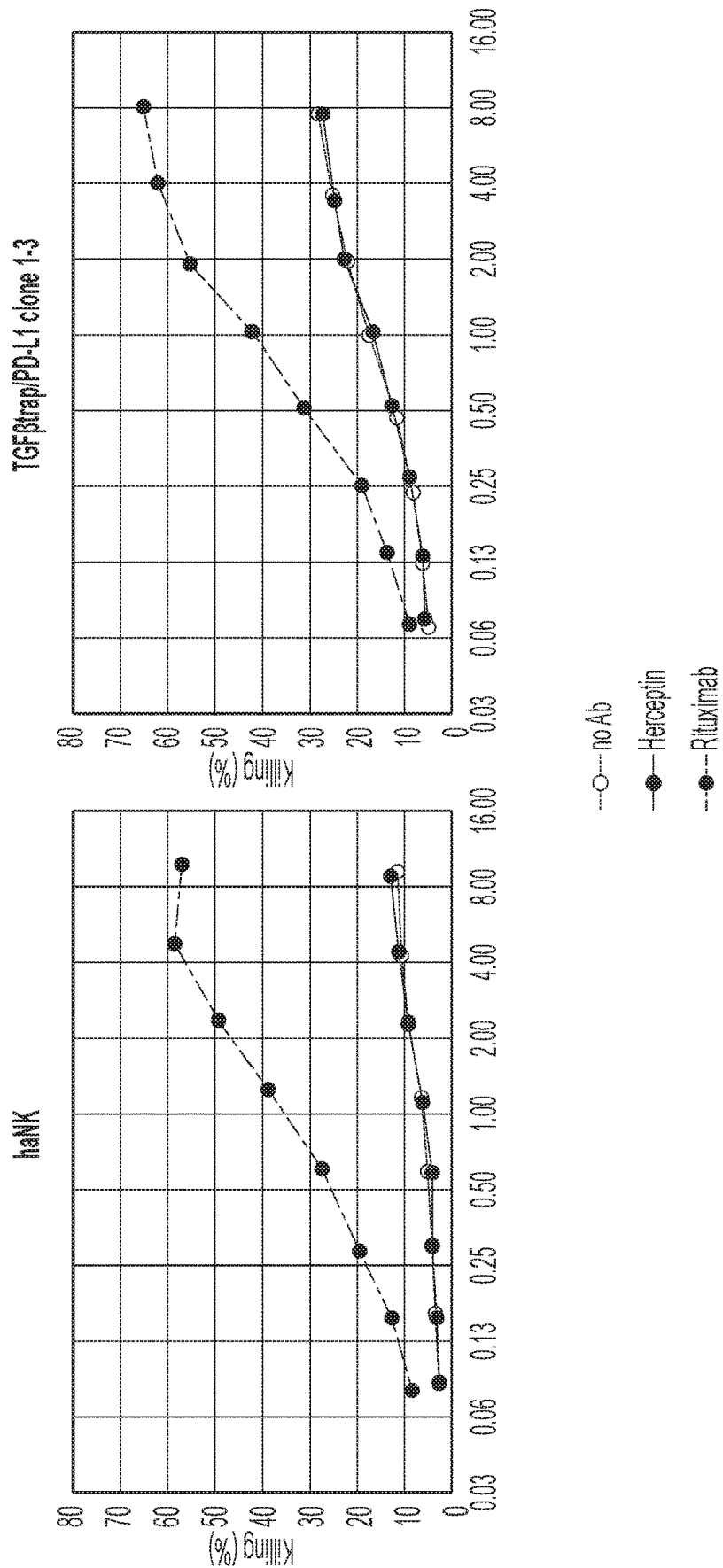

FIG. 27 illustrates ADCC of the quadri-cistronic TGFβ-trap contruct against SUP-B15$^{CD19-CD20+}$.

Figure 28:
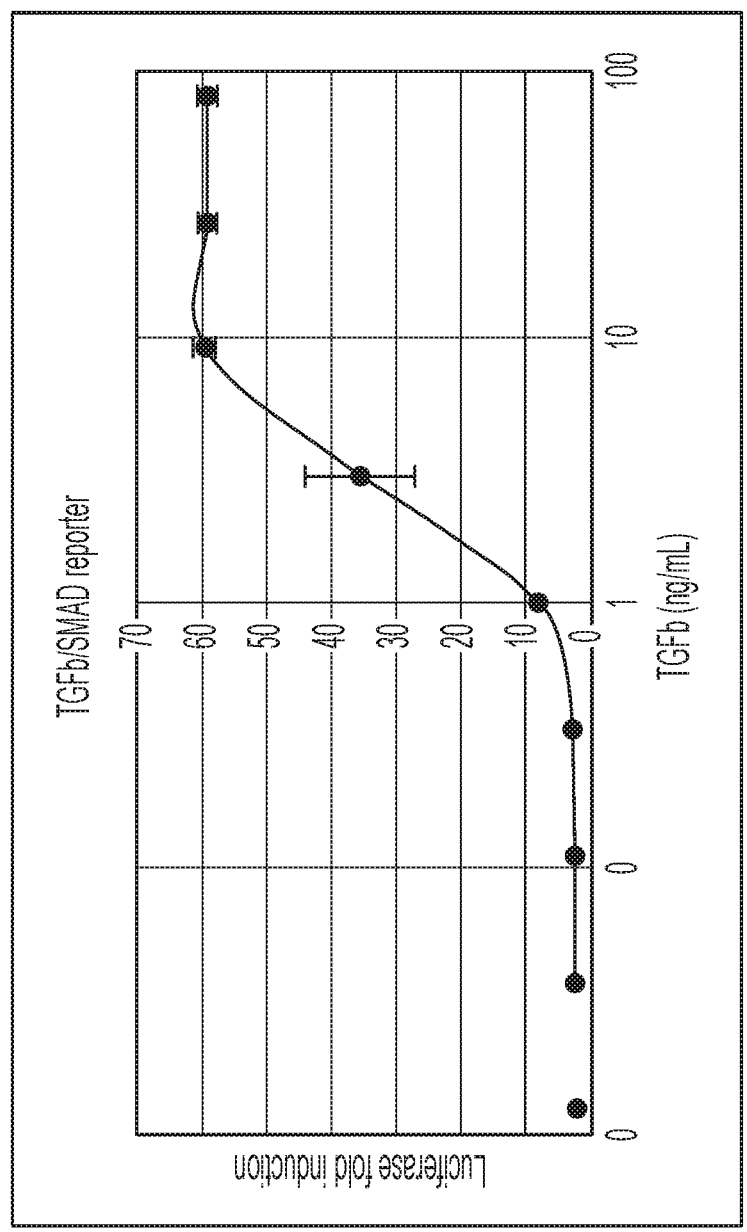

FIG. 28 illustrates TGFβ/SMAD Luciferase reporter HEK293 cells induced by TGFβ.

Figure 29:
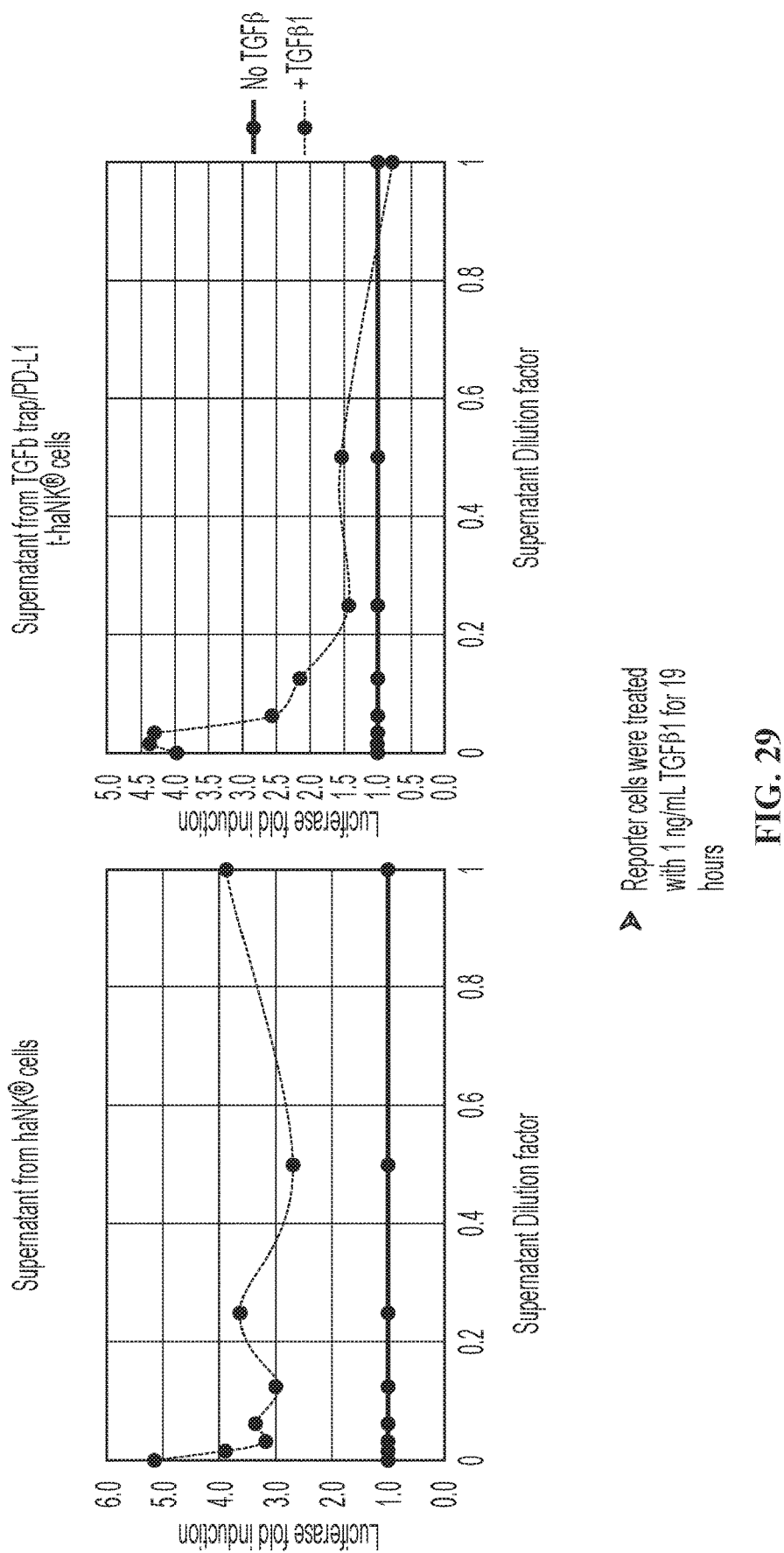

FIG. 29 illustrates secreted TGFβ-trap sequestered TGFβ and inhibited luciferase expression in HEK293T reporter assay.

Figure 30:
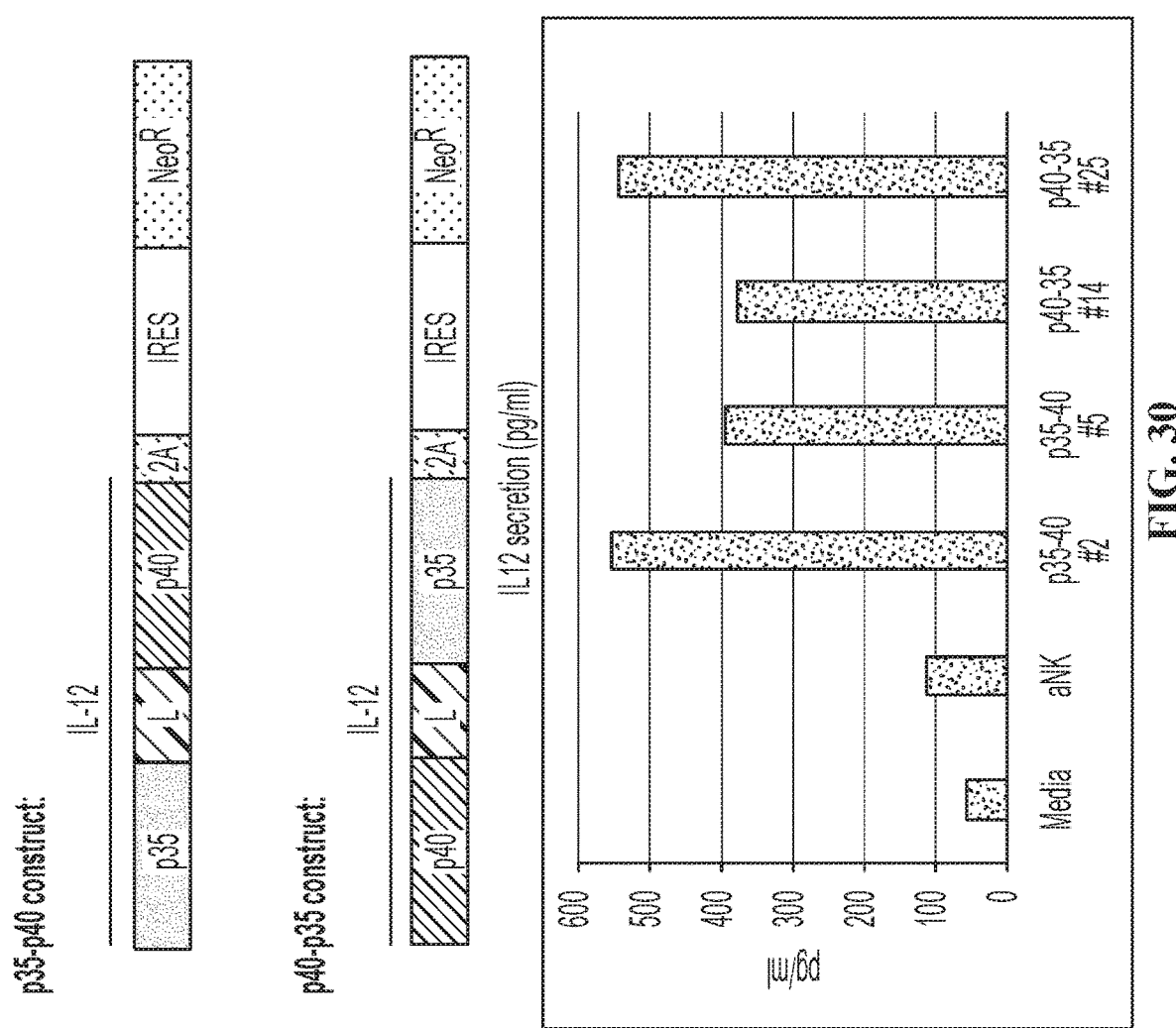

FIG. 30 illustrates IL-12 secretion from IL-12 virally transduced NK-92® cell lines.

Figure 31:
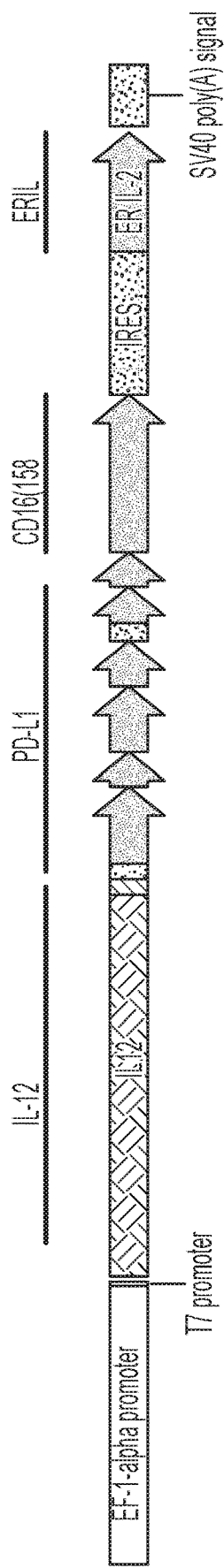

FIG. 31 illustrates one embodiment of a quadri-cistronic IL-12/PD-L1 t-haNK construct.

Figure 32:
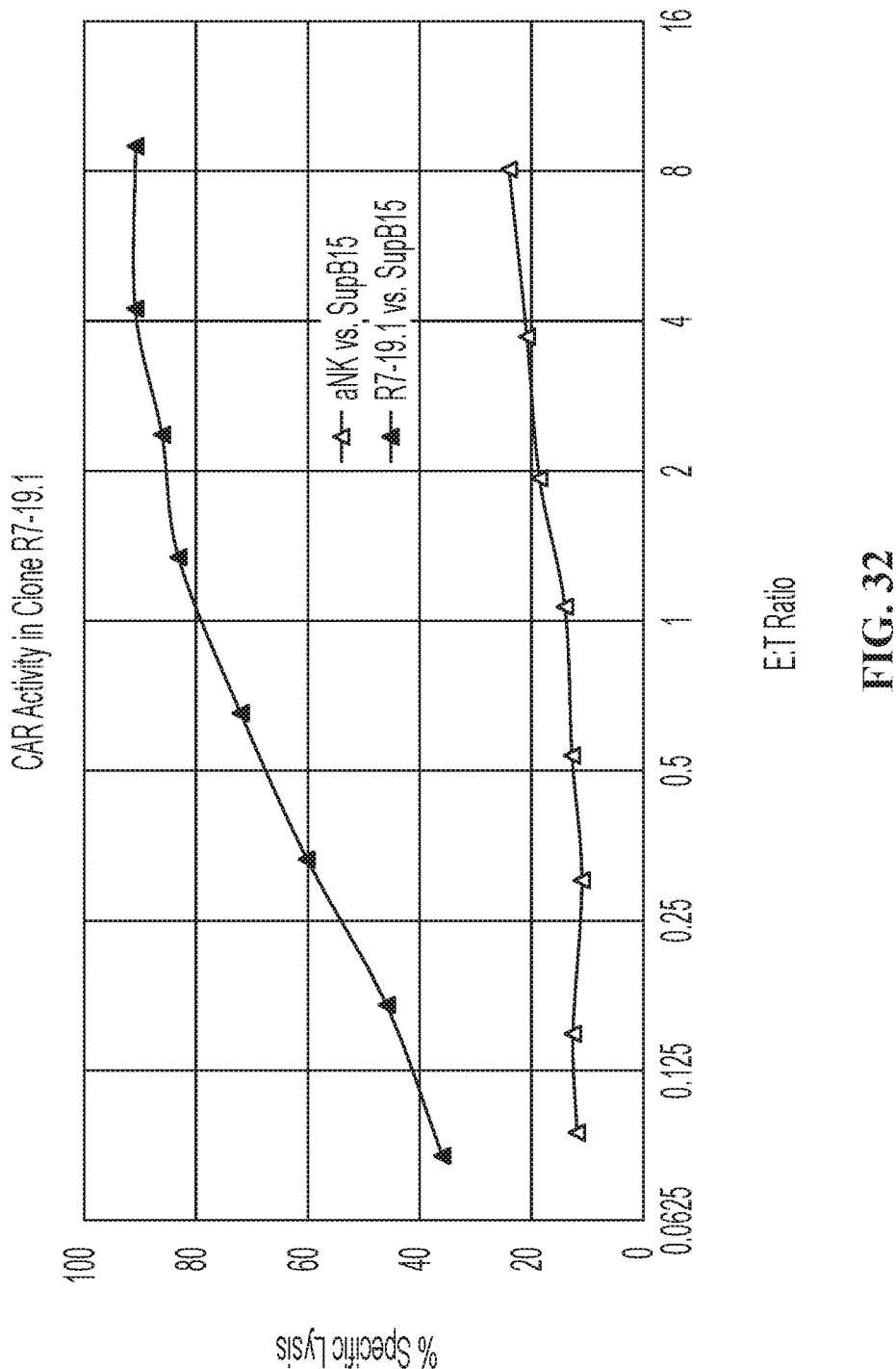

FIG. 32 illustrates cytotoxicity data for CCR7 CD19 t-haNK cells.

Figure 33:
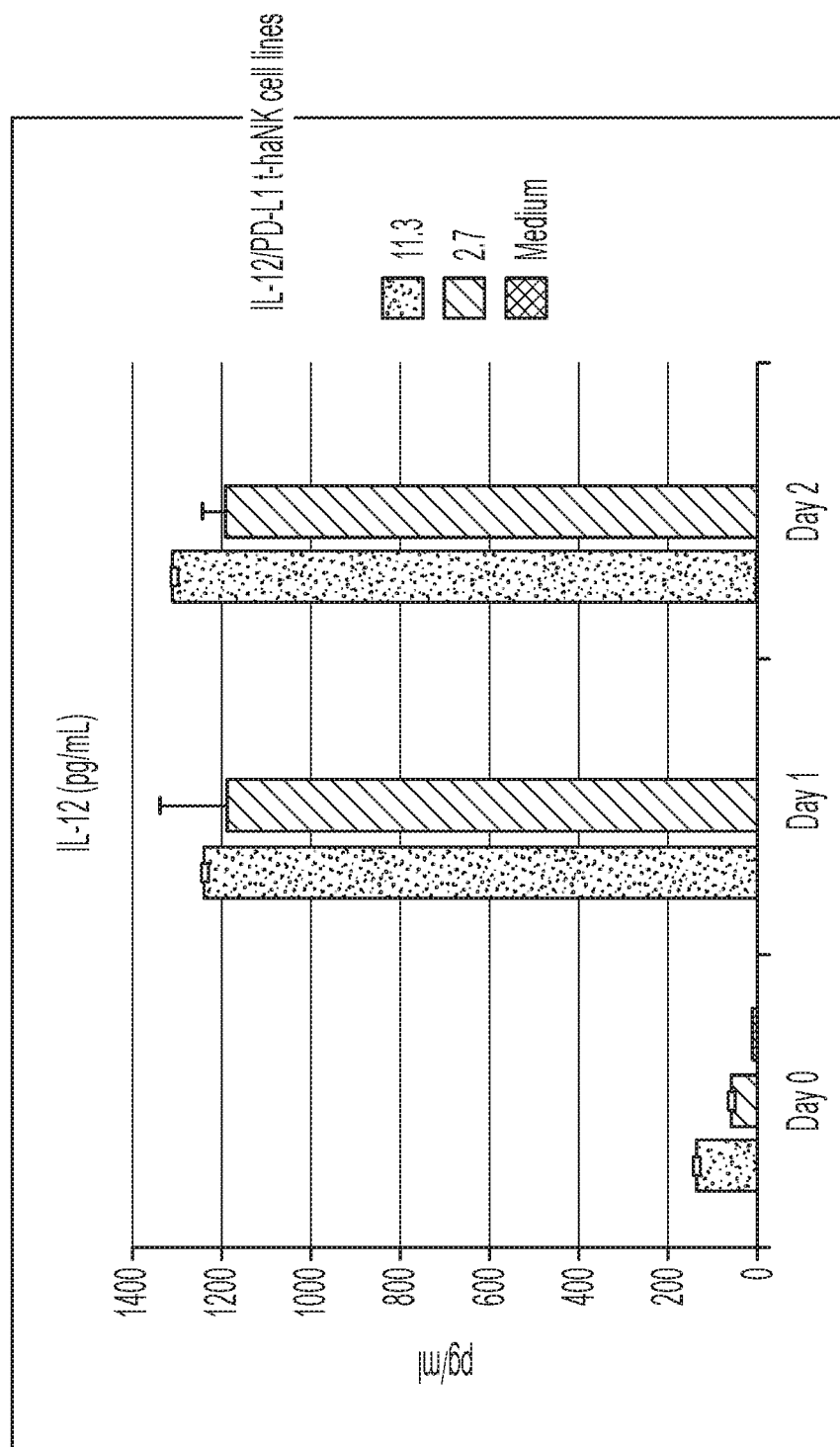

FIG. 33 illustrates IL-12 secretion from IL-12/PD-L1 t-haNK™ cell line.

DEFINITIONS

Unless defined otherwise, all technical and scientific terms used herein have the same meaning as commonly understood by one of ordinary skill in the art in the field of immunology and immunotherapy.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

All numerical designations, e.g., pH, temperature, time, concentration, amounts, and molecular weight, including ranges, include variations normally encountered by one of ordinary skill in the art. Therefore, numerical values can include variations of (+) or (−) increments of 0.1 or 1.0, where appropriate, depending on the relevant significant digit. It is to be understood, although not always explicitly stated, that all numerical designations may be preceded by the term "about." The term "about" as used herein may also mean that the value can vary by ±1%, 2%, 3%, 4%, 5%, 6%, 7%, 8%, 9%, or 10%.

It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this disclosure.

The term "homing receptor" refers to a receptor that activates a cellular pathway that results directly or indirectly in the cell migrating toward a target cell or tissue. For example, homing receptors expressed by leukocytes are used by leukocytes and lymphocytes to enter secondary lymphoid tissues via high endothelial venules. Homing receptors can also be used by cells to migrate toward the source of a chemical gradient, such as a chemokine gradient.

Examples of homing receptors include G-protein coupled receptors such as chemokine receptors, including but not limited to CCR1, CCR2, CCR3, CCR4, CCR5, CCR6, CCR7, CCR8, CCR9, CCR10, CXCR1, CXCR2, CXCR3, CXCR4, CXCR5, CXCR6, CXCR7, CX3CR1, XCR1, CCXCKR, D6, and DARC; cytokine receptors; cell adhesion molecules such as selectins, including L-selectin (CD62L), integrins such α4β7 integrin, LPAM-1, and LFA-1. Homing receptors generally bind to cognate ligands on the target tissues or cell. In some embodiments, homing receptors bind to Addressins on the endothelium of venules, such as mucosal vascular addressin cell adhesion molecule 1 (MAdCAM-1).

As used herein, "immunotherapy" refers to the use of NK-92® cells, modified or unmodified, naturally occurring or modified NK cell or T-cell, whether alone or in combination, and which are capable of inducing cytotoxicity when contacting a target cell.

As used herein, "natural killer (NK) cells" are cells of the immune system that kill target cells in the absence of a specific antigenic stimulus, and without restriction according to major histocompatibility complex (MHC) class. NK cells are characterized by the presence of CD56 and the absence of CD3 surface markers.

The term "endogenous NK cells" is used to refer to NK cells derived from a donor (or the patient), as distinguished from the NK-92® cell line. Endogenous NK cells are generally heterogeneous populations of cells within which NK cells have been enriched. Endogenous NK cells may be intended for autologous or allogeneic treatment of a patient.

The term "NK-92" refers to natural killer cells derived from the highly potent unique cell line described in Gong et al. (1994), rights to which are owned by NantKwest® (hereafter, "NK-92® cells"). The immortal NK cell line was originally obtained from a patient having non-Hodgkin's lymphoma. Unless indicated otherwise, the term "NK-92®" is intended to refer to the original NK-92® cell lines as well as NK-92® cell lines that have been modified (e.g., by introduction of exogenous genes). NK-92® cells and exemplary and non-limiting modifications thereof are described in U.S. Pat. Nos. 7,618,817; 8,034,332; 8,313,943; 9,181,322; 9,150,636; and published U.S. application Ser. No. 10/008,955, all of which are incorporated herein by reference in their entireties, and include wild type NK-92®, NK-92®-CD16, NK-92®-CD16-γ, NK-92®-CD16-ζ, NK-92®-CD16 (F176V), NK-92®MI, and NK-92®CI. NK-92® cells are known to persons of ordinary skill in the art, to whom such cells are readily available from NantKwest, Inc.

The term "aNK" refers to an unmodified natural killer cells derived from the highly potent unique cell line described in Gong et al. (1994), rights to which are owned by NantKwest (hereafter, "aNK® cells"). The term "haNK" refers to natural killer cells derived from the highly potent unique cell line described in Gong et al. (1994), rights to which are owned by NantKwest, modified to express CD16 on the cell surface (hereafter, "CD16+NK-92® cells" or "haNK® cells"). In some embodiments, the CD16+NK-92® cells comprise a high affinity CD16 receptor on the cell surface. The term "taNK" refers to natural killer cells derived from the highly potent unique cell line described in Gong et al. (1994), rights to which are owned by NantKwest, modified to express a chimeric antigen receptor (hereafter, "CAR-modified NK-92® cells" or "taNK® cells"). The term "t-haNK" refers to natural killer cells derived from the highly potent unique cell line described in Gong et al. (1994), rights to which are owned by NantkWest, modified to express CD 16 on the cell surface and to express a chimeric antigen receptor (hereafter, "CAR-modified CD16+NK-92® cells" or "t-haNK cells"). In some embodiments, the t-haNK cells express a high affinity CD16 receptor on the cell surface.

The term "chemokine targeted t-haNK" and "Mi-T-haNK" refer to a t-haNK cell that is modified to express a chemokine receptor on the cell surface.

As used herein, the terms "cytotoxic" and "cytolytic," when used to describe the activity of effector cells such as NK-92® cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK-92® cells is due to cytolysis.

The term "kill" with respect to a cell/cell population is directed to include any type of manipulation that will lead to the death of that cell/cell population.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FCγR) bind to the IgG class of antibodies. FCγRIII-A (also called CD16) is a low affinity Fc receptor that binds to IgG antibodies and activates ADCC. FCγRIII-A are typically found on NK cells. NK-92® cells do not express FCγRIII-A. Fc-epsilon receptors (FcεR) bind to the Fc region of IgE antibodies.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92® cell is targeted to cells expressing certain antigens on the cell surface, based on the specificity of the scFv domain. The scFv domain can be engineered to recognize any antigen, including tumor-specific antigens. For example, CD19CAR recognizes CD19, a cell surface marker expressed by some cancers.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

"Homology" or "identity" or "similarity" refers to sequence similarity between two peptides or between two nucleic acid molecules. Sequence similarity can be determined by comparing a position in each sequence which may be aligned for purposes of comparison. When a position in the compared sequence is occupied by the same base or amino acid, then the molecules are homologous at that position. The percent of sequence similarity between sequences is a function of the number of matching or homologous positions shared by the sequences over a given comparison window. A sequence can be at least 60%, 70%, 80%, 85%, 90%, 91%, 92%, 93%, 94%, 95%, 96%, 97%, 98% or 99% identical to a sequence described herein.

The terms identical or percent identity, in the context of two or more nucleic acids or polypeptide sequences, refer to two or more sequences or subsequences that are the same or have a specified percentage of amino acid residues or nucleotides that are the same (i.e., at least about 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be substantially identical. This definition also refers to, or may be applied to, the compliment of a test sequence. The definition also includes sequences that have deletions and/or additions, as well as those that have substitutions. As described below, the preferred algorithms can account for gaps and the like. In some embodiments, identity exists over a region that is at least about 25 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer; subsequence coordinates are designated, if necessary; and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A comparison window, as used herein, includes reference to a segment of any one of the number of contiguous positions selected from the group consisting of from 20 to 600, usually about 50 to about 200, more usually about 100 to about 150, in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981); by the homology alignment algorithm of Needleman & Wunsch, J. Mol. Biol. 48:443 (1970); by the search for similarity method of Pearson & Lipman, Proc. Nat'l. Acad. Sci. USA 85:2444 (1988); by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection (see, e.g., Current Protocols in Molecular Biology (Ausubel et al., eds. 1995 supplement)).

A preferred example of an algorithm that is suitable for determining percent sequence identity and sequence similarity are the BLAST and BLAST 2.0 algorithms, which are described in Altschul et al., Nuc. Acids Res. 25:3389-3402 (1977), and Altschul et al., J. Mol. Biol. 215:403-410 (1990), respectively. BLAST and BLAST 2.0 are used, with the parameters described herein, to determine percent sequence identity for nucleic acids or proteins. Software for performing BLAST analyses is publicly available through the National Center for Biotechnology Information, as known in the art. This algorithm involves first identifying high scoring sequence pairs (HSPs) by identifying short words of a selected length (W) in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated for nucleotide sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The Expectation value (E) represents the number of different alignments with scores equivalent to or better than what is expected to occur in a database search by chance. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, expectation (E) of 10, and the BLOSUM62 scoring matrix (see Henikoff & Henikoff, Proc. Natl. Acad. Sci. USA 89:10915 (1989)), alignments (B) of 50, expectation (E) of 10, M=5, N=−4.

The term transformation as used herein refers to a process by which an exogenous or heterologous nucleic acid molecule (e.g., a vector or recombinant nucleic acid molecule) is introduced into a recipient cell. The exogenous or heterologous nucleic acid molecule may or may not be integrated into (i.e., covalently linked to) chromosomal DNA making up the genome of the host cell. For example, the exogenous or heterologous polynucleotide may be maintained on an episomal element, such as a plasmid. Alternatively or additionally, the exogenous or heterologous polynucleotide may become integrated into a chromosome so that it is inherited by daughter cells through chromosomal replication. Methods for transformation include, but are not limited to, calcium phosphate precipitation; fusion of recipient cells with bacterial protoplasts containing the recombinant nucleic acid; treatment of the recipient cells with liposomes containing the recombinant nucleic acid; DEAE dextran; fusion using polyethylene glycol (PEG); electroporation; magnetoporation; biolistic delivery; retroviral infection; lipofection; and micro-injection of DNA directly into cells.

The term transformed, as used in reference to cells, refers to cells that have undergone transformation as described herein such that the cells carry exogenous or heterologous genetic material (e.g., a recombinant nucleic acid). The term transformed can also or alternatively be used to refer to cells, types of cells, tissues, organisms, etc. that contain exogenous or heterologous genetic material.

The term introduce, as used herein with reference to introduction of a nucleic acid into a cell or organism, is intended to have its broadest meaning and to encompass introduction, for example by transformation methods (e.g., calcium-chloride-mediated transformation, electroporation, particle bombardment), and also introduction by other methods including transduction, conjugation, and mating. Optionally, a construct is utilized to introduce a nucleic acid into a cell or organism.

The terms modified and recombinant when used with reference to a cell, nucleic acid, polypeptide, vector, or the like indicates that the cell, nucleic acid, polypeptide, vector or the like has been modified by or is the result of laboratory methods and is non-naturally occurring. Thus, for example, modified cells include cells produced by or modified by laboratory methods, e.g., transformation methods for introducing nucleic acids into the cell. Modified cells can include nucleic acid sequences not found within the native (non-recombinant) form of the cells or can include nucleic acid sequences that have been altered, e.g., linked to a non-native promoter.

As used herein, the term exogenous refers to a substance, such as a nucleic acid (e.g., nucleic acids including regulatory sequences and/or genes) or polypeptide, that is artificially introduced into a cell or organism and/or does not naturally occur in the cell in which it is present. In other words, the substance, such as nucleic acid or polypeptide, originates from outside a cell or organism into which it is introduced. An exogenous nucleic acid can have a nucleotide sequence that is identical to that of a nucleic acid naturally present in the cell. For example, an NK-92® cell can be engineered to include a nucleic acid having a NK-92® sequence, e.g., heparanase. Optionally, an endogenous NK-92® heparanase sequence is operably linked to a gene with which the regulatory sequence is not involved under natural conditions. Although the NK-92® heparanase sequence may naturally occur in the host cell, the introduced nucleic acid is exogenous according to the present disclosure. An exogenous nucleic acid can have a nucleotide sequence that is different from that of any nucleic acid that is naturally present in the cell. For example, the exogenous nucleic acid can be a heterologous nucleic acid, i.e., a nucleic acid from a different species or organism. Thus, an exogenous nucleic acid can have a nucleic acid sequence that is identical to that of a nucleic acid that is naturally found in a source organism but that is different from the cell into which the exogenous nucleic acid is introduced. As used herein, the term endogenous, refers to a nucleic acid sequence that is native to a cell. As used herein, the term heterologous refers to a nucleic acid sequence that is not native to a cell, i.e., is from a different organism than the cell. The terms exogenous and endogenous or heterologous are not mutually exclusive. Thus, a nucleic acid sequence can be exogenous and endogenous, meaning the nucleic acid sequence can be introduced into a cell but have a sequence that is the same as or similar to the sequence of a nucleic acid naturally present in the cell. Similarly, a nucleic acid sequence can be exogenous and heterologous meaning the nucleic acid sequence can be introduced into a cell but have a sequence that is not native to the cell, e.g., a sequence from a different organism.

As described herein, a control or standard control refers to a sample, measurement, or value that serves as a reference, usually a known reference, for comparison to a test sample, measurement, or value. For example, a test cell, e.g., a cell transformed with nucleic acid sequences encoding genes for an Fc Receptor can be compared to a known normal (wild-type) cell (e.g., a standard control cell). A standard control can also represent an average measurement or value gathered from a population of cells (e.g., standard control cells) that do not express the Fc Receptor or that do not have or have minimal levels of Fc Receptor activity. One of skill will recognize that standard controls can be designed for assessment of any number of parameters (e.g., RNA levels, polypeptide levels, specific cell types, and the like).

The term "express" refers to the production of a gene product (e.g., a protein). The term "transient" when referring to expression means a polynucleotide is not incorporated into the genome of the cell. The term "stable" when referring to expression means a polynucleotide is incorporated into the genome of the cell, or a positive selection marker (i.e., an exogenous gene expressed by the cell that confers a benefit under certain growth conditions) is utilized to maintain expression of the transgene.

The term "cytokine" or "cytokines" refers to the general class of biological molecules which affect cells of the immune system. Exemplary cytokines include but are not limited to interferons and interleukins (IL)—in particular IL-2, IL-12, IL-15, IL-18 and IL-21. In preferred embodiments, the cytokine is IL-2.

The term "cytokine that modulates the tumor microenvironment" refers to a molecule that is expressed by NK-92® cells and functions to increase the anti-tumor response. Certain cytokines can inhibit the endogenous immune system's response to the tumor, and therefore decrease the effectiveness of immunotherapies in treating cancer. Therefore, the term also includes inhibitors of cytokines that promote tumor growth, such as peptide inhibitors and/or ligands or receptors that bind to cytokines that promote tumor growth, for example ligand traps.

As used herein, the term "vector" refers to a non-chromosomal nucleic acid comprising an intact replicon such that the vector may be replicated when placed within a permissive cell, for example by a process of transformation. A vector may replicate in one cell type, such as bacteria, but have limited or no ability to replicate in another cell, such as mammalian cells. Vectors may be viral or non-viral. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In one embodiment, the vector is a viral vector, e.g. adenovirus. Viral vectors are well known in the art.

As used herein, the term "targeted," when referring to protein expression, is intended to include, but is not limited to, directing proteins or polypeptides to appropriate destinations in the cell or outside of it. The targeting is typically achieved through signal peptides or targeting peptides, which are a stretch of amino acid residues in a polypeptide chain. These signal peptides can be located anywhere within a polypeptide sequence, but are often located on the N-terminus. Polypeptides can also be engineered to have a signal peptide on the C-terminus. Signal peptides can direct a polypeptide for extracellular section, location to plasma membrane, golgi, endosomes, endoplasmic reticulum, and other cellular compartments. For example, polypeptides with a particular amino acid sequence on their C-terminus (e.g., KDEL) are retained in the ER lumen or transported back the ER lumen.

As used herein, the term "target," when referring to targeting of a tumor, refers to the ability of NK-92® cells to recognize and kill a tumor cell (i.e., target cell). The term "targeted" in this context refers, for example, to the ability of a CAR expressed by the NK-92® cell to recognize and bind to a cell surface antigen expressed by the tumor.

As used herein, the term "transfect" refers to the insertion of nucleic acid into a cell.

Transfection may be performed using any means that allows the nucleic acid to enter the cell. DNA and/or mRNA may be transfected into a cell. Preferably, a transfected cell expresses the gene product (i.e., protein) encoded by the nucleic acid.

Titles or subtitles may be used in the specification for the convenience of a reader, which are not intended to influence the scope of the present invention. Additionally, some terms used in this specification are more specifically defined below.

DETAILED DESCRIPTION

Provided herein are engineered cells using the cytotoxic activated Natural Killer cell line (NK-92) as the basis to improve immunotherapies to cancer and tumors, and/or to increase homing (migration) towards a target of interest. In some embodiments, the NK-92® cells are engineered to express a homing receptor known to direct lymphocytes to lymph nodes when expressed. In some embodiments, the NK-92® cells are engineered to express a secreted cytokine that modulates the tumor microenvironment or an inhibitor that blocks a cytokine that modulates the tumor microenvironment.

The disclosure provides the benefit of using a quadracistronic vector to insert multiple genes driven by a single highly active promoter to produce stable immunotherapeutic cell lines for use in clinical immunotherapies. A quadracistronic vector uses one or more approaches including P2A peptides and IRES elements to string together four genes under control of a single promoter, and tied to the expression of the final element—in this case a selective agent which requires expression for cellular survival and/or expansion.

In the proof of concept embodiment, the four genes used to generate a modified gene expression profile in the therapeutic cell line are: CCR7, a CD19 chimeric antigen receptor, the high-affinity variant of CD16, and endoplasmic reticulum bound IL-2. The ER-bound IL-2 serves as a selection agent, in addition to it's role in stimulating the cytotoxic capabilities of the NK-92® based cell line into which it is integrated. The IL-2 producing gene is placed last in the quadracistronic vector, furthest from the promoter and thus the most likely element to be lost should the gene construct fragment (leading to negative selection and self-excision from the pool, since the cells require IL-2 for continued survival). If, however, all elements successfully integrate into the genome, the cells will be selected through the removal of IL-2 from the media as only those cells which have integrated their own source of IL-2 survive. As the IL-2 element is furthest from the promoter, this favors a complete integration of the entire cassette of four elements—which can be further verified through flow cytometry staining analysis of the other components (see Examples).

The constructs described herein provide the advantage of reducing the development time in generating new therapeutic cell lines, as well as reducing the stress and adverse effects on the cells from multiple rounds of genomic manipulation and subsequent selection. In addition, by putting the selective agent (in this case ER-IL-2) at the end of the construct, it is expected that it will be difficult for the cells to silence any given component of the construct without resulting in IL-2 starvation, due to the nature of RNA transcription and processing. Thus stable cell lines constructed in this manner should retain expression of all the components which have been included in the vector, so long as they continue to produce their own IL-2.

To demonstrate proof-of-concept, four specific goals are addressed by the 4 components which are a part of this quadracistronic construct. The IL-2 functions as the selective agent and is a known agonist of the cytotoxic effect of NK-92® cells which makes them effective cancer therapeutics. The CCR7 element (C-C Chemokine Receptor type 7) is a chemokine receptor responsible for making immune cells which express it migrate in the direction of chemokine gradients of ligands CCL19 and CCL21, commonly expressed in the lymph nodes. In one embodiment, the CCR7 element contemplated herein may comprise a polynucleotide sequence having at least 80%, 85%, 90%, 91%, 92%, 93%, 94%, 95%, 96%, 97%, 98% or 99% identity to SEQ ID NO: 1 (CCR7 sequence). In one embodiment, the CCL21 contemplated herein may comprise a polynucleotide sequence having at least 80%, 85%, 90%, 91%, 92%, 93%, 94%, 95%, 96%, 97%, 98% or 99% identity to SEQ ID NO: 2 (CCL21 sequence). In one embodiment, the CCL19 contemplated herein may comprise a polynucleotide sequence having at least 80%, 85%, 90%, 91%, 92%, 93%, 94%, 95%, 96%, 97%, 98% or 99% identity to SEQ ID NO: 16 (CCL19 sequence).

The CD19 CAR (chimeric antigen receptor) is a construct used to increase the cytotoxicity of the cells when they encounter the CD19 cluster of differentiation on the surface of cells they encounter—this is a cluster of differentiation which is commonly expressed on B-cells, both normal and malignant, and has shown efficacy in directed immunotherapy trials against B cell lymphomas. The high-affinity CD16 receptor allows the modified NK-92® cells to recognize and respond to cells which have been recognized by IgG antibodies, such as those used as monoclonal antibodies in cancer treatment regimens like Rituxumab and Herceptin. When an immune cell armed with the CD16 receptor encounters a cell coated in one of these antibodies, it triggers ADCC (antibody dependent cellular cytotoxicity), and attempts to destroy the cell. In practical terms, this allows for cells which have been so armed to be used in combination therapy regimens with monoclonal antibodies against cancer neoantigens or the like. While each of these components has a utility by itself, combining this specific combination will, it is proposed, create a potent therapy for B-cell lymphomas—capable of migrating to the common sites of tumor outgrowth (lymph nodes), there recognizing the B-cell antigen CD19 and initiating CAR-mediated cytotoxicity, or acting with a monoclonal antibody like Rituxumab to avoid the potential for antigen escape. It will be understood that this proof of concept example is non-limiting, and that NK-92® cells can be modified using the methods described herein to express other homing receptors and/or CARs that target other antigens of interest in order to produce effective immunotherapeutic cell lines.

As described herein, modified NK-92® cells have been generated with stable long-term expression of the CCR7 lymph node homing receptor driven by the Elongation Factor 1a (EF1a) promoter after electroporation with a linearized gene construct containing a CCR7 expression cassette along with a removable selection cassette comprising a selectable marker. After one week of Puromycin selection, followed by serial dilution cloning, monoclonal cell lines were established retaining a high level of CCR7 expression. These CCR7 overexpressing NK cells have functional responses to lymph node associated chemokines CCL21 and CCL19 in migration/invasion assays. In one embodiment, the EF1a promoter contemplated herein may comprise a polynucleotide sequence having at least 80%, 85%, 90%, 91%, 92%, 93%, 94%, 95%, 96%, 97%, 98% or 99% identity to SEQ ID NO: 3 (EF1a promoter sequence).

In some exemplary embodiments, the chemokines and homing receptors contemplated herein may may comprise a polypeptide sequence or a polynucleotide sequence having at least 80%, 85%, 90%, 91%, 92%, 93%, 94%, 95%, 96%, 97%, 98% or 99% identity to SEQ ID NO: 44 (CCR7 a.a. sequence), or SEQ ID NO: 45 (CCL19 a.a. sequence), or SEQ ID NO: 46 (CCL21 a.a. sequence), or SEQ ID NO: 47 (CXCR2 n.t. sequence), or SEQ ID NO: 48 (CXCR2 a.a. sequence), or SEQ ID NO: 49 (CXCL14 n.t. sequence), or SEQ ID NO: 50 (CXCL14 a.a. sequence), or SEQ ID NO: 51 (CD62L n.t. sequence), or SEQ ID NO: 52 (CD62L a.a. sequence), or SEQ ID NO: 53 (IL-8 n.t. sequence), or SEQ ID NO: 54 (IL-8 a.a. sequence), or SEQ ID NO: 55 (CXCL1 n.t. sequence), or SEQ ID NO: 56 (CXCL1 a.a. sequence).

Target engagement of susceptible cell lines is shown to be recognized in NK-92® cells by activation of the NFAT transcription factor and its nuclear translocation. Target binding involving the FceRIg or CD3zeta pathway (including ADCC or CAR mediated target recognition) is sufficient to induce NFAT activation in NK-92® cells. This was demonstrated by inserting a reporter cassette containing 3 stop region flanking NFAT binding domains and a minimal promoter driving firefly luciferase. NFAT activation by the CD3zeta pathway through electroporation of CD19 CAR mRNA into this reporter cell line, followed by co-culture with SUP-B15 (CD19+, but resistant to non-specific cytotoxicity) resulted in luciferase expression.

In one embodiment, the NFAT Response Element Sequence (Binding site for activated NFAT) contemplated herein may comprise a polynucleotide sequence having at least 80%, 85%, 90%, 91%, 92%, 93%, 94%, 95%, 96%, 97%, 98% or 99% identity to SEQ ID NO: 4.

In one embodiment, the minimal promoter (downstream of 3 NFAT Response Elements) contemplated herein may comprise a polynucleotide sequence having at least 80%, 85%, 90%, 91%, 92%, 93%, 94%, 95%, 96%, 97%, 98% or 99% identity to SEQ ID NO: 5.

In one embodiment, the Complete NFAT Response Cassette (Poly-A+Pause site followed by 3 NFAT R.E. followed by Minimal Promoter) contemplated herein may comprise a polynucleotide sequence having at least 80%, 85%, 90%, 91%, 92%, 93%, 94%, 95%, 96%, 97%, 98% or 99% identity to SEQ ID NO: 6.

In one embodiment, the complete sequence of initial insertion (EF1a promoter, CCR7 gene with Poly-A, and LoxP flanked puromycin resistance gene driven by the ubiquitin promoter all encased in homology arms targeting the AAVS1 locus) contemplated herein may comprise a polynucleotide sequence having at least 80%, 85%, 90%, 91%, 92%, 93%, 94%, 95%, 96%, 97%, 98% or 99% identity to SEQ ID NO: 7.

In one embodiment, the complete sequence for second insertion (contains an NFAT response cassette driving CCL21+Poly-A, and a FRT-embedded blasticidin resistance gene driven by CMV) contemplated herein may comprise a polynucleotide sequence having at least 80%, 85%, 90%, 91%, 92%, 93%, 94%, 95%, 96%, 97%, 98% or 99% identity to SEQ ID NO: 8. The SEQ ID NO: 8 sequence may replace the LoxP flanked Puromycin resistance cassette from the first insertion, the FRT sequences surrounding the Blasticidin gene in this sequence to allow for later removal or replacement of that cassette using a similar Flp-FRT recombination.

The NK-92® cell line is a human, IL-2-dependent NK cell line that was established from the peripheral blood mononuclear cells (PBMCs) of a 50-year-old male diagnosed with non-Hodgkin lymphoma (Gong, et al., Leukemia. 8:652-8 (1994)). NK-92® cells are characterized by the expression of $CD56^{bright}$ and CD2, in the absence of CD3, CD8, and CD16. A $CD56^{bright}/CD16^{neg}$/low phenotype is typical for a minor subset of NK cells in peripheral blood, which have immunomodulatory functions as cytokine producers. Unlike normal NK cells, NK-92® lacks expression of most killer cell inhibitor receptors (KIRs) (Maki, et al., J Hemather Stem Cell Res. 10:369-83 (2001)). Only KIR2DL4, a KIR receptor with activating function and inhibitory potential that is expressed by all NK cells, was detected on the surface of NK-92. KIR2DL4 is considered to mediate inhibitory effects through binding to the HLA allele G (Suck, Cancer Immunol. Immunother. 65(4):485-92 (2015)). The predominant pathway of cytotoxic killing of NK-92® cells is through the perforin/esterase pathway; NK-92® expresses high levels of perforin and granzyme B (Maki, et al., J Hemather Stem Cell Res. 10:369-83 (2001)).

NK-92® cells have a very broad cytotoxic range and are active against cell lines derived from hematologic malignancies and solid tumors (Klingemann, Blood, 87(11): 4913-4 (1996); Swift, Haematologica. 97(7):1020-8 (2012); Yan, et al., Clin Cancer Res. 4:2859-68 (1998)). Safety assessments in severe combined immunodeficiency (SCID) mice showed no NK-92® treatment-related effects, such as acute toxicity or long-term carcinogenicity (Tam, et al., J Hemather. 8:281-90 (1999), Yan, et al., Clin Cancer Res. 4:2859-68 (1998)). Administration of NK-92® cells to mice challenged with human leukemia cells or mouse models of human melanoma resulted in improved survival and suppression of tumor growth, including complete remissions in some mouse tumors (Tam, et al., J Hemather. 8:281-90 (1999), Yan, et al., Clin Cancer Res. 4:2859-68 (1998)). Phase I clinical trials have confirmed its safety profile. Characterization of the NK-92® cell line is disclosed in WO 1998/49268 and U.S. Patent Application Publication No. 2002-0068044, which are incorporated by reference herein in their entireties.

Optionally, the modified NK-92® cells may also express the Fc receptor CD16. As used herein, the term "Fc receptor"

refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified by the type of antibody they recognize. For example, Fc-gamma receptors (FCγR) bind to the IgG class of antibodies. FCγRIII-A (also called CD16) is a low affinity Fc receptor that binds to IgG antibodies and activates ADCC. FCγRIII-A are typically found on NK cells. A representative amino acid sequence encoding CD16 is shown in SEQ ID NO:12. A representative polynucleotide sequence encoding CD16 is shown in SEQ ID NO:13. The complete sequences of CD16 can be found in the SwissProt database as entry P08637.

In some embodiments, the CD16 receptor comprises a phenylalanine (F) to valine (V) substitution at amino acid position 158 (F158V) in the IgG binding domain of the mature CD16 receptor (corresponding to Val at position 176 of the full length protein), which effects the antibody-dependent cell cytotoxic (ADCC) function of NK cells. The CD16 158V variant binds with higher affinity to human IgG1 and IgG3 than the 158F variant.

Optionally, the modified NK-92® cells comprise a nucleic acid sequence with 70%, 80%, 90%, or 95% identity to SEQ ID NO:13. Optionally, the modified NK-92® cells comprise a nucleic acid sequence with 90%, 91%, 92%, 93%, 94%, 95%, 96%, 97%, 98% or 99% identity to SEQ ID NO:13. Optionally, the modified NK-92® cells comprise a polypeptide with 70%, 80%, 90%, or 95% identity to SEQ ID NO:12 (having valine at position 176 of the full length polypeptide). Optionally, the modified NK-92® cells comprise a polypeptide with 90%, 91%, 92%, 93%, 94%, 95%, 96%, 97%, 98% or 99% identity to SEQ ID NO:12.

The cytotoxicity of NK-92® cells is dependent on the presence of cytokines (e.g., interleukin-2 (IL-2)). Thus, optionally, modified NK-92® cells are further modified to express at least one cytokine. Optionally, the at least one cytokine is IL-2, IL-12, IL-15, IL-18, IL-21 or a variant thereof. Optionally, the at least one cytokine is IL-2, IL-15 or a combination thereof. Optionally, the IL-2 and/or IL-15 is expressed with a signal sequence that directs the cytokine to the endoplasmic reticulum. Directing the IL-2 to the endoplasmic reticulum permits expression of IL-2 at levels sufficient for autocrine activation and without releasing substantial amounts of IL-2 extracellularly. See Konstantinidis et al "Targeting IL-2 to the endoplasmic reticulum confines autocrine growth stimulation to NK-92® cells" Exp Hematol. 2005 February; 33(2):159-64. A representative nucleic acid encoding IL-2 is shown in SEQ ID NO:14 and a representative polypeptide of IL-2 is shown in SEQ ID NO:15.

Optionally, the modified NK-92® cells comprise a nucleic acid sequence encoding IL-2, with 70%, 80%, 90%, or 95% identity to SEQ ID NO:14. Optionally, the modified NK-92® cells comprise a nucleic acid sequence with 90%, 91%, 92%, 93%, 94%, 95%, 96%, 97%, 98% or 99% identity to SEQ ID NO:14. Optionally, the modified NK-92® cells comprise a IL-2 polypeptide with 70%, 80%, 90%, or 95% identity to SEQ ID NO:15. Optionally, the modified NK-92® cells comprise a IL-2 polypeptide with 90%, 91%, 92%, 93%, 94%, 95%, 96%, 97%, 98% or 99% identity to SEQ ID NO:15. The provided modified NK-92® cells advantageously are capable of being maintained in the absence of IL-2 without secreting IL-2 in an amount to cause a clinical adverse effect.

In one aspect, the inventive subject matter comprises modified NK-92® cells that are capable of modulating the tumor microenvironment. The modified NK-92® cell preferably comprises a quadracistronic vector comprising one or more nucleic acids encoding i) IL-12 or a TGF-beta trap, ii) an Antigen Binding Protein (ABP) or Chimeric Antigen Receptor (CAR) that specifically binds to a target antigen, iii) an Fc Receptor such as CD16 or CD16-158V, and/or iv) a cytokine such as erIL-2 or erIL-15, wherein the nucleic acid sequence is operably linked to a promoter. In one embodiment, the quadracistronic vector contemplated herein is illustrated in FIGS. 21, 30, and 31 respectively. The IL-12 as contemplated herein may comprise a nucleic acid sequence with with at least 80%, 85%, 90%, 91%, 92%, 93%, 94%, 95%, 96%, 97%, 98% or 99% identity to SEQ ID NO: 57 (p35 n.t. sequence), or SEQ ID NO: 59 (p40 n.t. sequence). The IL-12 contemplated herein may also comprise an amino acid sequence with at least 80%, 85%, 90%, 91%, 92%, 93%, 94%, 95%, 96%, 97%, 98% or 99% identity to SEQ ID NO: 58 (p35 a.a. sequence, isoform 1 precurser), or SEQ ID NO: 60 (p40 a.a. sequence, precurser).

In one exemplary embodiment, the IL-12 single chain p40 p35 sequence in IL-2/PD-L1 Quadricistronic vector may comprise a polypeptide sequence with with at least 80%, 85%, 90%, 91%, 92%, 93%, 94%, 95%, 96%, 97%, 98% or 99% identity to SEQ ID NO: 61, or may comprise an polynucleotide sequence with at least 80%, 85%, 90%, 91%, 92%, 93%, 94%, 95%, 96%, 97%, 98% or 99% identity to SEQ ID NO: 62.

The TGF-beta trap as contemplated herein may comprise a polynucleotide sequence with with at least 80%, 85%, 90%, 91%, 92%, 93%, 94%, 95%, 96%, 97%, 98% or 99% identity to SEQ ID NO: 63 (TGFBRII extracellular domain), or SEQ ID NO: 65 (TGFb trap sequence). The TGF-beta trap contemplated herein may also comprise an amino acid sequence with at least 80%, 85%, 90%, 91%, 92%, 93%, 94%, 95%, 96%, 97%, 98% or 99% identity to SEQ ID NO: 64 (TGFBRII extracellular domain), or SEQ ID NO: 66 (TGFb trap sequence). Other suitable TGF-beta traps include those described in Mol. Canc. THer. 2012, Vol 11(7), 1477-1487.

Furthermore, the nucleic acid construct of the inventive subject matter may also comprises a sequence that encodes a 2A peptide, such as a T2A, P2A, E2A, or F2A peptide, in order to produce equimolar levels of polypeptides encoded by the same mRNA. The E2A peptide contemplated herein may comprise a polynucleotide sequence with at least 80%, 85%, 90%, 91%, 92%, 93%, 94%, 95%, 96%, 97%, 98% or 99% identity to SEQ ID NO: 17. The T2A peptide as contemplated herein may comprise a polynucleotide sequence with at least 80%, 85%, 90%, 91%, 92%, 93%, 94%, 95%, 96%, 97%, 98% or 99% identity to SEQ ID NO: 18.

In one exemplary, non-limiting example, the plasmid disclosed herein may comprise a polynucleotide sequence having at least 80%, 85%, 90%, 91%, 92%, 93%, 94%, 95%, 96%, 97%, 98% or 99% identity to SEQ ID NO: 19 (5' Homology arm of AAVS1), SEQ ID NO:20 (EF1a Promoter), SEQ ID NO: 21 (T7 Promoter), SEQ ID NO: 22 (CCR7 cDNA), SEQ ID NO: 23 (P2A element), SEQ ID NO: 24 (IgHC leader), SEQ ID NO: 25 (CD19 CAR minus signal peptide), SEQ ID NO: 26 (high affinity CD16), SEQ ID NO: 27 (IRES), SEQ ID NO: 28 (SC40 Poly-A), SEQ ID NO: 29 (3' Homology arm of AAVS1), and/or SEQ ID NO: 30 (Homology arm of AAVS1).

Chimeric Antigen Receptors

Optionally, the modified NK-92® cells are further engineered to express a chimeric antigen receptor (CAR) on the cell surface. Optionally, the CAR is specific for a tumor-specific antigen. Tumor-specific antigens are described, by way of non-limiting example, in US 2013/0189268; WO 1999024566 A1; U.S. Pat. No. 7,098,008; and WO 2000020460 A1, each of which is incorporated herein by reference in its entirety. Tumor-specific antigens include, without limitation, NKG2D, CS1, GD2, CD138, EpCAM, EBNA3C, GPA7, CD244, CA-125, ETA, MAGE, CAGE, BAGE, HAGE, LAGE, PAGE, NY-SEO-1, GAGE, CEA, CD52, CD30, MUCSAC, c-Met, EGFR, FAP, WT-1, PSMA, NY-ESO1, AFP, CEA, CTAG1B, CD19, CD33, B7-H4, CD20 and 41BB. CARs can be engineered as described, for example, in Patent Publication Nos. WO 2014039523; US 20140242701; US 20140274909; US 20130280285; and WO 2014099671, each of which is incorporated herein by reference in its entirety. Optionally, the CAR is a CD19 CAR, a CD33 CAR or CSPG-4 CAR. In one exemplary, non-limiting example, the CD19CAR CD3a may comprise a polynucleotide sequence having at least 80%, 85%, 90%, 91%, 92%, 93%, 94%, 95%, 96%, 97%, 98% or 99% identity to SEQ ID NO: 41.

Homing Receptors

Provided herein are modified NK-92® cells comprising a nucleic acid encoding a homing receptor. In some embodiments, the homing receptor is operably linked to a promoter. In some embodiments, the homing receptor is a G protein-coupled receptor In some embodiments, the homing receptor is a chemokine receptor selected from CCR1, CCR2, CCR3, CCR4, CCR5, CCR6, CCR7, CCR8, CCR9, CCR10, CXCR1, CXCR2, CXCR3, CXCR4, CXCR5, CXCR6, CXCR7, CX3CR1, XCR1, CCXCKR, D6, DARC, or the receptor for CXCL14. In some embodiments, the nucleic acid encoding CCR7 has at least 90%, 91%, 92%, 93%, 94%, 95%, 96%, 97%, 98% or 99% identity to SEQ ID NO:1. Optionally, the homing receptor is expressed on the cell surface of the modified NK-92® cells. Optionally, the modified NK-92® cells further comprise a CAR. Optionally, the CAR is CD19. Optionally, the modified NK-92® cells further comprise an Fc Receptor. Optionally, the Fc Receptor is CD16. Optionally, the modified NK-92® cells further comprise a cytokine, such as IL-2. In some embodiments, the IL-2 polypeptide may have a sequence with at least 80%, 85%, 90%, 91%, 92%, 93%, 94%, 95%, 96%, 97%, 98% or 99% identity to SEQ ID NO:42. In some embodiments, the IL-2 polypeptide may have a sequence with at least 80%, 85%, 90%, 91%, 92%, 93%, 94%, 95%, 96%, 97%, 98% or 99% identity to SEQ ID NO:43.

Expression Vectors

Provided herein are expression vectors comprising a nucleic acid operably linked to a promoter. The nucleic acids encoding the different elements of the vector can each be operably linked to the same or different promoters. Exemplary promoters include, but are not limited to, the CMV promoter, ubiquitin promoter, PGK promoter, and EF1 also promoter. Optionally, provided herein are expression vectors comprising a nucleic acid having SEQ ID NO:1 or a nucleic acid with 90%, 91%, 92%, 93%, 94%, 95%, 96%, 97%, 98% or 99% identity to SEQ ID NO:1. Optionally, the nucleic acid is operably linked to a promoter. Optionally, the promoter is selected from the group consisting of SEQ ID NOs:3, 9, 10 or 11 or a promoter having 90%, 91%, 92%, 93%, 94%, 95%, 96%, 97%, 98% or 99% identity to SEQ ID NOs:3, 9, 10 or 11. Optionally, the nucleic acid is operably linked to a promoter. Optionally, the promoter comprises SEQ ID NO:4 and/or SEQ ID NO:5. Optionally, the promoter comprises SEQ ID NO:6 or a nucleic acid with 90%, 91%, 92%, 93%, 94%, 95%, 96%, 97%, 98% or 99% identity to SEQ ID NO:6.

In some embodiments, the provided expression vector comprises SEQ ID NO:1 or a nucleic acid with 90%, 91%, 92%, 93%, 94%, 95%, 96%, 97%, 98% or 99% identity to SEQ ID NO:1; SEQ ID NO:25 (CD19 CAR) or a nucleic acid with 90%, 91%, 92%, 93%, 94%, 95%, 96%, 97%, 98% or 99% identity to SEQ ID NO:13 (CD16 158V), or a nucleic acid or polypeptide sequence with 90%, 91%, 92%, 93%, 94%, 95%, 96%, 97%, 98% or 99% identity to SEQ ID NO:14 (erIL-2 n.t. sequence); and/or SEQ ID NO:15 (erIL-2 a.a. sequence), or a nucleic acid with 90%, 91%, 92%, 93%, 94%, 95%, 96%, 97%, 98% or 99% identity to SEQ ID NO:14. In some embodiments, the provided expression vector comprises SEQ ID NO:47 (CXCR2) or a nucleic acid with 90%, 91%, 92%, 93%, 94%, 95%, 96%, 97%, 98% or 99% identity to SEQ ID NO:47; SEQ ID NO:25 (CD19 CAR) or a nucleic acid with 90%, 91%, 92%, 93%, 94%, 95%, 96%, 97%, 98% or 99% identity to SEQ ID NO:12; and SEQ ID NO:13 (CD16 158V), and/or a nucleic acid with 90%, 91%, 92%, 93%, 94%, 95%, 96%, 97%, 98% or 99% identity to SEQ ID NO:14; and/or SEQ ID NO:15 (erIL-2), or a nucleic acid with 90%, 91%, 92%, 93%, 94%, 95%, 96%, 97%, 98% or 99% identity to SEQ ID NO:14. Suitable expression vectors are known in the art and can be used. In further aspects, the recombinant nucleic acid comprises a segment encoding erIL-15, and the nucleic acid encoding erIL-15 has at least 90%, 91%, 92%, 93%, 94%, 95%, 96%, 97%, 98% or 99% identity to SEQ ID NO:67. Optionally, the expression vector is a plasmid.

The expression analysis of PD-L1 CAR and CD-16 in PD-L1 (TGFβ-trap) t-haNK cells are illustrated in FIG. 22. Moreover as illustrated in FIG. 23, TGFβ-trap is secreted into the culture supernatant of TGFβ-trap/PD-L1 t-haNK cells. Similarly, IL-12 secretion from IL-12 virally transduced NK-92® cell lines are shown in FIG. 30, right column.

Methods of Making Modified Nk-92® Cells

Provided herein are methods of making modified NK-92® cells comprising the nucleic acid molecules described herein. The methods include transforming NK-92® cells with an expression vector comprising a nucleic acid described herein operably linked to a promoter.

As used herein, the terms promoter, promoter element, and regulatory sequence refer to a polynucleotide that regulates expression of a selected polynucleotide sequence operably linked to the promoter, and that effects expression of the selected polynucleotide sequence in cells. In some embodiments, a promoter element is or comprises untranslated regions (UTR) in a position 5' of coding sequences. 5' UTRs form part of the mRNA transcript and so are an integral part of protein expression in eukaryotic organisms. Following transcription 5'UTRs can regulate protein expression at both the transcription and translation levels. Promoters controlling transcription from vectors in mammalian host cells may be obtained from various sources, for example, the genomes of viruses such as polyoma, Simian Virus 40 (SV40), adenovirus, retroviruses, hepatitis B virus and cytomegalovirus (e.g., SEQ ID NO:11), or from heterologous mammalian promoters, e.g. beta actin promoter, Eukaryotic translation elongation factor 1 alpha 1 (EF1α) promoter (e.g., SEQ ID NO:3), phosphoglycerate kinase (PGK) promoter (e.g., SEQ ID NO:10) and ubiquitin promoter (e.g., SEQ ID NO:9). Provided herein are promoters having 90%, 91%, 92%, 93%, 94%, 95%, 96%, 97%, 98% or 99% identity to SEQ ID NOs:3, 9, 10 or 11.

The phrase selectable marker, as used herein, refers either to a nucleotide sequence, e.g., a gene, that encodes a product (polypeptide) that allows for selection, or to the gene product (e.g., polypeptide) itself. The term selectable marker is used herein as it is generally understood in the art and refers to a marker whose presence within a cell or organism confers a significant growth or survival advantage or disadvantage on the cell or organism under certain defined culture conditions (selective conditions). The phrase selection agent, as used herein refers to an agent that introduces a selective pressure on a cell or populations of cells either in favor of or against the cell or population of cells that bear a selectable marker. For example, the selection agent is an antibiotic and the selectable marker is an antibiotic resistance gene. Examples of suitable selectable markers for mammalian cells are dihydrofolate reductase (DHFR), thymidine kinase, neomycin, neomycin analog G418, hydromycin, and puromycin.

Nucleic acid, as used herein, refers to deoxyribonucleotides or ribonucleotides and polymers and complements thereof. The term includes deoxyribonucleotides or ribonucleotides in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, conservatively modified variants of nucleic acid sequences (e.g., degenerate codon substitutions) and complementary sequences can be used in place of a particular nucleic acid sequence recited herein. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A nucleic acid is operably linked when it is placed into a functional relationship with another nucleic acid sequence. For example, DNA that encodes a presequence or secretory leader is operably linked to DNA that encodes a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are near each other, and, in the case of a secretory leader, contiguous and in reading phase. However, enhancers do not have to be contiguous. For example, a nucleic acid sequence that is operably linked to a second nucleic acid sequence is covalently linked, either directly or indirectly, to such second sequence, although any effective three-dimensional association is acceptable. A single nucleic acid sequence can be operably linked to multiple other sequences. For example, a single promoter can direct transcription of multiple RNA species. Linking can be accomplished by ligation at convenient restriction sites. If such sites do not exist, the synthetic oligonucleotide adaptors or linkers are used in accordance with conventional practice.

Methods of Treatment

Described herein are methods of treating cancer or a tumor in a subject. As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms subject, patient, individual, etc. are not intended to be limiting and can be generally interchanged. That is, an individual described as a patient does not necessarily have a given disease, but may be merely seeking medical advice. As used throughout, a subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient, individual and subject may be used interchangeably and these terms are not intended to be limiting. That is, an individual described as a patient does not necessarily have a given disease, but may be merely seeking medical advice. The terms patient or subject include human and veterinary subjects.

"Administration" or "administering," as used herein, refers to providing, contacting, and/or delivering a compound or compounds by any appropriate route to achieve the desired effect. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional or intracranial injection), transdermal, topical, buccal, rectal, vaginal, nasal, ophthalmic, via inhalation, and implants. Optionally, the NK-92® cells are administered parenterally. Optionally, the NK-92® cells are administered intravenously. Optionally, the NK-92® cells are administered peritumorally.

Thus, provided herein are methods of reducing cancer metastasis in a subject comprising administering to the subject a therapeutically effective amount of modified NK-92® cells described herein, thereby reducing cancer metastasis in the subject. Also provided are methods of treating cancer in a subject, which include the steps of selecting a subject having cancer and administering to the subject a therapeutically effective amount of modified NK-92® cells described herein, wherein administration treats the cancer in the subject. Optionally, the methods further include administering to the subject an additional therapeutic agent.

In some embodiments, the methods further comprise administering to a subject a therapeutically effective amount of the modified NK-92® cells described herein, wherein administration treats the cancer or reduces the size of a tumor in the subject. In some embodiments, the methods comprise administering to the subject modified NK-92® cells that comprise a nucleic acid encoding i) IL-12 or TGFb trap, ii) an ABP or CAR that specifically binds to a target antigen, iii) an Fc Receptor such as CD16 or CD16-158V, and/or iv) a cytokine such as erIL-2 or erIL-15. In some embodiments, the methods comprise administering to the subject modified NK-92® cells that comprise a nucleic acid encoding i) a homing receptor, ii) an ABP or CAR that specifically binds to a target antigen, iii) an Fc Receptor such as CD16 or CD16-158V, and/or iv) a cytokine such as erIL-2 or erIL-15.

The cytotoxicity of TGFβ-trap/PD-L1 against K562 target cells are illustrated in FIG. 24. Furthermore, CAR killing against SUP-B15$^{PD-L1+}$ target cells are showin in FIG. 25, while CAR killing against MDA-MB 231 target cells are showin in FIG. 26. ADCC of TGFβ-trap/PD-L1 against SUP-B15$^{CD19-CD20+}$ is illustrated in FIG. 27. FIG. 28 illustrates TGFβ/SMAD Luciferase reporter HEK293 cells are induced by TGFβ. Secreted TGFβ-trap sequestered TGFβ and inhibited luciferase expression in HEK293T reporter assay as shown in FIG. 29. Reporter cells were treated with 1 ng/mL TGFβ1 for 19 hours. Among other options, preferred CAR molecules specifically bind PD-L1, and may have an amino acid sequence at least 90%, 91%, 92%, 93%, 94%, 95%, 96%, 97%, 98% or 99% identical to SEQ ID NO:69 (which may be encoded by a nucleic acid sequence at least 90%, 91%, 92%, 93%, 94%, 95%, 96%, 97%, 98% or 99% identical to SEQ ID NO:68.

The NK-92® cells may be administered to the subject by a variety of routes. For example, the NK-92® cells can be administered to the subject by infusion (e.g., intravenous infusion) over a period of time. Typically, for a single dose of NK-92® cells, the period of time is between 5 and 130 minutes. Optionally, the period of time is between 90 and 120 minutes. Optionally, the period of time is between 15 to 30 minutes.

The NK-92® cells, and optionally other anti-cancer agents can be administered once to a patient with cancer can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive. Thus, for example, NK-92® cells can be administered to the subject once daily for 1, 2, 3, 4, 5, 6, 7, 8, 9, 10, 11, 12, 13, 14, 15, 16, 17, 18, 19, 20 or more days. Optionally, the NK-92® cells are administered in a cycle of once daily for two days. The cycle is then followed by one or more hours, days, or weeks of no treatment with NK-92® cells. As used herein, the term "cycle" refers to a treatment that is repeated on a regular schedule with periods of rest (e.g., no treatment or treatment with other agents) in between. For example, treatment given for one week followed by two weeks of rest is one treatment cycle. Such cycles of treatment can be repeated one or more times. Thus, the NK-92® cells can be administered in 1, 2, 3, 4, 5, 6, 7, 8, 9, 10, 11, 12, 13, 14, 15, 16, 17, 18, 19, 20 or more cycles.

NK-92® cells can be administered to a subject by absolute numbers of cells, e.g., said subject can be administered from about 1000 cells/injection to up to about 10 billion cells/injection, such as at about, at least about, or at most about, $1\times10^{10}$, $1\times10^9$, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK-92® cells per injection, or any ranges between any two of the numbers, end points inclusive. Optionally, from $1\times10^8$ to $1\times10^{10}$ cells are administered to the subject. Optionally, the cells are administered one or more times weekly for one or more weeks. Optionally, the cells are administered once or twice weekly for 1, 2, 3, 4, 5, 6, 7, 8, 9, 10 or more weeks.

Optionally, subject are administered from about 1000 cells/injection/m$^2$ to up to about 10 billion cells/injection/m$^2$, such as at about, at least about, or at most about, $1\times10^{10}$/m$^2$, $1\times10^9$/m$^2$, $1\times10^8$/m$^2$, $1\times10^7$/m$^2$, $5\times10^7$/m$^2$, $1\times10^6$/m$^2$, $5\times10^6$/m$^2$, $1\times10^5$/m$^2$, $5\times10^5$/m$^2$, $1\times10^4$/m$^2$, $5\times10^4$/m$^2$, $1\times10^3$/m$^2$, $5\times10^3$/m$^2$ (and so forth) NK-92® cells per injection, or any ranges between any two of the numbers, end points inclusive. Optionally, from $1\times10^3$ to $1\times10^{10}$, per m$^2$ of the NK-92® cells are administered to the subject. Optionally, $2\times10^9$ per m$^2$, of the NK-92® cells are administered to the subject.

Optionally, NK-92® cells can be administered to such individual by relative numbers of cells, e.g., said individual can be administered about 1000 cells to up to about 10 billion cells per kilogram of the individual, such as at about, at least about, or at most about, $1\times10^{10}$, $1\times10^9$, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK-92® cells per kilogram of the individual, or any ranges between any two of the numbers, end points inclusive.

Optionally, the total dose may calculated by m$^2$ of body surface area, including about $1\times10"$, $1\times10^{10}$, $1\times10^9$, $1\times10^8$, $1\times10^7$, per m$^2$, or any ranges between any two of the numbers, end points inclusive. Optionally, between about 1 billion and about 3 billion NK-92® cells are administered to a patient. Optionally, the amount of NK-92® cells injected per dose may calculated by m2 of body surface area, including $1\times10"$, $1\times10^{10}$, $1\times10^9$, $1\times10^8$, $1\times10^7$, $1\times10^6$, $1\times10^5$, $1\times10^4$, $1\times10^3$, per m$^2$.

Optionally, NK-92® cells are administered in a composition comprising NK-92® cells and a medium, such as human serum or an equivalent thereof. Optionally, the medium comprises human serum albumin. Optionally, the medium comprises human plasma. Optionally, the medium comprises about 1% to about 15% human serum or human serum equivalent. Optionally, the medium comprises about 1% to about 10% human serum or human serum equivalent. Optionally, the medium comprises about 1% to about 5% human serum or human serum equivalent. Optionally, the medium comprises about 2.5% human serum or human serum equivalent. Optionally, the serum is human AB serum. Optionally, a serum substitute that is acceptable for use in human therapeutics is used instead of human serum. Such serum substitutes may be known in the art. Optionally, NK-92® cells are administered in a composition comprising NK-92® cells and an isotonic liquid solution that supports cell viability. Optionally, NK-92® cells are administered in a composition that has been reconstituted from a cryopreserved sample.

According to the methods provided herein, the subject is administered an effective amount of one or more of the agents provided herein. The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 22nd Edition, Gennaro, Editor (2012), and Pickar, Dosage Calculations (1999)).

Pharmaceutically acceptable compositions can include a variety of carriers and excipients. A variety of aqueous carriers can be used, e.g., buffered saline and the like. These solutions are sterile and generally free of undesirable matter. Suitable carriers and their formulations are described in *Remington: The Science and Practice of Pharmacy, 22nd Edition*, Loyd V. Allen et al., editors, Pharmaceutical Press (2012). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. As used herein, the term pharmaceutically acceptable is used synonymously with physiologically acceptable and pharmacologically acceptable. A pharmaceutical composition will generally comprise agents for buffering and preservation in storage and can include buffers and carriers for appropriate delivery, depending on the route of administration.

The compositions may contain acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of cells in these formulations and/or other agents can vary and will be selected primarily based on fluid volumes, viscosities, body weight and the like in accordance with the particular mode of administration selected and the subject's needs.

Combination Therapies

Optionally, the NK-92® cells are administered to the subject in conjunction with one or more other treatments for the cancer being treated. Without being bound by theory, it is believed that co-treatment of a subject with NK-92® cells and another therapy for the cancer will allow the NK-92® cells and the alternative therapy to give the endogenous immune system a chance to clear the cancer that heretofore had overwhelmed such endogenous action. Optionally, two or more other treatments for the cancer being treated includes, for example, an antibody, a bi-specific engager, radiation, chemotherapeutic, stem cell transplantation, or hormone therapy.

Optionally, an antibody is administered to the patient in conjunction with the NK-92® cells. Optionally, the NK-92® cells and an antibody are administered to the subject together, e.g., in the same formulation; separately, e.g., in separate formulations, concurrently; or can be administered separately, e.g., on different dosing schedules or at different times of the day. When administered separately, the antibody can be administered in any suitable route, such as intravenous or oral administration.

Optionally, antibodies may be used to target cancerous cells or cells that express cancer-associated markers. A number of antibodies have been approved for the treatment of cancer, alone.

The provided methods may be further combined with other tumor therapies such as radiotherapy, surgery, hormone therapy and/or immunotherapy. Thus, the provided methods can further include administering one or more additional therapeutic agents to the subject. Suitable additional therapeutic agents include, but are not limited to, analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated. Optionally, the additional therapeutic agent is octreotide acetate, interferon, pembrolizumab, glucopyranosyl lipid A, carboplatin, etoposide, or any combination thereof.

Optionally, the additional therapeutic agent is a chemotherapeutic agent. A chemotherapeutic treatment regimen can include administration to a subject of one chemotherapeutic agent or a combination of chemotherapeutic agents. Chemotherapeutic agents include, but are not limited to, alkylating agents, anthracyclines, taxanes, epothilones, histone deacetylase inhibitors, inhibitors of Topoisomerase I, inhibitors of Topoisomerase II, kinase inhibitors, monoclonal antibodies, nucleotide analogs and precursor analogs, peptide antibiotics, platinum-based compounds, retinoids, and *vinca* alkaloids and derivatives. Optionally, the chemotherapeutic agent is carboplatin.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous, or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly, or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

Kits

Provided herein are kits comprising the modified NK-92® cells described herein. In some embodiments, the kit comprises modified NK-92® cells comprising one or more nucleic acid sequences encoding i) a homing receptor, ii) an ABP or CAR that specifically binds to a target antigen, iii) an Fc Receptor such as CD16 or CD16-158V, and/or iv) a cytokine such as erIL-2, operably linked to a promoter. Optionally, one or more proteins encoded by the nucleic acid sequences are expressed on the cell surface of the modified NK-92® cells. In some embodiments, kit comprises a modified NK-92® cell comprising a nucleic acid encoding C-C chemokine receptor type 7 (CCR7), CXCR2, or the receptor for CXCL14 operably linked to a promoter. Optionally, the nucleic acid encoding CCR7 has at least 90%, 91%, 92%, 93%, 94%, 95%, 96%, 97%, 98% or 99% identity to SEQ ID NO:1. Optionally, the homing receptor is expressed on the cell surface of the modified NK-92® cells. Optionally, the promoter comprises one or more NFAT binding elements and a minimal promoter. Optionally, the promoter has at least 90%, 91%, 92%, 93%, 94%, 95%, 96%, 97%, 98% or 99% identity to SEQ ID NO:6. Optionally, one or more proteins encoded by the nucleic acid sequences are expressed on the cell surface of the modified NK-92® cells.

Optionally, the modified NK-92® cells are provided in a composition comprising a pharmaceutically acceptable excipient. Optionally, the kit may contain additional compounds such as therapeutically active compounds or drugs that are to be administered before, at the same time or after administration of the modified NK-92® cells. Optionally, instructions for use of the kits will include directions to use the kit components in the treatment of a cancer. The instructions may further contain information regarding how to prepare (e.g., dilute or reconstitute, in the case of freeze-dried protein) the antibody and the NK-92® cells (e.g., thawing and/or culturing). The instructions may further include guidance regarding the dosage and frequency of administration.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed while, specific references to each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the materials for which they are cited are hereby specifically incorporated by reference in their entireties.

The examples below are intended to further illustrate certain aspects of the methods and compositions described herein, and are not intended to limit the scope of the claims.

EXAMPLES

Figure 1:
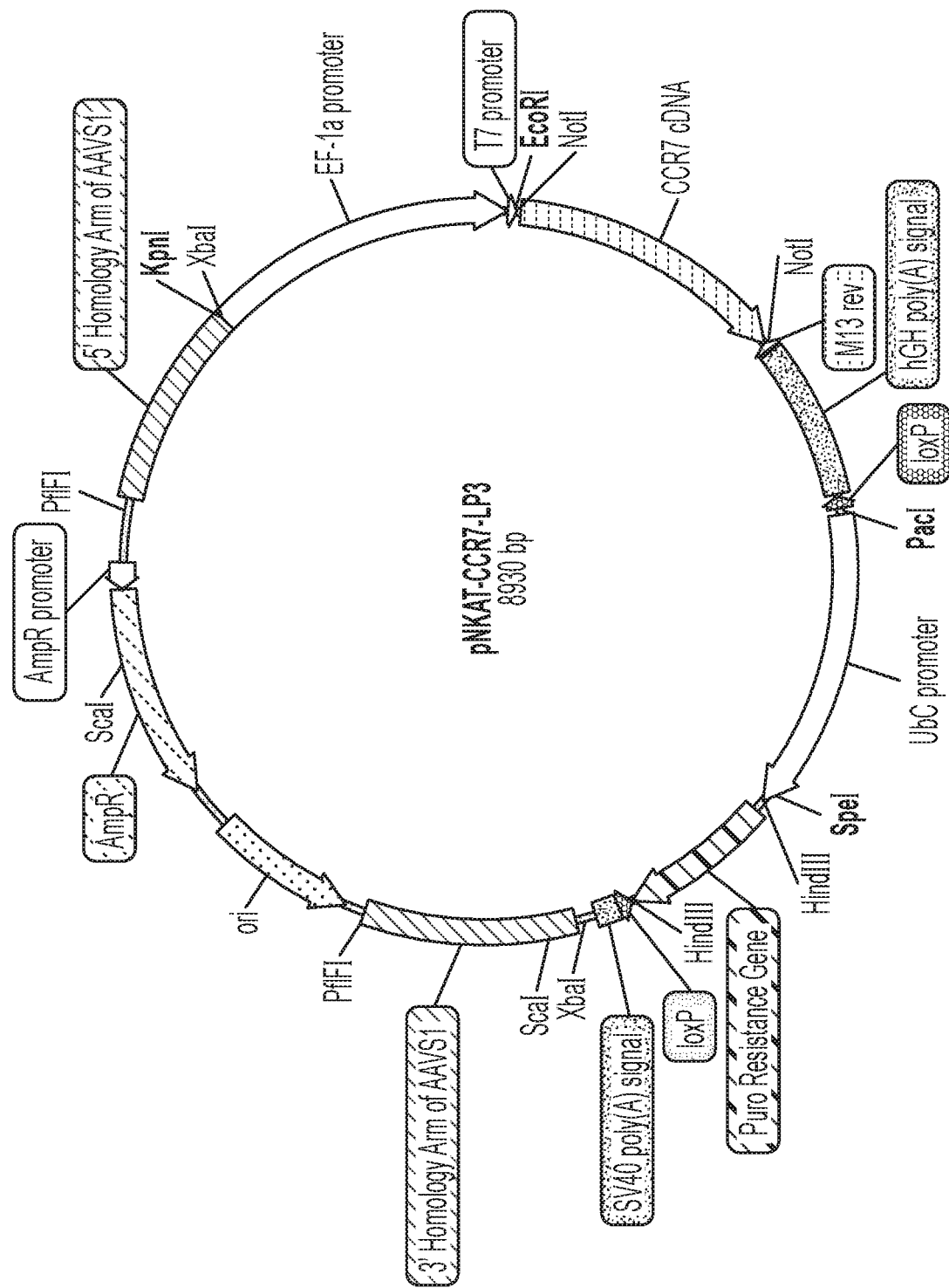
FIG. 1 is a schematic showing plasmid pNKAT-CCR7-LP3 containing the CCR7 receptor for insertion at the AAVS1 locus in NK-92® cells.
Figure 2:
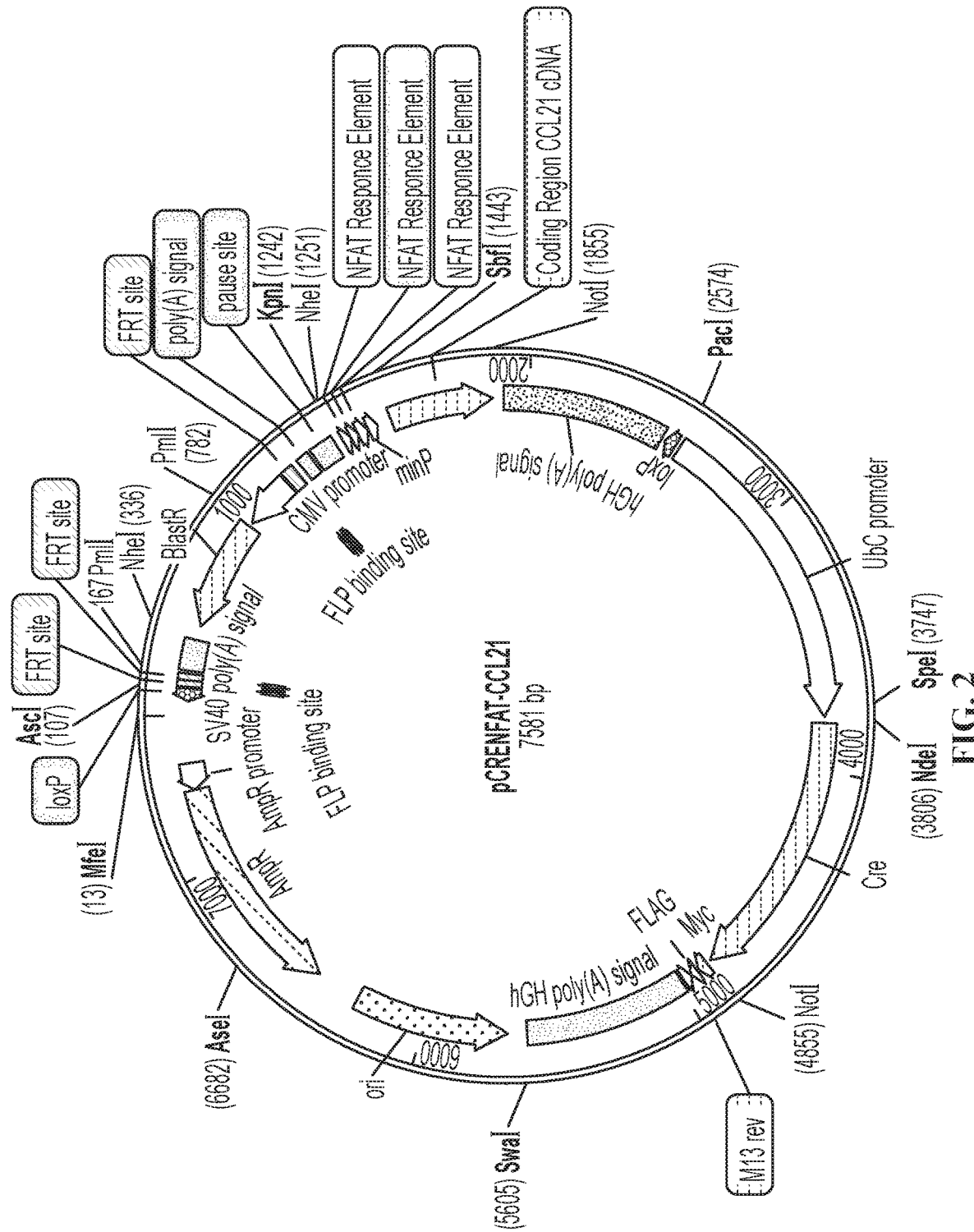
FIG. 2 is a schematic showing plasmid pCRENFAT-CCL21 containing a NFAT-responsive CCL21 gene.

Example 1. Modified NK Cell Line Expressing CCR7, a Cytokine that Modulates the Tumor Microenvironment Modified NK-92® cells were made by electroporation with a linearized pNKAT-CCR7-LP3 plasmid (FIG. 1) using a NEON transfection system (Thermo Fisher Scientific, Waltham, Mass.) on NK-92® cells. After 1 week of puromycin selection, the resulting polyclonal population was tested for CCR7 expression, and monoclonal cell lines were derived by serial dilution in growth media supplemented with 5% human serum and IL-2. The modified NK-92® cells contained the EF1α promoter, CCR7 Gene with Poly-Atail, and the LoxP flanked puromycin resistance gene driven by the ubiquitin promoter all encased in homology arms targeting the AAVS1 locus (SEQ ID NO:7).

Figure 3:
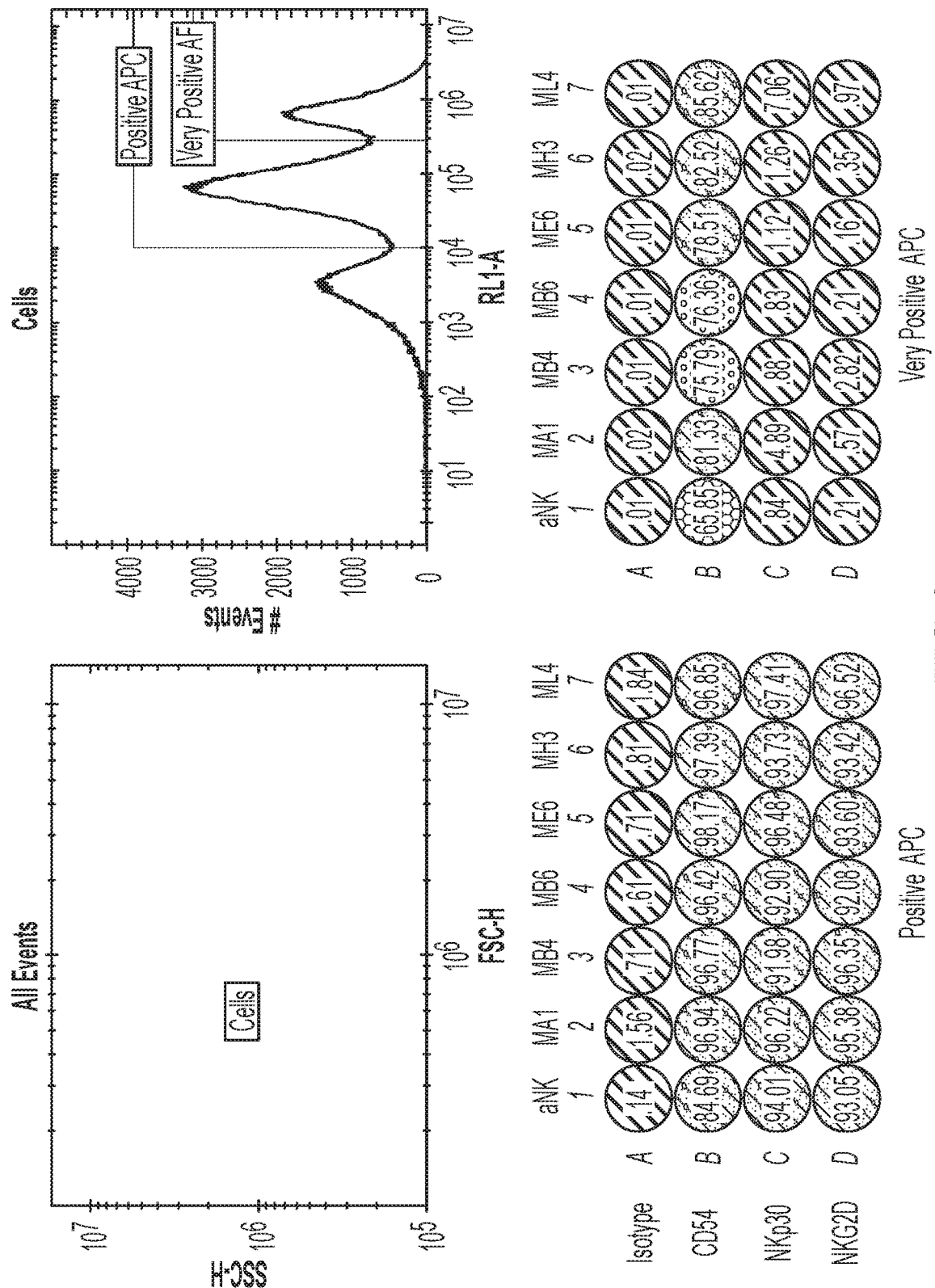
FIG. 3 are graphs showing expression of phenotypic markers associated with NK-92® cells in wild type NK-92® cells and modified NK-92® cells expressing CCR7. (Lane 1: aNK (Wild Type); Lane 2: Modified NK-92® cells (MA3); Lane 3: Modified NK-92® cells (MB4); Lane 4: Modified NK-92® cells (MB6); Lane 5: Modified NK-92® cells (ME6); Lane 6: Modified NK-92® cells (MH3); A: Isotype (APC); B: CD54 (ICAM-1); C: NKp30; D: NKG2D FIG. 4 is a graph showing cytoxic activity of modified NK-92® cells expressing CCR7 against K562 cells.

To verify expression of CCR7 does not affect NK-92® cells, expression of markers of NK-92® cells was determined. The results are shown in FIG. 3. All data in FIG. 3 was generated using an Intellicyt iQue screener plus. Cells were incubated at 4° C. for 30 minutes with either APC conjugated antibody against the described phenotypic marker, or appropriate isotype as negative control. Cells were then rinsed in PBS+1% BSA, pelleted, and re-suspended in 30 uL of PBS+1% BSA. The readout was then gated as shown in the upper left quadrant to eliminate cellular debris from the readings, and the percentage of cells above the fluorescence thresholds shown in the upper right quadrant were then displayed as two separate heatmaps, showing the percentage above the "positive" threshold, and the "very positive" threshold in the lower left and lower right quadrants respectively. FIG. 3 shows that driving expression of CCR7 does not meaningfully affect the primary phenotypic markers associated with our cell lines. Specifically, CCR7 expression does not appear to affect CD54, NKp30 or NKG2D expression.

Figure 4:
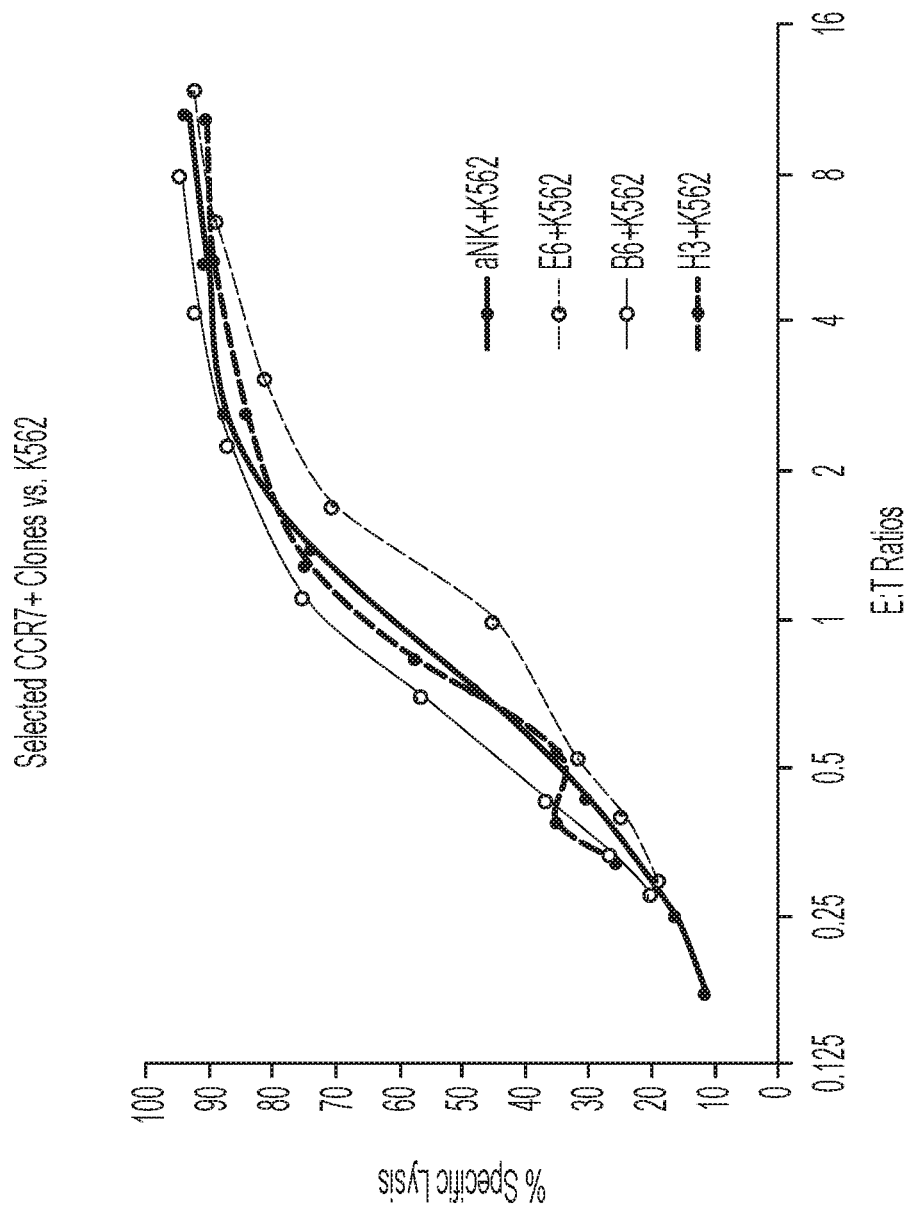
Figure 5:
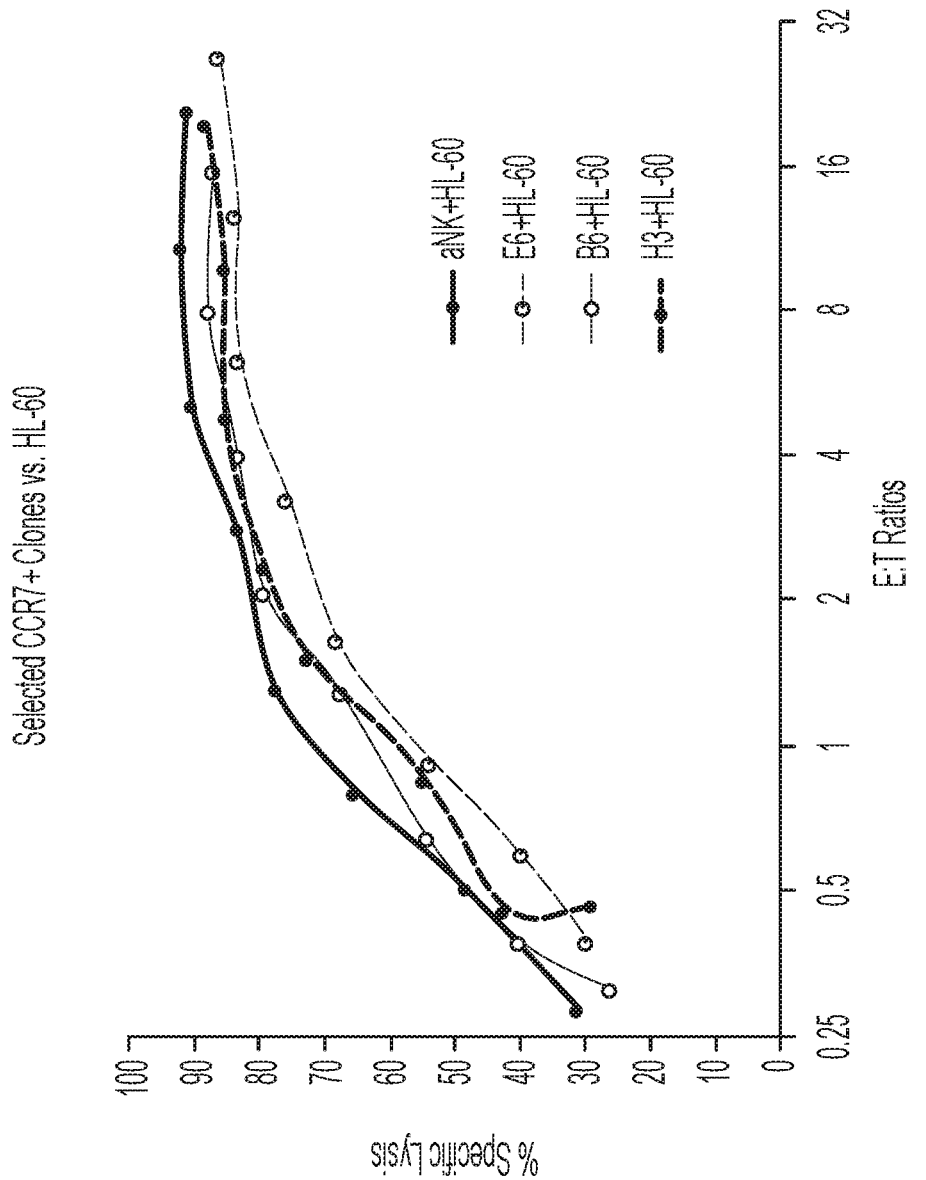
FIG. 5 is a graph showing cytoxic activity of modified NK-92® cells expressing CCR7 against HL-60 cells.

To determine cytotoxicity of the modified NK-92® cells, effector cells (NK-92® cells and modified NK-92® cell clones) were serially diluted in a 96-well V-bottom plate, with 100 k effectors left in the highest concentration well, and with 7 further 2-fold dilutions across the 8 rows of the plate. Stained target cells (K562 (FIG. 4), HL-60 (FIG. 5) were then seeded at 10 k/well in all wells containing effectors, along with control wells of just targets to measure background death. The plate was then briefly spun down and incubated at 37° C. and 5% $CO_2$ for 4 hours. The plate was then spun down, the supernatant aspirated off, and the cells re-suspended in PBS containing propidium iodide to measure cell death. The cells were then run through an Intellicyt iQue screener plus, and the proportion of target cells (differentiated from effectors by their stain) which are also positive for PI staining was measured. The percentage of dead cells was then compared against the number of naturally dying cells in the control wells, and a percentage of cells that are specifically killed by the effectors was calculated. The results are shown in FIGS. 4 and 5. FIG. 4 shows comparable cytotoxicity in CCR7 upregulated clones as compared to parental cell line vs. K562 cells and FIG. 5 shows comparable cytotoxicity in CCR7 upregulated clones as compared to parental cell line vs. HL-60 cells.

Figure 7:
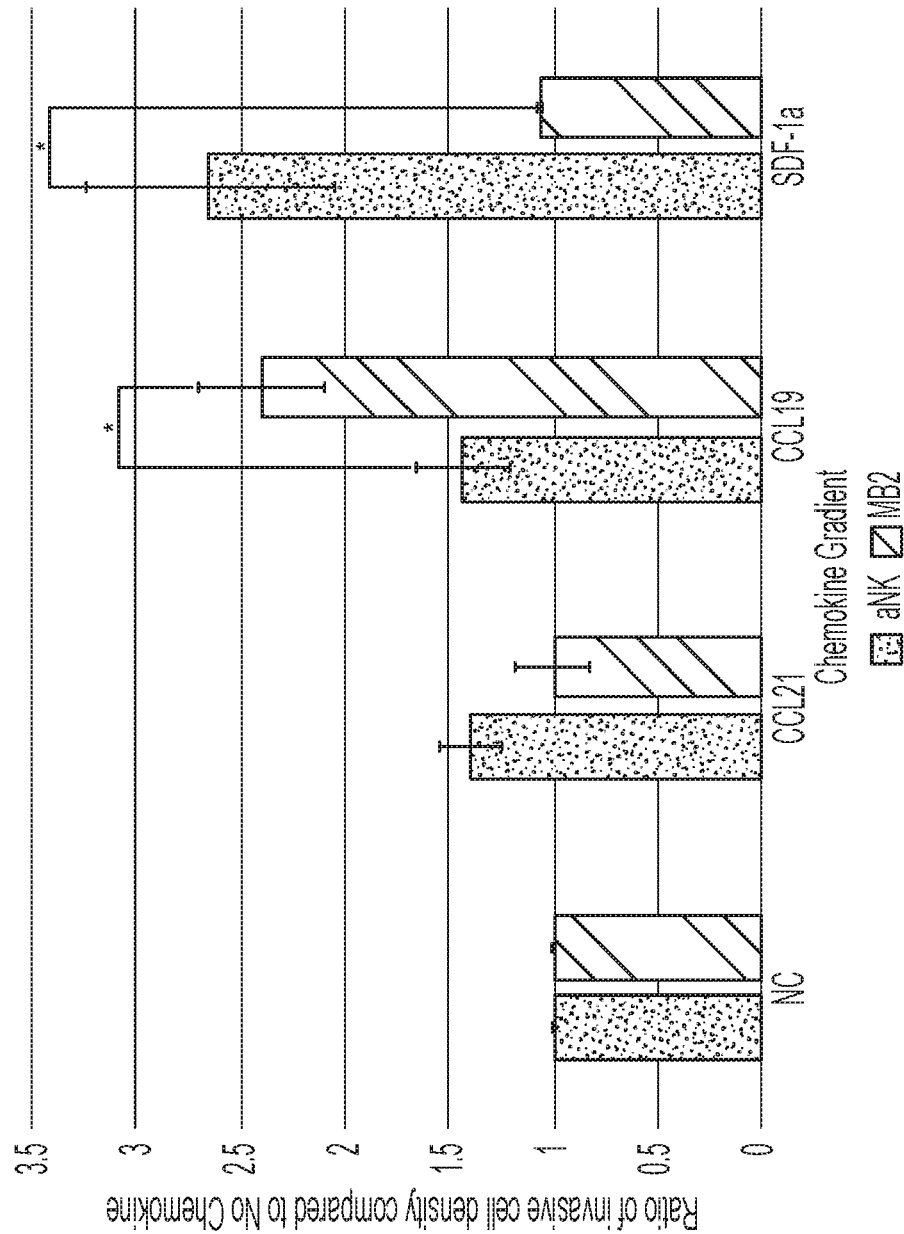
FIG. 7 is a graph showing modified NK-92® cells expressing CCR7 (Mi-aNK) migrated towards the chemokines CCL19 and CCL21.
Figure 8:
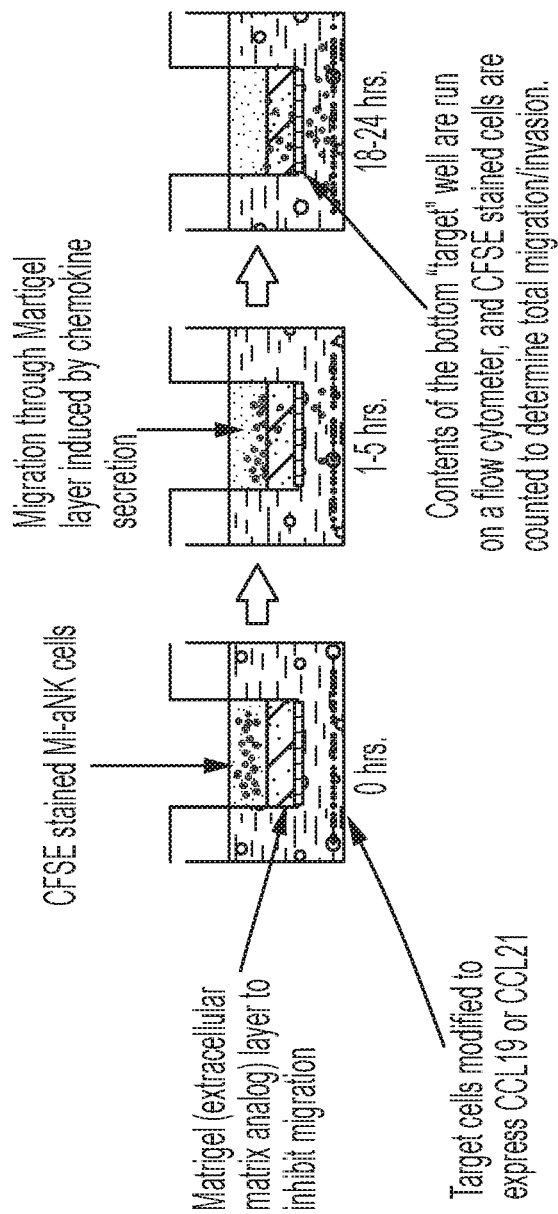
FIG. 8 shows a diagram representing an exemplary method for in vitro testing of the modified NK-92® cells described herein. Activated NK-92® cells (aNK) were modified to express a chemokine receptor (e.g., CCR7), and the target cells were modified to express a chemokine that binds to the receptor (e.g., CCL19 or CCL21). The modified NK-92® cells were tested in a Modified Boyden Chamber Transwell Assay as shown.

In vitro testing consisted of using Boyden chamber assays and a Matrigel layer to block migration. The modified cells expressing CCR7 showed migration towards CCL21 and CCL19 (an alternate CCR7 ligand) in these assays. Cells were placed in an upper well, and separated from a lower chamber by a thin layer of Matrigel (an ECM-like substrate) coated on 8 uM pores. The cells (25 k/well) were placed in the upper chamber, in reduced-serum media (supplemented with 1% Human Serum and 500 U/mL IL-2), and the same reduced serum medium was used in the lower chamber, either by itself or containing a chemokine of interest. In this case, CCL21 was used at 15 ng/mL, CCL19 was used at 15 ng/mL, and SDF-1a was used at 20 ng/mL. Each test was done in triplicate for either NK-92® cells or modified NK-92® cells expressing CCR7. The plate was then placed in the incubator overnight for an 18 hour invasion assay, after which the upper chambers were removed, and 150λ, (of 750λ, total volume) was sampled from the lower well after thorough mixing and read on a MacsQuant FACS analysis machine. Live cells in the lower chamber were counted, and the number of cells was then compared against the wells containing no chemokine and an invasiveness index number was generated. These numbers were averaged and statistical relevance calculated using a two-tailed t-test. As the lower well was sampled without any detachment of cells from the lower membrane, those cells still attached to the lower portion of the ECM would not be represented in these numbers, likely resulting in the differences between CCL19 and CCL21. The results are shown in FIG. 7. Specifically, FIG. 7 shows statistically significant increases in invasiveness of modified NK-92® cells expressing CCR7 towards CCL19, a CCR7 chemokine. The lack of a statistically significant response to CCL21 is likely due to the nature of the assay performed. The assay measures both invasion and subsequent detachment from the ECM, a behavior consistent with CCL19 gradient migration. CCL21, while inducing migration, does not induce detachment from the matrix, requiring an additional step to demonstrate statistically significant invasive potential.

Example 2. Generation of NFAT Responsive Construct for Controlled Expression of CCL21

Figure 6A:
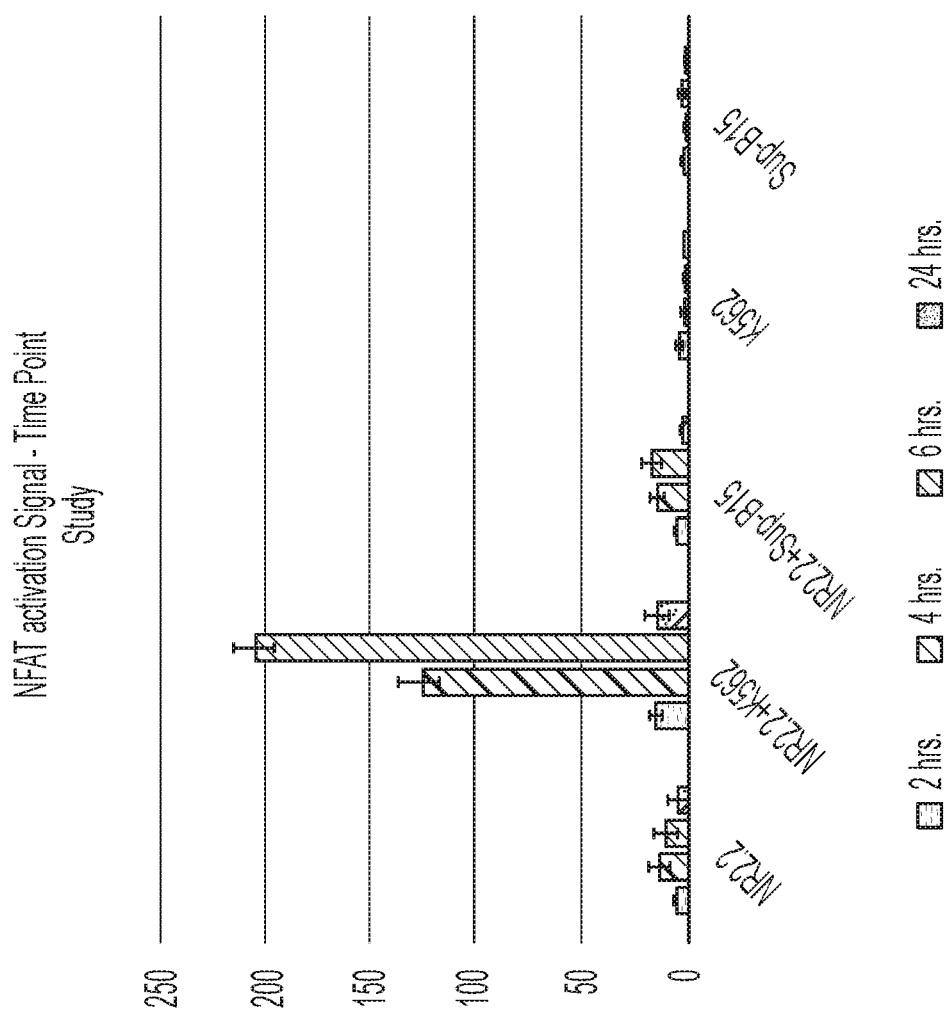
FIGS. 6A and 6B are graphs showing activation of an NFAT-Luciferase reporter gene in NK-92 cells demonstrated in the context of binding to K562 and SUP-B15 cells (when NK-92 cells were electroporated with mRNA for a CD19-CAR).
Figure 6B:
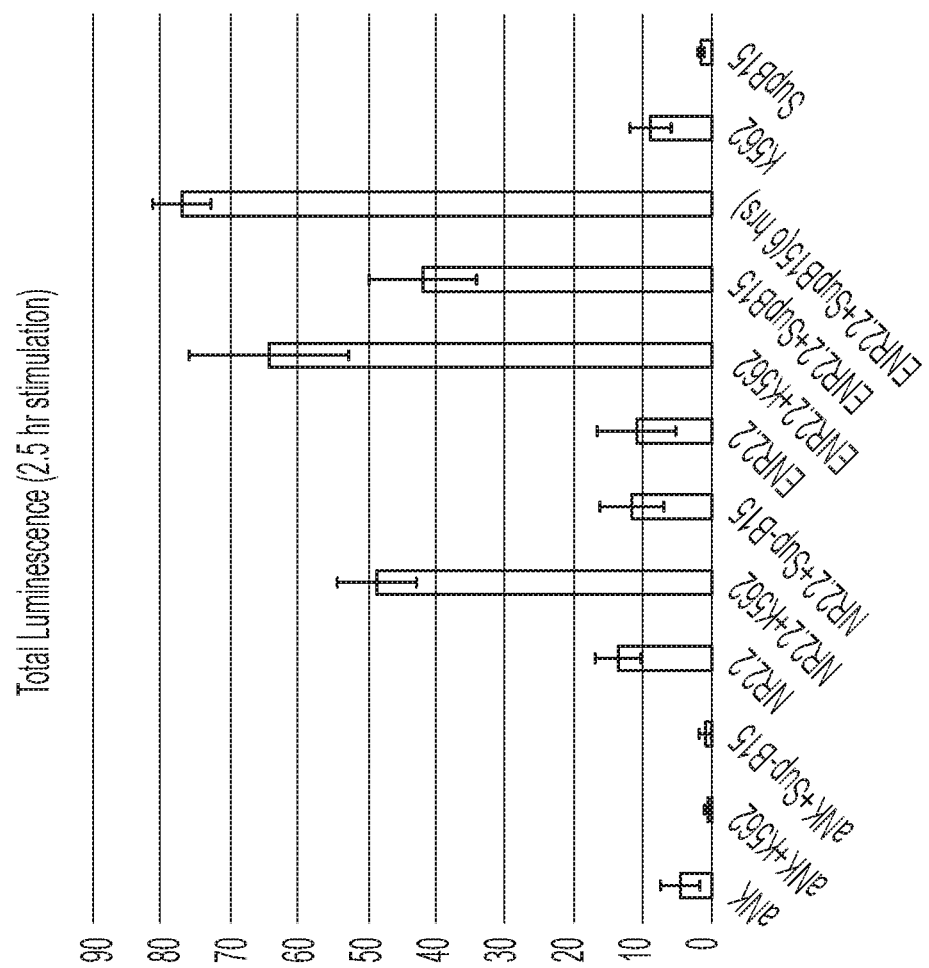

To identify an NFAT responsive element, a cell line stably expressing an NFAT-based Luciferase expression cassette (NR2.2) was created by electroporating a linearized construct into NK-92® cells which contains a stop region, followed by 3 NFAT response elements (SEQ ID NO:4), and a minimal promoter (SEQ ID NO:5), which in the presence of activated NFAT will thus drive the production of Firefly Luciferase. A subset of these cells were then also electroporated with mRNA containing an anti-CD19 CAR (an antigen present on Sup-B15 cells, otherwise resistant to killing by NK-92® cells). These cells are represented in the left graph as ENR2.2. The cells were then plated in triplicate in the absence or presence of target cells, and incubated for periods ranging from 2.5 hours to 24 hours. At the end of the incubation period, the Step 1 reagent from a Promega DualGlo system was added to the wells to activate luciferase (by providing its substrate, luciferin). The result was then read on a SpectraMax i3x plate reader, and presented as an average with standard deviation as calculated in Microsoft Excel. The results are shown in FIGS. 6A and 6B. NFAT activation was demonstrated in the context of target binding to K562 in a time-dependent manner and to Sup-B15 but only when electroporated with mRNA for a CD19-CAR.

Example 3. Modified NK Cell Line Expressing CCR7 and CCL21

The pCRENFAT-CCL21 plasmid is incorporated into the NK-92® cells containing CCR7 using the LoxP sites embedded in the pNKAT-CCR7-LP3 construct in a recombinase mediated cassette exchange. Following electroporation of the circular plasmid (pCRENFAT-CCL21), Cre Recombinase is transiently expressed mediating the exchange of the new LoxP-flanked cassette for the old selection cassette. Selection in Blasticidin is used to favor the incorporation of the new cassette, and monoclonal cell lines are sub-cloned from the resulting population in the same manner as previously described in Example 1 to obtain modified NK-92® cells expressing CCR7 and CCL21.

To evaluate Modified NK-92® cells expressing CCR7 and CCL21, unstained modified NK-92® cells are co-cultured in the lower well of a Boyden chamber with cells known to cause NFAT activation (K562 or other cell line) and stained modified NK-92® cells are placed in the upper chamber. If migration is demonstrated to be induced by co-culture with sensitive cell lines, then this system is working.

Example 4: In Vitro Cytotoxicity Assays Using Modified NK Cell Line Expressing CCR7

Figure 9:
FIG. 9 shows a representative cytotoxicity assay using the modified NK-92® cells described herein. The modified NK-92® cells from FIG. 8 were tested for cytotoxicity against K562 target cells that express and secrete one or both chemokine ligands. The ML4 clone showed the highest percentage of lysis of target cells, and the percentage was increased when the K562 target cells expressed both CCL19 and CCL21.
Figure 9:
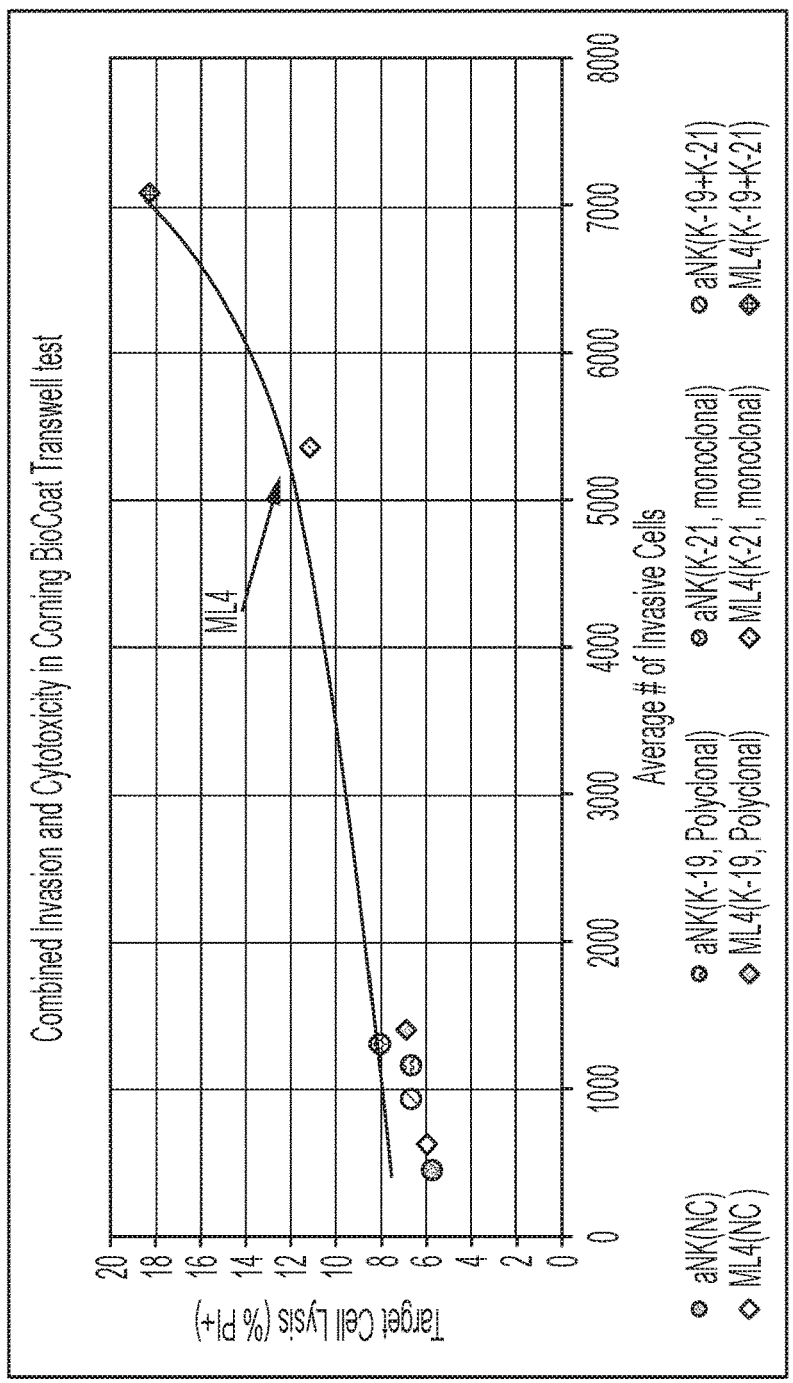
Figure 10:
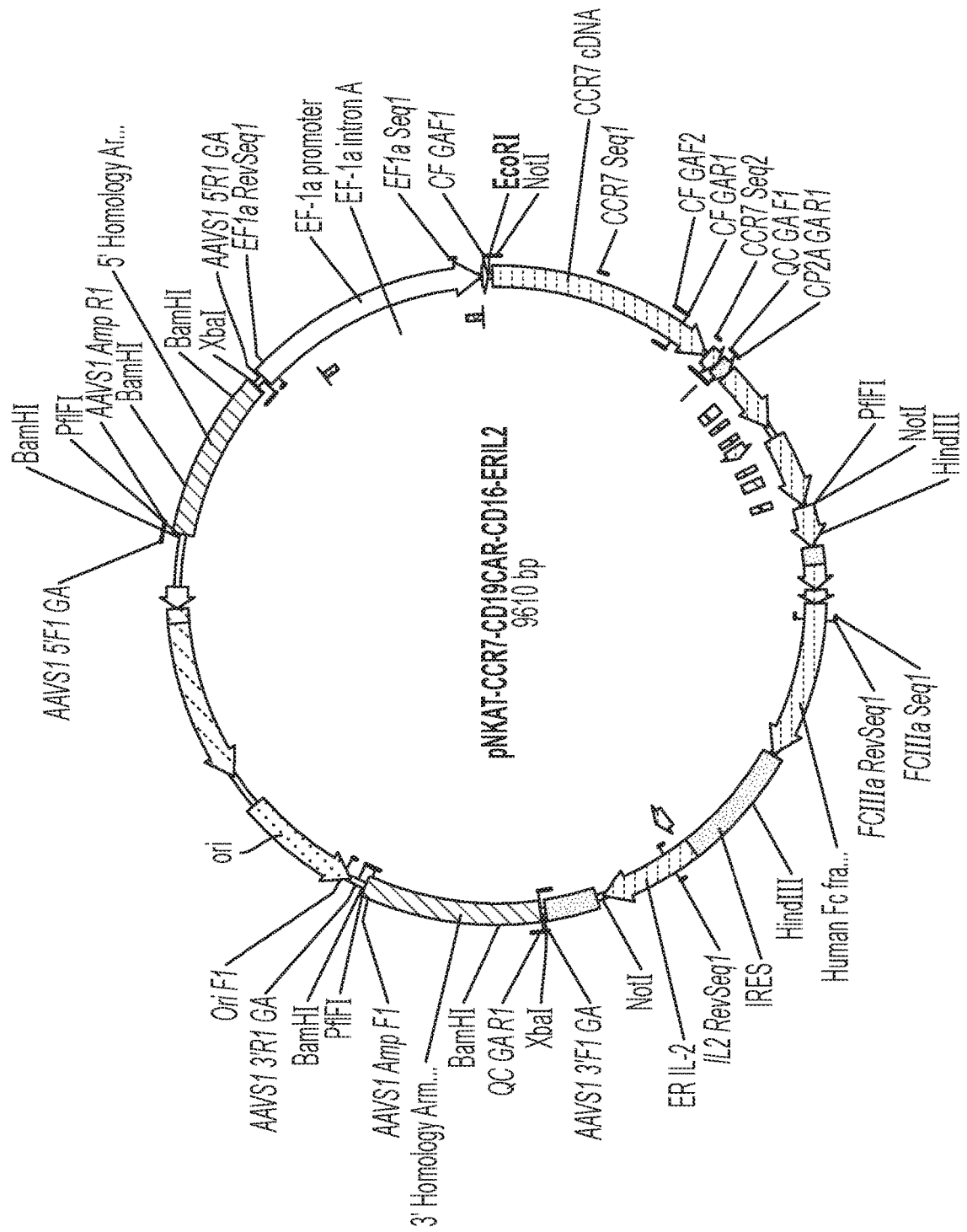
FIG. 10 is a schematic showing plasmid pNKAT-CCR7-CD19CAR-CD16-ERIL2, referred to as a "Quadricistronic Vector," which can be used to stably transfect a cell at a single insertion position.
Figure 11:
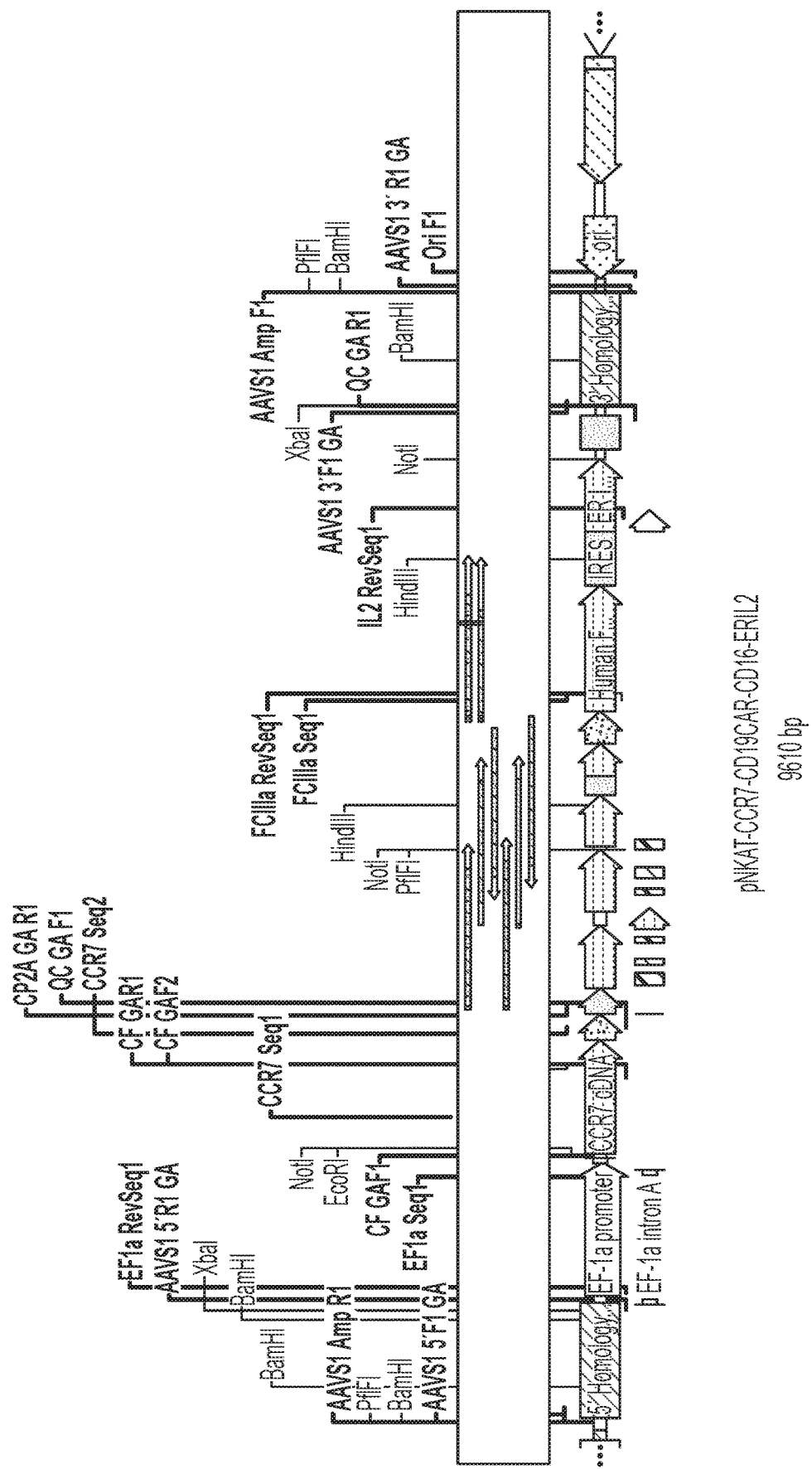
FIG. 11 is a schematic showing the linearized plasmid from FIG. 10.

FIG. 9 shows that NK-92® cells modified to express CCR7 maintain cytotoxicity to target cells after migration in a modified Boyden chamber transwell assay as described in Example 1.

Figure 12:
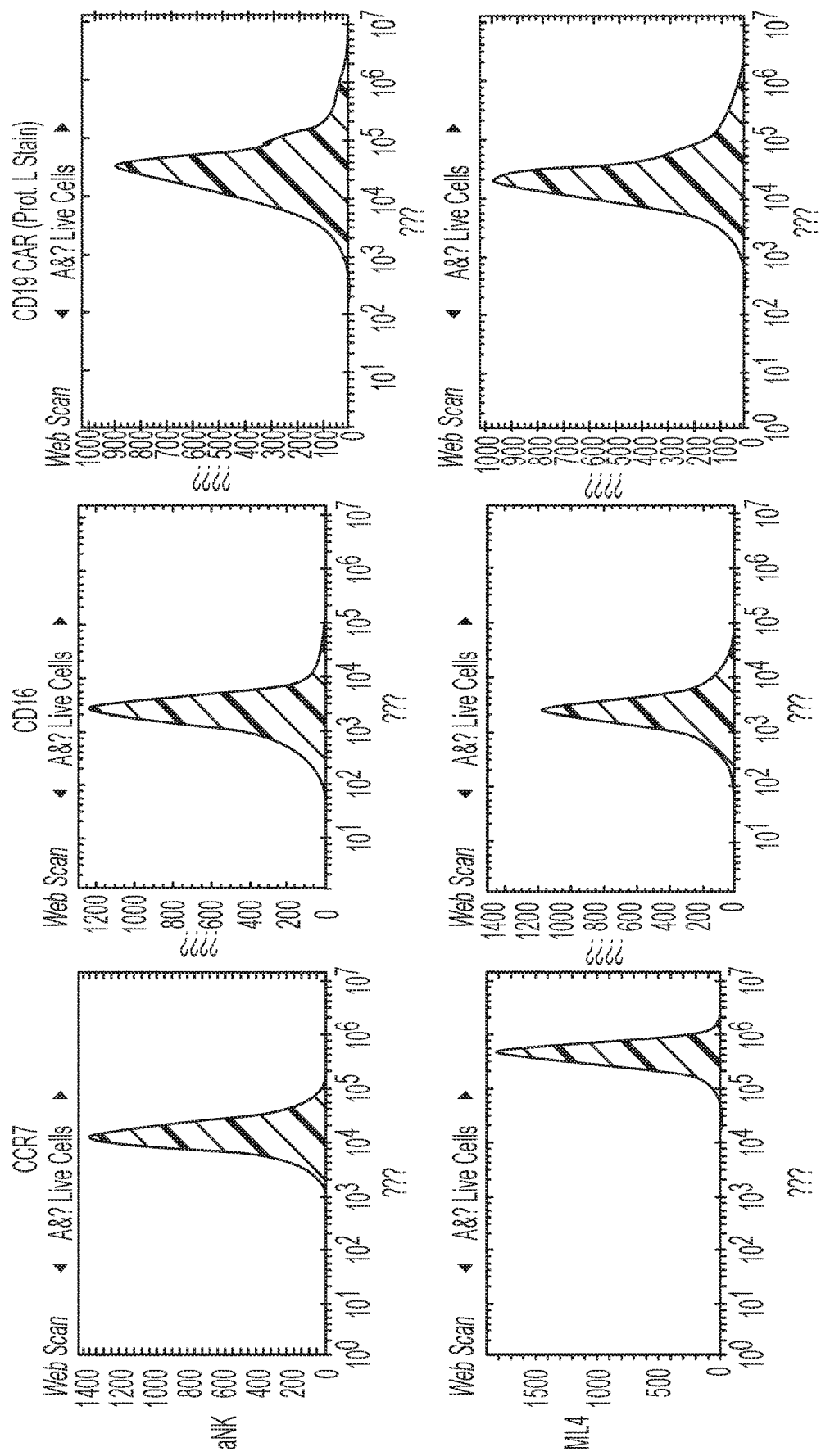
FIG. 12 shows cell surface expression of CCR7, CD16, and CD19 CAR by NK-92® cells. "aNK" is the wild-type NK-92® cell line. "ML4" is the aNK cell line transfected with a nucleic acid construct encoding CCR7 operably linked to a promoter (i.e. Mi-aNK). "P2" is the aNK cell line transfected with a nucleic acid construct that encodes CCR7, CD16, ER-IL2 and CD19 CAR (i.e. Mi- T-haNK).
Figure 12:
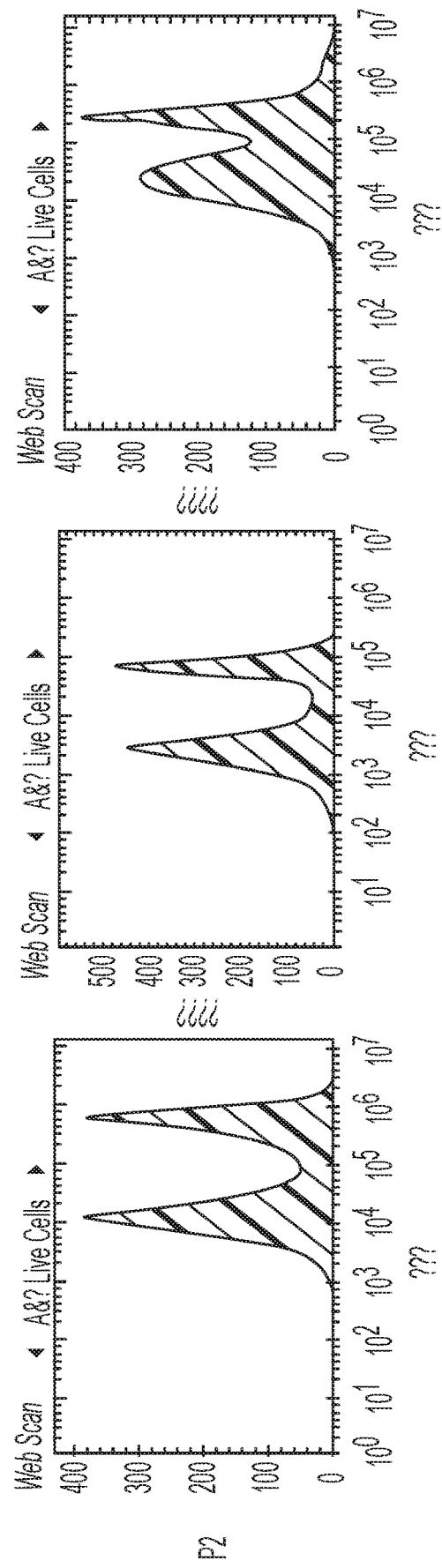

Example 5: Cell Surface Expression of CCR7, CD16, and CD19 Car in NK-92® Cells Transfected with Nucleic Acid Constructs FIG. 12 shows that modified NK-92® cells transfected with nucleic acid constructs encoding CCR7, CD16, and CD19 CAR express high levels of the respective proteins on the cell surface.

Example 6: Biodistribution of CCR7-Expressing Chemokine Responsive NK Cells in NSG Mice that Bear CCL19 Positive Subcutaneous K562 Tumors This study demonstrates that Chemokine Responsive aNK cells home to chemokine-expressing target tissue after intravenous administration. Because mouse and human chemokines do not cross react, the inventors developed a localized ligand-expressing tumor model as a surrogate model.

Experimental Methods (Table 1):
a. Animals:
i. Animal type: NSG mice (JAX), females, 7-8 weeks old
ii. Number of animals: 30 (28 animals [24+4 extras] who received NK cell injections; 2 additional mice received no NK treatment and were used as negative controls for flow cytometry)
b. Tumor model:
i. Cell line: K562, parental and CCL19-expressing subline, K-19
ii. Route of inoculation: subcutaneous; parental K562 on the left flank, K-19 on the right flank
iii. Inoculum: 1E6 cells in 100 μL serum free medium/Matrigel (v/v 1:1)
iv. Tumor burden upon treatment initiation: average 107 mm$^3$ for K-19; average 135 mm$^3$ for parental K562
v. Randomization: animals were randomized primarily based on the volume of K-19 tumors.
c. Test articles:
i. NK cells:
1. CD19 t-haNK (non-CR) (NantKwest Torrey Pines)
2. Quandracistronic Mi-aNK R7-19.1 (NantKwest Woburn)
ii. Fluorescent labeling:
1. Both types of NK cells were labeled with CFSE according to the manufacturer's manual immediately prior to in vivo administration.
2. For each time point, cultured CFSE labeled cells were harvested to use as positive controls for flow cytometry.
iii. Method of administration: Intravenous
iv. Dosage:
1. 1E7 cells/mouse
v. Dosing frequency: single dose
d. Tumor collection:
i. Time points: 3, 24 and 48 hours (±2 hours) post dosing
ii. N=4 mice/group/time point
iii. Tumor processing: collected tumors were dissociated into single cell suspensions according to an in-house protocol (attached), and subject to flow cytometry enumeration of CF SE-positive NK cells.
e. Formulas and Statistical Analyses:
i. Tumor volume=Length×Width$^2$/2 (Length and Width being the longest and shortest diameters of the tumor, respectively)
ii. Statistical analyses were performed by 1-way ANOVA followed by multiple comparison by Tukey test using GraphPad Prism version 7.0. P<0.05 is considered statistically significant.

TABLE 1

| | | Experimental Setup | | | |
|---|---|---|---|---|---|
| Group | N | Treatment | NK Cell Dose | NK dosing route | Euthanasia |
| A | 12 + 2 extras | CD19 t-haNK ® | 1E7 | IV | N = 4 at 3, 24 and 48 h post dosing |
| B | 12 + 2 extras | Quadracistronic R7-19.1 | 1E7 | IV | N = 4 at 3, 24 and 48 h post dosing |

Figure 13:
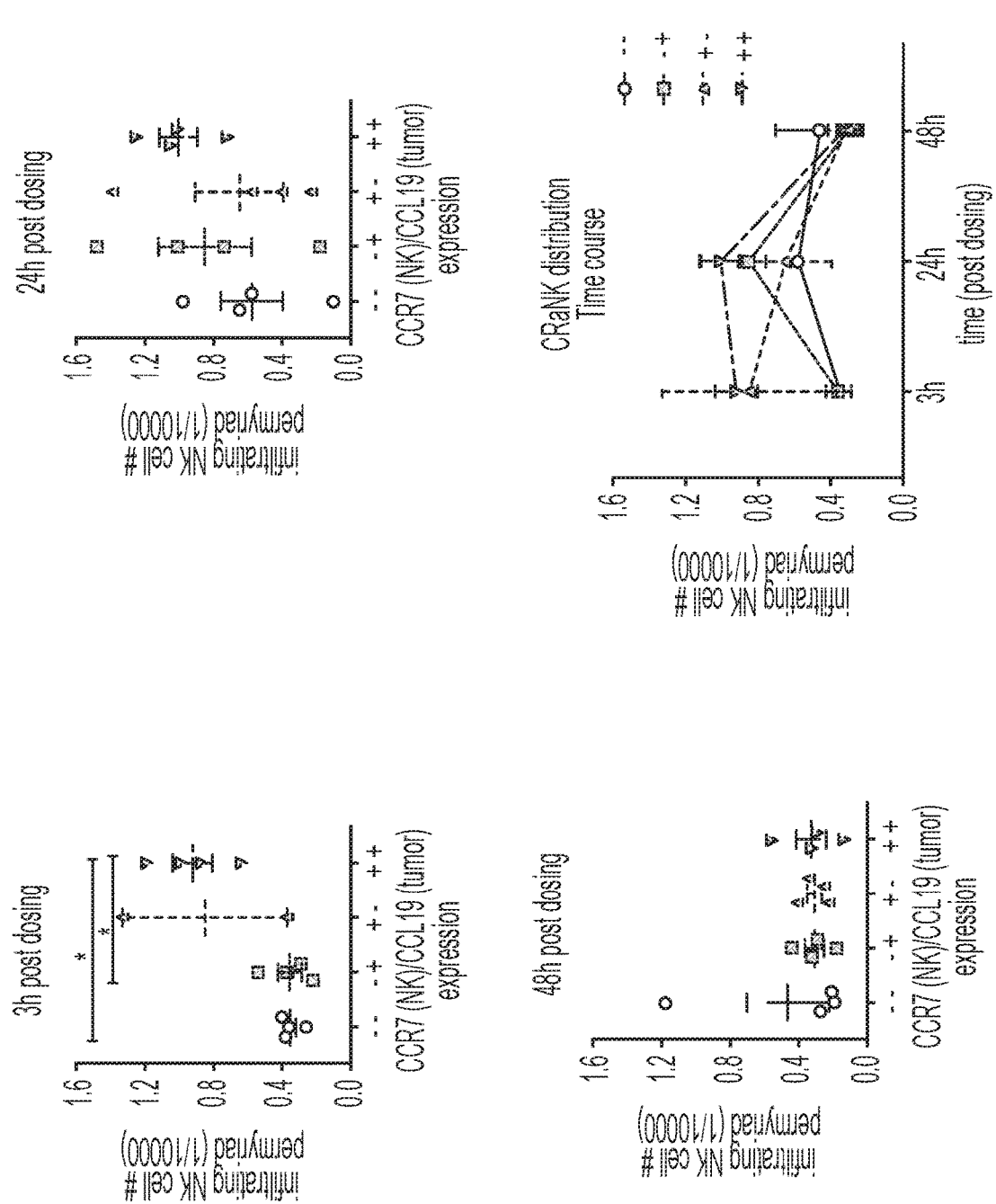
FIG. 13. Homing of non-CR versus Mi-T-haNK cells to parental or CCL19-expressing tumors at indicated hours post NK cell administration. Data are Mean±SEM. The – and + signs indicate the expression status of CCR7 receptor (first sign) and CCL19 ligand (second sign). *, P<0.05 by one-way ANOVA followed by multiple comparison by Tukey's test. The last panel presents the time course curve.
Figure 14:
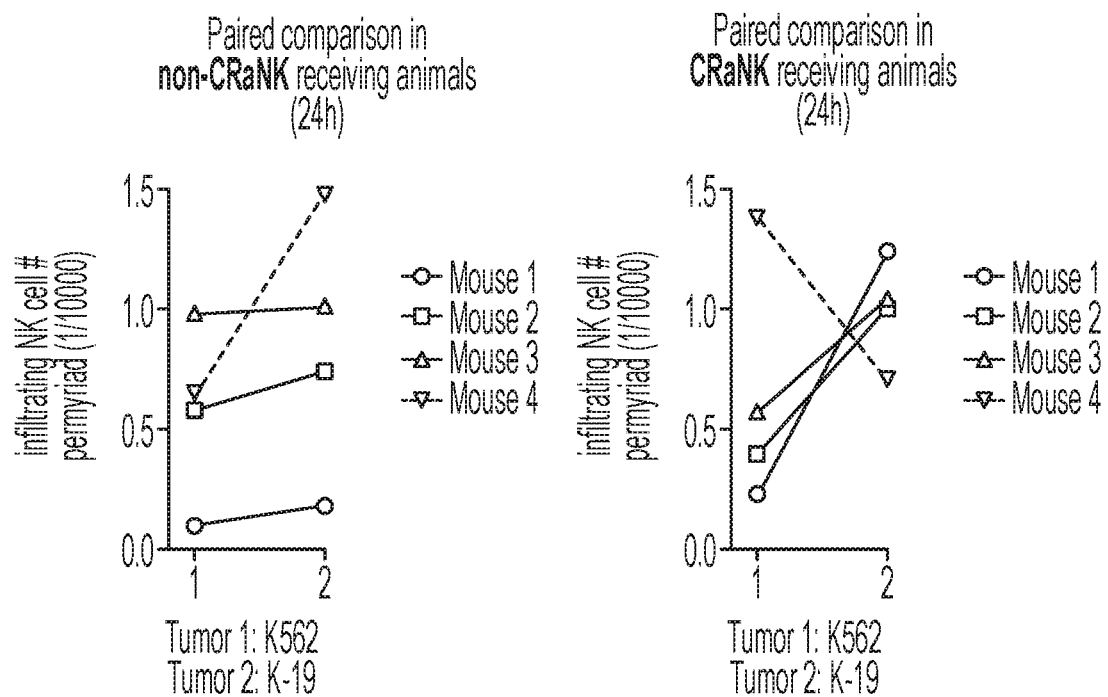
FIG. 14. A head-to-head comparison of non-CR and Mi-T-haNK cells infiltration to parental or CCL19-expressing tumors in single animals at 24 hours post dosing. 3 out of 4 animals receiving the Mi-T-haNK cells showed higher infiltration to the CCL19+ tumors, while 3 out of 4 animals receiving the non-CR CD19 t-haNK cells showed similar levels of infiltration to both K562 and K-19 tumors. The one "outlier" animal in each group is indicated by a dashed line.

Results:
a. Safety:
iii. Animals receiving both types of NK cells demonstrated mild to moderate degrees of acute reactions immediately after cell infusion (G1-G2, mildly-markedly depression, lethargic, slow or non-responsive).
iv. 2 (out of 14) animals in the R7-19.1 group were found dead within 24 hours post injection, while there was no mortality in the CD19 t-haNK group.
v. After 24 h, animals in the CD19 t-haNK group were able to recover, whereas animals in the R7-19.1 group continued to appear mildly depressed and less responsive to stimulations (G1). They became more responsive at 48 hours (G0), but still appeared to have rough fur and fast breathing.
b. NK cell homing:
vi. The numbers of tumor infiltrating NK cells at each time point are tabulated in Table 2 and graphed in FIG. 13.
1. The four CCR7 receptor-CCL19 ligand combinations are:
   a. CD19 t-haNK®, K562 tumor: no receptor-no ligand [– –];
   b. CD19 t-haNK®, K-19 tumor: no receptor-yes ligand [– +];
   c. R7-19.1 cells, K562 tumor: yes receptor-no ligand [+ –]; and
   d. R7-19.1 cells, K-19 tumor: yes receptor-yes ligand [+ +]
vii. At 3 hours, homing of R7-19.1 cells to K-19 tumors [+ +] was significantly greater than that of non-CR CD19 t-haNK cells to either CCL19– or CCL19+ tumors ([– –] and [– +], respectively; P<0.05). Since we were not able to recover many cells from 2 of the four K562 tumors in the B Group, however, a direct comparison of R7-19.1 cell homing to CCL19 negative vs. positive tumors in the same animals could not be achieved.
viii. At 24 hours, there were no statistically significant differences in NK cell homing among any of the four CCR7 receptor-CCL19 ligand combinations. However, when comparing the homing of each NK cell line to CCL19+ and – tumors within the same animal, 3 of the 4 animals that received R7-19.1 cells showed improved infiltration to the CCL19+ tumor, while the majority of animals receiving CD19 t-haNK®s showed similar levels of NK infiltration to both tumors regardless of their CCL19 expression (FIG. 14).
ix. At 48 hours, the overall number of tumor infiltrating NK cells decreased in all combinations, and there was no difference among any groups.

This example demonstrates that, at 3 hours post dosing, the co-presence of CCR7 receptor and CCL19 ligand resulted in more efficient NK cell infiltration. At 24 hours post dosing, in the non-CR aNK cell receiving animals, the NK cells exhibited similar levels of tumor homing regardless of CCL19 expression status in 3 out of 4 animals. In contrast, in animals receiving R7-19.1 cells, the NK cells were able to home more efficiently to CCL19 positive tumors compared to the parental non-ligand expressing control in 3 out of 4 animals. The number of tumor infiltrating NK cells decreased at 48 hours, regardless of the receptor or ligand expression. There is a visible trend of greater homing of R7-19.1 cells to CCL19 tumors especially during the early hours (<48 hours post dosing), suggesting higher exposure and potentially stronger cytotoxicity if the cells are used in a therapeutic setting.

Example 7: Comparative Efficacy Evaluation of CCR7-Expressing R7-19.1 Cells in NSG Mice Bearing Intravenous CCL19-Positive Raji Tumors CCR7 is a chemokine receptor that induces migration of cells towards the gradient of chemokines CCL19 and CCL21, typically expressed in lymph nodes and other lymphoid organs, which are the main sites of disease manifestation for B-cell lymphoma. We have created chemokine responsive NK-92® cells expressing a CD19-CAR, CCR7, CD16.158V, and ERIL-2 (i.e. R7-19.1 cells), based on the t-haNK platform. These cells harbor cancer-targeting chimeric antigen receptor (CAR) against the CD19 cancer antigen, a CD16 variant, and ER-IL-2 in addition to CCR7 expression. Previous distribution studies have demonstrated preferential homing of R7-19.1 cells towards CCL19-expressing subcutaneous (SC) tumors as compared to the parental counterpart.

In the present study, the anti-tumor effect of repeated intravenous (IV) administrations of R7-19.1 cells was evaluated in an IV xenograft model of Raji-19.5, which are Raji human Burkitt's lymphoma cells engineered to express CCL19, in NSG mice. The non-CCR7-expressing CD19 t-haNK cells (NK-92® [anti-CD19-CAR, CD16.158V, ERIL-2]) were used as the control NK cell line. A vehicle control group was also included.

While both NK cell lines demonstrated significant therapeutic efficacy in prolonging the survival of IV Raji-19.5 tumor-bearing animals when compared to the vehicle control, treatment with R7-19.1 cells conveyed significantly greater survival benefits than CD19 t-haNK cells. Although apparent treatment-related reactions were observed with both NK cell lines, these reactions are speculated to be mouse-specific issues connected with the administration of a relatively high dose of human derived cells.

TABLE 2

Homing of non-CR versus R7-19.1 cells to parental or CCL19-expressing tumors at indicated time points. Results are Mean ± SEM. N = 4 unless indicated otherwise.

| NK type | Tumor type | Receptor-ligand combination | NK cells in the tumor (permyriad) | | |
|---|---|---|---|---|---|
| | | | 3 hours | 24 hours | 48 hours |
| CD19 t-haNK | K562 (parental) | [– –] | 0.35 ± 0.03 | 0.58 ± 0.18 | 0.46 ± 0.24 |
| (non-CR) | K-19 | [– +] | 0.35 ± 0.07 | 0.85 ± 0.27 | 0.31 ± 0.05 |
| Quadracistronic | K562 (parental) | [+ –] | 0.85 ± 0.48 * | 0.65 ± 0.36 | 0.31 ± 0.06 |
| R7-19.1 | K-19 | [+ +] | 0.92 ± 0.12 | 1.01 ± 0.11 | 0.32 ± 0.09 |

* N = 2.

Study rationale and objectives: In vivo distribution data showed that IV administered R7-19.1 cells exhibited increased homing towards CCL19-expressing SC tumors. In the present study, the anti-tumor effect of repeated IV administrations of R7-19.1 cells was evaluated in an IV xenograft model of Raji-19.5 (a CCL19-expressing subline of Raji) in NSG mice. Note that the original study protocol contained additional groups of animals (groups A-C) that are not being included in this report. They are not relevant to the efficacy determination of R7-19.1 cells in this tumor model (see Table 3 for the abbreviated experimental design).

Study Materials:

Test Article(s). The test articles were R7-19.1 cells and CD19 t-haNK cells (non-CCR7-expressing control NK cells; clone 6). R7-19.1 cells were cultured in growth medium supplemented with 5% heat inactivated human AB serum and 0.05% Pluronic F68. With regards to CD19 t-haNK cells (non-CCR7-expressing control NK cells; clone 6), CD19 t-haNK cells were cultured in growth medium supplemented with 5% heat inactivated human AB serum and 0.05% Pluronic F68. Serum-free growth medium was used as vehicle control.

Test System: Test Animals: NOD.Cg-Prkdc$^{scid}$Il2rg$^{tm1Wjl}$/SzJ (NSG) female mice of age 10-11 weeks at study initiation (after quarantine and acclimation), and body weight between 20-27 grams upon randomization was used. The number of animals used in the study was 30, and the supplier was The Jackson Laboratory (610 Main Street Bar Harbor, Me. 04609 US). The animals were identified with ear tag, cage number, and tail mark number.

Raji-19.5 Tumor Model (Cancer Cell Line)

Cell Culture Medium: Raji-19.5 cancer cells were grown in ATCC-formulated RPMI-1640 Medium Modified supplemented with 10% fetal bovine serum.

a body weight loss of >20% when compared to the baseline (Day 0) body weight were euthanized according to the institutional IACUC policy, and subsequently necropsied at the Study Director's discretion.

Clinical Observation: Animals were observed daily for mortality/morbidity (G0 to G4; see Table 2 in Study Protocol in Appendix 1). Moribund and paralyzed animals were euthanized, and subsequently necropsied at the Study Director's discretion.

Randomization: On Day 3 (3 days post tumor cell inoculation), the 30 tumor-bearing mice were pseudo-randomized into 3 study groups of 10 based on animal body weight.

Test Article Administration: Twice weekly for 4 consecutive weeks (on Days 3, 6, 10, 13, 17, 20, 24, and 27), R7-19.1 and the control CD19 t-haNK cells grown in the exponential phase were harvested by centrifugation, and formulated in serum-free growth medium at the concentration of $5\times10^7$ cells/mL for IV administration at the dose of $1\times10^7$ cells per mouse with an injection volume of 200 µL. All cell processing and formulation procedures were performed at Room Temperature. Cell viability was above 80% for all dose preparations. As shown in Table 3, while Group D received the vehicle control, Groups E and F received CD19 t-haNK and R7-19.1 cells, respectively.

Endpoint: Animals were euthanized when they became paralyzed, moribund, or met any other endpoint criteria defined by the institutional IACUC. The experiment was ended on Day 30, when the last surviving animals succumbed to disease. Euthanasia was performed via $CO_2$ inhalation followed by cervical dislocation. Within the Study Director's discretion, some euthanized animals were necropsied to identify visible tumor nodules on internal organs. The complete record of mortality and death event as well as necropsy findings can be found in Appendix 5.

TABLE 3

Study Design (abbreviated)

| | | NK cell treatment | | | | | |
|---|---|---|---|---|---|---|---|
| Group | N | Cell type | Dose | Dosing Volume | Dosing Schedule | Route | Endpoint | Primary Readout |
| D | 10 | Vehicle | / | 0.2 mL | BIW × 4 weeks | IV | Paralyzed or moribund, or other endpoints defined by the IACUC | Survival rate |
| E | 10 | CD19 t-haNK | $1 \times 10^7$ | 0.2 mL | BIW × 4 weeks | IV | | |
| F | 10 | R7-19.1 | $1 \times 10^7$ | 0.2 mL | BIW × 4 weeks | IV | | |

BIW: twice weekly;
IACUC: institutional animal care and use committee;
IV: intravenous.

Cell Harvest: Raji-19.5 cells (passage 16) in exponential phase were collected by centrifugation following NantKwest's SOP_Suspension Cancer Cell Collection for In Vivo Studies. The cells were then washed and re-suspended in serum-free medium at the concentration of $5\times10^5$ cells/mL, and stored on ice prior to animal inoculation. Cells used in the in vivo study had a viability of 97%.

Inoculation: 30 mice were inoculated via the lateral tail vein with $1\times10^5$ cells in a 0.2 mL volume. This was defined as Day 0.

Experimental Procedures

Body Weight: Animals were weighed prior to enrollment (after quarantine/acclimation), prior to randomization, on the day of each dosing (but prior to dosing), the day after each dosing, and prior to euthanasia. Animals demonstrating Data Analysis:

Body Weight Curves: Body weight curves were analyzed by 2-way ANOVA (or mixed-effects analysis when there are missing values; see Amendment 2 in Appendix 1), followed by multiple comparison by Tukey test.

Survival Curves: Survival curves were analyzed by Log-rank (Mantel-Cox) test.

Statistical Analysis: All statistical analyses were performed using GraphPad Prism version 8. P<0.05 is considered statistically significant.

Results

Figure 15:
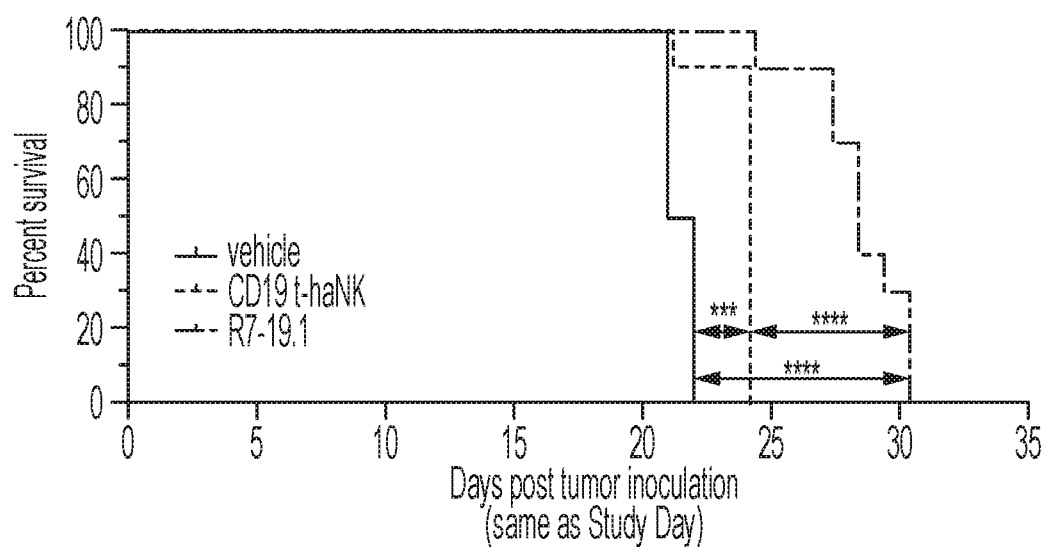
FIG. 15 illustrates the survival curve of IV Raji-19.5 tumor-bearing animals. Survival curves for Raji-19.5 IV tumor-bearing NSG mice treated with vehicle, CD19 t-haNK cells, or R7-19.1 cells. Statistical analysis was done by Log-rank (Mantel-Cox) test. *, P=0.0002; **, P<0.0001.

Efficacy: The main readout for efficacy was animal survival. A death event was counted when an animal was euthanized due to morbidity, paralysis, or body weight loss of >20%. No animals were found dead. As shown in FIG. 15 and Table 4, both treatments with R7-19.1 and with the control CD19 t-haNK cells were able to significantly prolong the survival of Raji-19.5 IV tumor bearing animals when compared to the vehicle control (P<0.0001 for R7-19.1; P=0.0002 for CD19 t-haNK, by Log-rank test), with an increase of 6.5 and 2.5 days, respectively, in Median Survival. This corresponds to an increase of 30% and 12%, respectively, over the vehicle control. More importantly, the expression of CCR7 chemokine-responsive receptor in the R7-19.1 cells conveyed an additional 4 days of increase in Median Survival (a 17% improvement) when compared to the CD19 t-haNK cells (P<0.0001).

TABLE 4

Summary of Median Survival of Raji-19.5 IV tumor-bearing NSG mice treated with vehicle, CD19 t-haNK cells, or R7-19.1 cells.

| Group (treatment) | Median Survival (days) | Increase in Median Survival, over Vehicle (days ( %)) | Increase in Median Survival, over CD19 t-haNK (days (%)) |
|---|---|---|---|
| D (Vehicle) | 21.5 | NA | NA |
| E (CD19 t-haNK ®) | 24 | 2.5 (12%) | NA |
| F (R7-19.1) | 28 | 6.5 (30%) | 4 (17%) |

NA: Not applicable.

Safety

As shown in FIG. 16, NK cell treated animals consistently demonstrated a 5-10% body weight loss after each treatment administration. In most cases, animals were able to recover from the cell injections and exhibited recovering body weight, resulting in the oscillation of the body weight change curves between doses. The initial dose, however, seemed to have caused the most severe reactions, and was associated with the longest recovery time in both clinical symptoms as well as body weight changes. Such reactions are not uncommon in animals receiving IV NK infusions, and certainly not specific to the R7-19.1 cells. The recoveries in body weight suggest that the weight loss was temporary and reversible.

Of note, towards the end of the study, animals displayed a precipitous decline in body weight (FIG. 16), likely due to disease progression. Necropsy revealed tumor nodules in the liver, ovary, and occasionally spleen, in almost all of the animals examined. The one exception was the first mouse euthanized in the CD19 t-haNK cell group, which reached a body weight loss of >20% the day after the 6$^{th}$ dosing. No visible tumor nodules were identified during necropsy for this animal. Therefore, the exact cause for the body weight loss that warranted euthanasia could not be determined.

Conclusion

IV dosing of freshly prepared R7-19.1 cells at the dosing level of 1×10$^7$ cells/dose, twice a week for 4 weeks, showed remarkable and statistically significant anti-tumor efficacy in the IV Raji-19.5 xenograft model. The treatment provided 6.5 days, or 30%, of an increase in median survival over the vehicle control group, and 4 days, or 17%, of an increase over the CD19 t-haNK treatment group.

Although apparent treatment-related reactions were observed, these reactions were transient, and surviving animals did show signs of recovery. These reactions are speculated to be mouse-specific issues connected with the administration of a relatively high dose of human derived NK cells, and therefore, unlikely to translate to humans.

Overall, CCR7-expressing R7-19.1 cells displayed significant therapeutic efficacy compared to vehicle and their non-chemokine-responsive counterpart in this IV model of Raji-19.5.

Example 8: Comparative Efficacy Evaluation of CCR7-Expressing R7-19.1 Cells in NSG Mice Bearing Subcutaneous CCL19-Positive Raji Tumors CCR7 is a chemokine receptor that induces migration of cells towards the gradient of chemokines CCL19 and CCL21, typically expressed in lymph nodes and other lymphoid organs, which are the main sites of disease manifestation for B-cell lymphoma. We have created chemokine responsive NK-92® cells that express aCD19-CAR, CCR7, CD16.158V, and ERIL-2 (i.e. R7-19.1 cells), based on the t-haNK platform. These cells harbor cancer-targeting chimeric antigen receptor (CAR) against the CD19 cancer antigen, a CD16 variant, and ER-IL-2 in addition to CCR7 expression. Previous distribution studies have demonstrated preferential homing of R7-19.1 cells towards CCL19-expressing subcutaneous (SC) tumors as compared to the parental counterpart.

In the present study, the anti-tumor effect of repeated intravenous (IV) administrations of R7-19.1 cells was evaluated in a SC xenograft model of Raji-19.5, which are Raji human Burkitt's lymphoma cells engineered to express CCL19, in NSG mice. The non-CCR7-expressing CD19 t-haNK cells (NK-92® [anti-CD19-CAR, CD16.158V, ERIL-2]) were used as the control NK cell line. A vehicle control group was also included.

In a sub-population of the tumor-bearing animals, both NK cell treatments were able to show appreciable effect in suppressing tumor growth, with the R7-19.1 treatment demonstrating a stronger inhibition than the control CD19 t-haNK cells. Although apparent treatment-related reactions were observed with both NK cell lines, these reactions are speculated to be mouse-specific issues connected with the administration of a relatively high dose of human derived cells.

Study Rationale and Objectives:

In vivo distribution data showed that IV administered R7-19.1 cells exhibited increased homing towards CCL19-expressing SC tumors. In the present study, the anti-tumor effect of repeated IV administrations of R7-19.1 cells was evaluated in IV and SC xenograft models of Raji-19.5 (a CCL19-expressing subline of Raji) in NSG mice.

Study Materials

Test Article(s): R7-19.1 cells (clone: and CD19 t-haNK cells (non-CCR7-expressing control NK cells; clone 6) were used as test articles while growth medium was used as vehicle control.

R7-19.1 cells were cultured in growth medium supplemented with 5% heat inactivated human AB serum and 0.05% Pluronic F68.

CD19 t-haNK cells were cultured in growth medium supplemented with 5% heat inactivated human AB serum and 0.05% Pluronic F68.

Test System: 30 NOD.Cg-Prkdc$^{scid}$Il2rg$^{tm1Wjl}$/SzJ (NSG) female mice of age 10-11 weeks at study initiation (after quarantine and acclimation), and body weight 19-28 grams on the day of tumor implantation were used in the study. The supplier was The Jackson Laboratory (610 Main Street Bar Harbor, Me. 04609 US). The animals were identidied using ear tag; cage number; and tail mark number.

Raji-19.5 Tumor Model (Cancer Cell Line)

Cell Culture Medium: Raji-19.5 cancer cells were cultured in ATCC-formulated RPMI-1640 Medium Modified supplemented with 10% fetal bovine serum.

Cell Harvest: Raji-19.5 cells (passage 16) in exponential phase were collected by centrifugation following NantKwest's SOP_Suspension Cancer Cell Collection for In Vivo Studies. The cells were then washed and re-suspended in serum free medium before mixing with equal part of Matrigel to reach a final concentration of $2.5 \times 10^6$ cells/mL. Cells were stored on ice prior to animal inoculation. Cells used in the in vivo study had a viability of 97%.

Inoculation: 30 animals were unilaterally inoculated on the right flank with $2.5 \times 10^5$ cancer cells in a 100 μL volume. The skin was shaved prior to injection.

Experimental Procedures

Tumor Volume Measurement: After SC tumor implantation, animals were examined at least twice a week for tumor establishment. When tumors became measurable, tumor volumes (TV) were measured with a digital hand held caliper twice weekly, and calculated using this formula: TV=Length×Width/2 [Length being the greatest diameter and Width being the shortest diameter of the tumor]. Animals with a tumor volume of over 2000 mm³ or with ulcerating tumors were euthanized according to the institutional IACUC policy, and subsequently necropsied. Tumor growth inhibition (TGI) was calculated as: TGI=$(T_C-T_t)/\Delta T_C \times 100\%$, where $T_C$ and $T_t$ is the average tumor volume for control and treatment groups, respectively, at a specific time point; and $\Delta T_C$ is the change in average tumor volume in the control group.

Body Weight: Animals were weighed prior to enrollment (after quarantine/acclimation), prior to randomization, on the day of each dosing (but prior to dosing), the day after each dosing, and prior to euthanasia. Animals demonstrating a body weight loss of >20% when compared to the baseline (Day 1) body weight were euthanized according to the institutional IACUC policy, and subsequently necropsied.

Clinical Observation: Animals were observed daily for mortality/morbidity (G0 to G4; see Table 5). Moribund or paralyzed animals were euthanized, and subsequently necropsied.

Randomization: When the average tumor volume reached 190 mm³, 30 mice were pseudo-randomized into 3 study groups with 10 mice per group, to achieve similar tumor volumes among the groups. This was defined as Day 1. Of note, due to the large variability in tumor sizes upon randomization, each group contained two sub-populations: 4-5 animals were with large (>200 mm³) tumors and 5-6 with small (<200 mm³) tumors (see FIG. 17).

Test Article Administration: Twice weekly for 4 consecutive weeks (on Days 1, 4, 9, 12, and 15), R7-19.1 and the control CD19 t-haNK cells grown in the exponential phase were harvested by centrifugation, and formulated in serum-free growth medium at the concentration of $5 \times 10^7$ cells/mL for IV administration at the dose of $1 \times 10^7$ cells per mouse with an injection volume of 200 μL. All cell processing and formulation procedures were performed at Room Temperature. Cell viability was above 80% for all dose preparations. As shown in Table 5, while Group A received the vehicle control, Groups B and C received CD19 t-haNK and R7-19.1 cells, respectively.

Endpoint: Animals were euthanized when they reached any of the above-mentioned endpoints defined by the institutional IACUC. Euthanasia was performed via $CO_2$ inhalation followed by cervical dislocation. Based on Study Director's judgement, some euthanized animals were necropsied to identify visible tumor nodules on internal organs.

TABLE 5

Study Design (abbreviated)

| | | | | NK cell treatment | | | | |
|---|---|---|---|---|---|---|---|---|
| Group | N | Cell type | Dose | Dosing Volume | Dosing Schedule | Route | Endpoint | Primary Readout |
| A | 10 | Vehicle | / | 0.2 mL | BIW × 4 weeks | IV | Tumor burden or other endpoints defined by IACUC[1] | Tumor growth inhibition (TGI) |
| B | 10 | CD19 t-haNK ® | $1 \times 10^7$ | 0.2 mL | BIW × 4 weeks | IV | | |
| C | 10 | R7-19.1 | $1 \times 10^7$ | 0.2 mL | BIW × 4 weeks | IV | | |

BIW: twice weekly; IACUC: institutional animal care and use committee; IV: intravenous; TGI: tumor growth inhibition.
[1] tumor burden endpoint defined by the IACUC: tumor volume exceeding 2000 mm³; ulcerating tumor; and tumor interfering with normal gait.

Data Analysis

Tumor Volume Calculation: Tumor volume=Length×Width²/2 (Length and Width being the longest and shortest diameters of the tumor, respectively)

Tumor Growth Inhibition (TGI) Calculation: TGI=$(T_C-T_t)/\Delta T_C \times 100\%$, where $T_C$ and $T_t$ is the average tumor volume for control and treatment groups at a specific time point, respectively, and $\Delta T_C$ is the change in average tumor volume in the control group.

Statistical Analysis of Tumor Growth and Body Weight Curves: Tumor growth and body weight curves were analyzed by 2-way ANOVA (or mixed-effects analysis when there are missing values; see Amendment 2 in Appendix 1), followed by multiple comparison by Tukey test. All statistical analyses were performed using GraphPad Prism version 8. $P<0.05$ is considered statistically significant.

Results

Efficacy: The primary readout in this study is tumor growth inhibition. SC tumors with different initial tumor volumes may have had differentially developed vasculature and CCL19 gradient, which may affect the test articles' distribution to the tumor. Additionally, small and large tumors may respond to NK cell treatments in different manners. For these reasons, the two sub-populations (i.e. large and small tumors) are analyzed separately.

As shown in FIG. 18, in the sub-population of animals bearing large initial tumors, treatment with both NK cell lines showed appreciable tumor growth inhibition when compared to the vehicle control, in which 3 out of 4 animals had to be euthanized on Day 9 due to tumor volume in excess of 2000 mm³ or presence of an ulcerated tumor. In contrast, in the NK cell-treated groups, the majority of animals survived until Day 12 or Day 15. More importantly, on Day 15, there was an ostensible enhancement in tumor growth inhibition in the R7-19.1 group when compared to its non-CCR7-expressing counterpart, achieving a TGI of 35%.

This difference failed to reach statistical significance, possibly due to the small cohort size (N of 2 and 4 for CD19 t-haNK and R7-19.1 groups, respectively).

For animals that bore small tumors upon treatment initiation, however, neither of the NK cell therapies were effective in suppressing tumor growth when compared to the vehicle control, or against each other (FIG. 19). This is plausibly attributed to three factors: 1) the small tumors may have had underdeveloped vasculature and therefore lower exposure/accessibility to the test articles, causing both NK cell therapies to fail. 2) Rather than responding to the mere presence of chemokines, CCR7-mediated chemotaxis requires a chemokine gradient. Such gradient of CCL19 may have been inadequately established in small tumors, leading to the lack of differentiability between R7-19.1 cells versus the CD19 t-haNK control. And 3) there were a few "outliers" in tumor growth in these already small cohorts, further precluding statistical analysis.

As shown in FIG. 20, NK cell treated animals typically demonstrated a 5-10% body weight loss after each treatment administration. In most cases, animals were able to recover from the cell injections and exhibited recovering body weight, resulting in the oscillation of the body weight change curves between doses. The initial dose, however, seemed to have caused the most acute and severe reactions, and was associated with the longest recovery time for both clinical symptoms as well as body weight changes. Such reactions are not uncommon in animals receiving IV NK infusions, and certainly not specific to the R7-19.1 cells. The recoveries in body weight suggest that the weight loss was temporary and reversible.

Conclusion

IV dosing of freshly prepared chemokine-responsive R7-19.1 cells at the dosing level of $1 \times 10^7$ cells/dose, twice a week for 4 weeks, led to an appreciable tumor growth inhibition in animals that bore large SC Raji-19.5 tumors, although such effect did not reach statistical significance, possibly due to the small cohort size. This treatment regimen did not show therapeutic efficacy in animals with small initiating tumor volume. This may be attributed to the underdevelopment of tumor vasculature and/or inadequately established chemokine gradient in small tumors. Apparent treatment-related reactions were observed. These reactions, however, were transient, and animals did show signs of recovery. These reactions are speculated to be mouse-specific issues connected with the administration of a relatively high dose of human derived NK cells, and therefore, unlikely to translate to humans.

Example 9: Producing the aTGFβ/PD-L1 CAR Modified NK-92® Cells

A TGFβ trap composed of a single chain dimer of the extracellular domain of TGFβRII was cloned into a quadricistronic plasmid vector that also contains PD-L1 CAR, CD16 and erIL-2 transgenes (FIG. 21). The quadricistronic plasmids were electroporated into the aNK cells to create modified NK-92 cells. The modified NK-92® cells were selected by IL-2-depleted media because untransformed aNK cells, being IL-2 dependent, could not survive in IL-2 depleted media. FIG. 22 shows that aTGFβ/PD-L1 CAR modified NK-92® cells co-express high level of PD-L1 CAR and CD16.

Limiting Dilution Cloning

An aliquot of a polyclonal aTGFβ/PD-L1 t-haNK™ pool culture diluted to a density of 3 cells/ml in growth medium without IL-2 supplementation. This cell suspension was aliquoted in 96-well plates at a volume of 200pl per well, corresponding to 0.6 cells per well on average. The plates were incubated at 37° C. for 10 days, then visually checked for cell growth. Clones were picked and transferred to larger vessels for expansion and characterization.

Bioanalytical Methods

Cell Culture:

Polyclonal and clonal aTGFβ/PD-L1 t-haNK™ cells were culture in growth medium supplemented with 5% heat inactivated human AB serum without IL-2.

aNK cells were cultured in growth medium supplemented with 5% heat inactivated human AB serum and 500 IU/ml recombinant human IL-2.

haNK cells were cultured in growth medium supplemented with 5% heat inactivated human AB serum without IL-2.

K562 and MDA-MB-231 cells were cultured in RPMI-1640 supplemented with 10% heat inactivated fetal bovine serum and a cocktail of antibiotics/antimycotic. K562 cells were passaged every 2-5 days, or whenever the culture medium appeared yellow.

SUP-B15$^{PD-L1+}$ and SUP-B15$^{CD19KO/CD20+}$ cells were cultured in RPMI-1640 supplemented with 20% heat inactivated fetal bovine serum, 55 uM of beta-mercaptoethanol, and a cocktail of antibiotics/antimycotic. Cells were otherwise passaged as K562 cells above.

Antibody Staining for Flow Cytometry Analysis:

Cells were harvested by centrifugation, washed twice in FACS buffer (5% FBS in 1×D-PBS), and resuspended in 1 ml FACS buffer. For direct fluorophore-conjugated antibody staining of surface proteins, cells were incubated with an appropriate conjugated antibody (or isotype control) for 20 mins at 4° C. in the dark, then washed twice with FACS buffer. For detection of CAR proteins, cells were incubated with Biotinylated Anti F(ab')$_2$ Fragment antibody, followed by incubation with Streptavidin-APC antibody. Samples were analyzed on a MACSQuant Flow cytometer.

Cytotoxicity:

Suspension-growing cell lines were resuspended by up and down pipetting of the cell cultures. Cells viability was determined by automated counting (trypan blue exclusion method). Target cells were labelled with CFSE dye, and dilutions of target and effector cells to the required cell concentrations were made in RPMI-1640 supplemented with 10% heat-inactivated FBS and antibiotics/antimycotic. Effector and target cells were mixed at different effector to target (E:T of 20:1, 10:1, 5:1, 2.5:1, 1.25:1, 0.62:1, 0.31:1, and 0.15:1) ratios in a 96-well plate and co-incubated for 4 h in a 5% CO2 atmosphere 37° C. incubator. PI was then added for fluorescent labelling of dead cells and the assay was analyzed on a MACSquant flow cytometry device.

ADCC:

Suspension-growing cell lines were resuspended by up and down pipetting of the cell cultures. Cells viability was determined by automated counting (trypan blue exclusion method). Target cells were labelled with PKH67-GL dye, and dilutions of target and effector cells to the required cell concentrations were made in RPMI-1640 supplemented with 10% heat-inactivated FBS and antibiotics/antimycotic. Target cells were pre-incubated with monoclonal antibodies trastuzumab, rituximab, or no antibody for 30 min at R.T. Antibody-labelled target cells (and no-antibody controls) were then mixed with effector cells at different effector to target ratios (E:T of 20:1, 10:1, 5:1, 2.5:1, 1.25:1, 0.62:1, 0.31:1, and 0.15:1) in a 96-well plate and co-incubated for 4 h in a 5% CO$_2$ atmosphere 37° C. incubator. PI was then added for fluorescent labelling of dead cells and the assay was analyzed on a MACSquant flow cytometry device.

Quantification of TGFβ Trap Secreted by aTGFβ/PD-L1t-haNK Cells

Sample supernatants for analysis were prepared by a first centrifugation step at 500×g for 5 min to remove cells, followed by a second centrifugation at 2000×g for 5 min to remove cell debris. Sample supernatants were frozen at −80° C. until analysis. Cell pellets from the 500×g centrifugation step were resuspended, triplicates were pooled and the cell density was recorded. The concentration of TGFβ trap in the sample supernatants was measured using a human TGFβRII ELISA detection kit, according to the manufacturer's instructions and compared to a provided standard. TGFβ trap concentrations were normalized to cell numbers and expressed as pg/ml/$10^6$ cells. FIG. 23 shows that all aTGFβ PD-L1 t-haNK clones secreted large amounts of TGFβ trap (between ~6 and ~13 ng/ml/$10^6$ cells).

Cytotoxicity of aTGFβ/PD-L1 t-haNK™ Cells on Target Cell Lines

The cytotoxicity of aTGFβ/PD-L1 t-haNK™ cells were analyzed by incubating with target cells K562 cells, SUP-B15$^{PD-L1+}$ cells, and MDA-MB-231 cells. FIG. 24 shows that aTGFβ/PD-L1 t-haNK™ cells maintained comparable cytotoxicity to parental aNK cells in killing K562 cells (target cells).

FIG. 25 shows that aTGFβ/PD-L1 t-haNK™ cells demonstrated enhanced specific killing of the aNK™-resistant, PD-L1-positive SUP-B15 cell line—about 70% of cells were killed by aTGFβ/PD-L1 t-haNK™ cells relative to only about 10% of cells were killed by aNK cells at an effector to target ratio of 8.

FIG. 26 shows that aTGFβ/PD-L1 t-haNK™ cells demonstrated enhanced specific killing of the MDA-MB-231 cell line—about 90% of cells were killed by aTGFβ/PD-L1 t-haNK™ cells relative to only about 40% of cells were killed by aNK cells at an effector to target ratio of 8.

FIG. 27 shows that the ADCC activity of the aTGFβ/PD-L1 t-haNK™ cells on SUP-B15$^{CD19KO/CD20+}$ cells (CD19-, CD20+, Her2-neu-, NK-resistant) in combination with anti-CD20 rituximab monoclonal antibody or with anti-Her2-neu trastuzumab monoclonal antibody. In a 4 h cytotoxicity assay, aTGFβ/PD-L1 t-haNK cells were able to efficiently target and kill the resistant SUP-B15$^{CD19KO/CD20+}$ when combined with the anti-CD20 antibody rituximab. Neither haNK® nor the aTGFβ/PD-L1 t-haNK™ clones were able to kill target SUP-B15$^{CD19KO/CD20+}$ cells when combined with the anti-Her2/neu control antibody trastuzumab.

Example 10: TGFβ Trap Secreted by Modified NK-92® Cells Inhibits TGFβ Activity

HEK293 cells engineered with a TGFβ-responsive element (SMAD-binding promoter) directly expression of a Luciferase reporte gene display a dose-dependent increase in Luciferase activity when treated with TGFβ (FIG. 28).

FIG. 29 shows that TGFβ induction of luciferase activity in HEK293 reporter cells can be inhibited by co-incubation with culture supernatant of aTGFβ/PD-L1 t-haNK cells, whereas culture supernatant from haNK control cells has limited effect on the luciferase activity.

Example 11: Production of IL-12 by Modified NK-92® Cells

NK-92 cells were transduced with lentiviral contructs encoding the functional IL-12 p70 dimer as a single chain polypeptide, either in the p35-p40 orientation or the p40-p35 orientation (FIG. 30). Following Neomycin selection, transduced NK-92 cells were able to secrete detectable level of p70 IL-12. The addition of a 2A peptide at the C-terminal end of the IL-12 dimer did not affect secretion of the protein.

Production of IL-12/PD-L1 CAR Modified NK-92® Cells

A single chain dimer of IL-12 (scIL-12 p'70) was cloned into a quadricistronic plasmid vector that also contains PD-L1 CAR, CD16 and erIL-2 transgenes. The quadricistronic plasmids (FIG. 31) were electroporated into the aNK cells to create modified NK-92 cells. The modified NK-92® cells were selected by IL-2-depleted media because untransformed aNK cells, being IL-2 dependent, cannot survive in IL-2 depleted media. FIG. 33 shows that IL-12/PD-L1 CAR modified NK-92® cells were able to secrete significant amount of the scIL-12 p70 cytokine.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A recombinant NK-92 cell, comprising a recombinant quadricistronic nucleic acid that includes a sequence encoding a CCR7 homing receptor, a CD19CAR, a CD16.158V, and erIL-2, wherein the recombinant NK-92 cell expresses the CCR7 homing receptor, the CD19CAR, the CD16.158V, and the erIL-2 wherein surface expression of the CCR7 enables the recombinant NK-92 cell to migrate towards CCL21 and/or CCL19, wherein the NK-92 cell has American Type Culture Collection (ATCC) deposit number CRL-2407, and wherein the sequence encoding the CCR7 comprises the nucleotide sequence of SEQ ID NO:1.

2. The recombinant NK-92 cell of claim 1, wherein the cell is contained in a medium for administration.

3. The recombinant NK-92 cell of claim 2, wherein the medium for administration comprises human serum albumin, human plasma, and/or a serum substitute acceptable for use in human therapeutics.

4. The recombinant NK-92 cell of claim 1, wherein the cell is cryopreserved.

* * * * *

SEQUENCE LISTING

<160> NUMBER OF SEQ ID NOS: 69

<210> SEQ ID NO 1
<211> LENGTH: 1119
<212> TYPE: DNA
<213> ORGANISM: Artificial Sequence
<220> FEATURE:
<223> OTHER INFORMATION: Laboratory made

<400> SEQUENCE: 1

```
atgaaaagcg tgctggtggt ggctctcctt gtcattttcc aggtatgcct gtgtcaagat      60
gaggtcacgg acgattacat cggagacaac accacagtgg actacacttt gttcgagtct     120
ttgtgctcca agaaggacgt gcggaacttt aaagcctggt tcctccctat catgtactcc     180
atcatttgtt tcgtgggcct actgggcaat gggctggtcg tgttgaccta tatctatttc     240
aagaggctca agaccatgac cgatacctac ctgctcaacc tggcggtggc agacatcctc     300
ttcctcctga cccttccctt ctgggcctac agcgcggcca agtcctgggt cttcggtgtc     360
cacttttgca agctcatctt tgccatctac aagatgagct tcttcagtgg catgctccta     420
cttctttgca tcagcattga ccgctacgtg ccatcgtcc aggctgtctc agctcaccgc      480
caccgtgccc gcgtccttct catcagcaag ctgtcctgtg tgggcatctg gatactagcc     540
acagtgctct ccatcccaga gctcctgtac agtgacctcc agaggagcag cagtgagcaa     600
gcgatgcgat gctctctcat acagagcat gtggaggcct ttatcaccat ccaggtggcc      660
cagatggtga tcggctttct ggtccccctg ctggccatga gcttctgtta ccttgtcatc     720
atccgcaccc tgctccaggc acgcaacttt gagcgcaaca aggccatcaa ggtgatcatc     780
gctgtggtcg tggtcttcat agtcttccag ctgcctaca atggggtggt cctggcccag      840
acggtggcca acttcaacat caccagtagc acctgtgagc tcagtaagca actcaacatc     900
gcctacgacg tcacctacag cctggcctgc gtccgctgct gcgtcaaccc tttcttgtac     960
gccttcatcg gcgtcaagtt ccgcaacgat ctcttcaagc tcttcaagga cctgggctgc    1020
ctcagccagg agcagctccg gcagtggtct tcctgtcggc acatccggcg ctcctccatg    1080
agtgtggagg ccgagaccac caccaccttc tccccatag                           1119
```

<210> SEQ ID NO 2
<211> LENGTH: 405
<212> TYPE: DNA
<213> ORGANISM: Artificial Sequence
<220> FEATURE:
<223> OTHER INFORMATION: Laboratory made

<400> SEQUENCE: 2

```
atggctcagt cactggctct gagcctcctt atcctggttc tggcctttgg catccccagg      60
acccaaggca gtgatggagg ggctcaggac tgttgcctca agtacagcca aggaagatt     120
cccgccaagg ttgtccgcag ctaccggaag caggaaccaa gcttaggctg ctccatccca     180
gctatcctgt tcttgccccg caagcgctct caggcagagc tatgtgcaga cccaaaggag     240
ctctgggtgc agcagctgat gcagcatctg acaagacac catccccaca gaaaccagcc     300
cagggctgca ggaaggacag gggggcctcc aagactggca gaaaggaaa gggctccaaa     360
ggctgcaaga ggactgagcg gtcacagacc cctaaagggc catag                    405
```

<210> SEQ ID NO 3
<211> LENGTH: 1178
<212> TYPE: DNA
<213> ORGANISM: Artificial Sequence
<220> FEATURE:
<223> OTHER INFORMATION: laboratory made

<400> SEQUENCE: 3

```
gctccggtgc ccgtcagtgg gcagagcgca catcgcccac agtccccgag aagttggggg      60
gaggggtcgg caattgaacc ggtgcctaga gaaggtggcg cggggtaaac tgggaaagtg     120
```

| | |
|---|---|
| atgtcgtgta ctggctccgc cttttcccg agggtgggggg agaaccgtat ataagtgcag | 180 |
| tagtcgccgt gaacgttctt tttcgcaacg ggtttgccgc cagaacacag gtaagtgccg | 240 |
| tgtgtggttc ccgcgggcct ggcctcttta cgggttatgg cccttgcgtg ccttgaatta | 300 |
| cttccacctg gctgcagtac gtgattcttg atcccgagct tcgggttgga agtgggtggg | 360 |
| agagttcgag gccttgcgct taaggagccc cttcgcctcg tgcttgagtt gaggcctggc | 420 |
| ctgggcgctg gggccgccgc gtgcgaatct ggtggcacct tcgcgcctgt ctcgctgctt | 480 |
| tcgataagtc tctagccatt taaaatttt gatgacctgc tgcgacgctt ttttctggc | 540 |
| aagatagtct tgtaaatgcg ggccaagatc tgcacactgg tatttcggtt tttggggccg | 600 |
| cgggcggcga cggggcccgt gcgtcccagc gcacatgttc ggcgaggcgg ggcctgcgag | 660 |
| cgcggccacc gagaatcgga cggggggtagt ctcaagctgg ccggcctgct ctggtgcctg | 720 |
| gcctcgcgcc gccgtgtatc gccccgccct gggcggcaag gctggccggg tcggcaccag | 780 |
| ttgcgtgagc ggaaagatgg ccgcttcccg gccctgctgc agggagctca aaatggagga | 840 |
| cgcggcgctc gggagagcgg gcgggtgagt caccccacaca aaggaaaagg gccttttccgt | 900 |
| cctcagccgt cgcttcatgt gactccacgg agtaccgggc gccgtccagg cacctcgatt | 960 |
| agttctcgag cttttggagt acgtcgtctt taggttgggg ggaggggttt tatgcgatgg | 1020 |
| agtttcccca cactgagtgg gtggagactg aagttaggcc agcttggcac ttgatgtaat | 1080 |
| tctccttgga atttgccctt tttgagtttg gatcttggtt cattctcaag cctcagacag | 1140 |
| tggttcaaag ttttttctt ccatttcagg tgtcgtga | 1178 |

<210> SEQ ID NO 4
<211> LENGTH: 30
<212> TYPE: DNA
<213> ORGANISM: Artificial Sequence
<220> FEATURE:
<223> OTHER INFORMATION: laboratory made

<400> SEQUENCE: 4

| | |
|---|---|
| ggaggaaaaa ctgtttcata cagaaggcgt | 30 |

<210> SEQ ID NO 5
<211> LENGTH: 32
<212> TYPE: DNA
<213> ORGANISM: Artificial Sequence
<220> FEATURE:
<223> OTHER INFORMATION: laboratory made

<400> SEQUENCE: 5

| | |
|---|---|
| tagagggtat ataatggaag ctcgaattcc ag | 32 |

<210> SEQ ID NO 6
<211> LENGTH: 320
<212> TYPE: DNA
<213> ORGANISM: Artificial Sequence
<220> FEATURE:
<223> OTHER INFORMATION: laboratory made

<400> SEQUENCE: 6

| | |
|---|---|
| aataaaatat ctttattttc attacatctg tgtgttggtt ttttgtgtga atcgatagta | 60 |
| ctaacatacg ctctccatca aaacaaaacg aaacaaaaca aactagcaaa ataggctgtc | 120 |
| cccagtgcaa gtgcaggtgc cagaacattt ctctggccta actggccggt acctgagctc | 180 |
| gctagcggag gaaaaactgt ttcatacaga aggcgtggag gaaaaactgt ttcatacaga | 240 |
| aggcgtggag gaaaaactgt ttcatacaga aggcgtagat ctagactcta gagggtatat | 300 | aatggaagct cgaattccag    320

<210> SEQ ID NO 7
<211> LENGTH: 6887
<212> TYPE: DNA
<213> ORGANISM: Artificial Sequence
<220> FEATURE:
<223> OTHER INFORMATION: laboratory made

<400> SEQUENCE: 7

| | |
|---|---|
| aggtcctgct ttctctgacc tgcattctct ccctggcc tgtgccgctt tctgtctgca | 60 |
| gcttgtggcc tgggtcacct ctacggctgg cccagatcct tccctgccgc ctccttcagg | 120 |
| ttccgtcttc ctccactccc tcttcccctt gctctctgct gtgttgctgc ccaaggatgc | 180 |
| tctttccgga gcacttcctt ctcggcgctg caccacgtga tgtcctctga gcggatcctc | 240 |
| cccgtgtctg gtcctctcc gggcatctct cctccctcac ccaaccccat gccgtcttca | 300 |
| ctcgctgggt ccctttttcc ttctccttct ggggcctgtg ccatctctcg tttcttagga | 360 |
| tggccttctc cgacggatgt ctcccttgcg tcccgcctcc ccttcttgta ggcctgcatc | 420 |
| atcaccgttt ttctggacaa ccccaaagta ccccgtctcc ctggctttag ccacctctcc | 480 |
| atcctcttgc tttctttgcc tggacacccc gttctcctgt ggattcgggt cacctctcac | 540 |
| tcctttcatt tgggcagctc ccctaccccc cttacctctc tagtctgtgc tagctcttcc | 600 |
| agcccctgt catggcatct tccaggggtc cgagagctca gctagtcttc ttcctccaac | 660 |
| ccgggccct atgtccactt caggacagca tgtttgctgc ctccagggat cctgtgtccc | 720 |
| cgagctggga ccaccttata ttcccagggc cggttaatgt ggctctggtt ctgggtactt | 780 |
| ttatctgtcc cctccacccc acagtggggt acctctagag ctgaccaaaa gagcaccaaa | 840 |
| ggcgccctga ccttcagccc ctacctgcgc tccggtgccc gtcagtgggc agagcgcaca | 900 |
| tcgcccacag tccccgagaa gttgggggga gggtcggca attgaaccgg tgcctagaga | 960 |
| aggtggcgcg gggtaaactg ggaaagtgat gtcgtgtact ggctccgcct tttcccgag | 1020 |
| ggtgggggag aaccgtatat aagtgcagta gtcgccgtga acgttctttt tcgcaacggg | 1080 |
| tttgccgcca gaacacaggt aagtgccgtg tgtggttccc gcgggcctgg cctctttacg | 1140 |
| ggttatggcc cttgcgtgcc ttgaattact tccacctggc tgcagtacgt gattcttgat | 1200 |
| cccgagcttc gggttggaag tgggtgggag agttcgaggc cttgcgctta aggagcccct | 1260 |
| tcgcctcgtg cttgagttga ggcctggcct gggcgctggg gccgccgcgt gcgaatctgg | 1320 |
| tggcaccttc gcgcctgtct cgctgctttc gataagtctc tagccattta aaattttga | 1380 |
| tgacctgctg cgacgctttt tttctggcaa gatagtcttg taaatgcggg ccaagatctg | 1440 |
| cacactggta tttcggtttt tggggccgcg gcggcgacg gggcccgtgc gtcccagcgc | 1500 |
| acatgttcgg cgaggcgggg cctgcgagcg cggccaccga gaatcggacg ggggtagtct | 1560 |
| caagctggcc ggcctgctct ggtgcctggc ctcgcgccgc cgtgtatcgc cccgccctgg | 1620 |
| gcggcaaggc tgggccggtc ggcaccagtt gcgtgagcgg aaagatggcc gcttcccggc | 1680 |
| cctgctgcag ggagctcaaa atggaggacg cggcgctcgg gagagcgggc gggtgagtca | 1740 |
| cccacacaaa ggaaaagggc cttttccgtcc tcagccgtcg cttcatgtga ctccacggag | 1800 |
| taccgggcgc cgtccaggca cctcgattag ttctcgagct tttggagtac gtcgtctta | 1860 |
| ggttgggggg aggggtttta tgcgatggag tttcccacac tgagtgggt ggagactgaa | 1920 |
| gttaggccag cttggcactt gatgtaattc tccttggaat ttgcccttttt tgagtttgga | 1980 |

-continued

```
tcttggttca ttctcaagcc tcagacagtg gttcaaagtt ttttcttcc atttcaggtg    2040 tcgtgataat acgactcact atagggagac ccaagctgga attcggcggc cgccaccatg    2100
aaaagcgtgc tggtggtggc tctccttgtc attttccagg tatgcctgtg tcaagatgag    2160
gtcacggacg attacatcgg agacaacacc acagtggact acactttgtt cgagtctttg    2220
tgctccaaga aggacgtgcg gaactttaaa gcctggttcc tccctatcat gtactccatc    2280
atttgtttcg tgggcctact gggcaatggg ctggtcgtgt tgacctatat ctatttcaag    2340
aggctcaaga ccatgaccga tacctacctg ctcaacctgg cggtggcaga catcctcttc    2400
ctcctgaccc ttcccttctg ggcctacagc gcggccaagt cctgggtctt cggtgtccac    2460
ttttgcaagc tcatctttgc catctacaag atgagcttct tcagtggcat gctcctactt    2520
ctttgcatca gcattgaccg ctacgtggcc atcgtccagg ctgtctcagc tcaccgccac    2580
cgtgcccgcg tccttctcat cagcaagctg tcctgtgtgg gcatctggat actagccaca    2640
gtgctctcca tcccagagct cctgtacagt gacctccaga ggagcagcag tgagcaagcg    2700
atgcgatgct ctctcatcac agagcatgtg gaggccttta tcaccatcca ggtggcccag    2760
atggtgatcg gctttctggt ccccctgctg ccatgagct tctgttacct tgtcatcatc    2820
cgcaccctgc tccaggcacg caactttgag cgcaacaagg ccatcaaggt gatcatcgct    2880
gtggtcgtgg tcttcatagt cttccagctg ccctacaatg gggtggtcct ggcccagacg    2940
gtggccaact tcaacatcac cagtagcacc tgtgagctca gtaagcaact caacatcgcc    3000
tacgacgtca cctacagcct ggcctgcgtc cgctgctgcg tcaacccttt cttgtacgcc    3060
ttcatcggcg tcaagttccg caacgatctc ttcaagctct tcaaggacct gggctgcctc    3120
agccaggagc agctccggca gtggtcttcc tgtcggcaca tccggcgctc ctccatgagt    3180
gtggaggcca agaccaccac caccttctcc ccataggcgg ccgcggtcat agctgtttcc    3240
tgaacagatc ccgggtggca tccctgtgac ccctccccag tgcctctcct ggccctggaa    3300
gttgccactc cagtgcccac cagccttgtc ctaataaaat taagttgcat cattttgtct    3360
gactaggtgt ccttctataa tattatgggg tggaggggggg tggtatggag caaggggcaa    3420
gttgggaaga caacctgtag ggcctgcggg gtctattggg aaccaagctg gagtgcagtg    3480
gcacaatctt ggctcactgc aatctccgcc tcctgggttc aagcgattct cctgcctcag    3540
cctcccgagt tgttgggatt ccaggcatgc atgaccaggc tcagctaatt tttgttttt    3600 tggtagagac ggggtttcac catattggcc aggctggtct ccaactccta atctcaggtg    3660
atctacccac cttggcctcc caaattgctg ggattacagg cgtgaaccac tgctcccttc    3720
cctgtccttc tgatttaaa ataactatac cagcaggagg acgtccagac acagcatagg    3780
ctacctggcc atgcccaacc ggtgggacat ttgagttgct tgcttggcac tgtcctctca    3840
tgcgttgggt ccactcagta gatgcctgtt gaattgggta cgcggccagc ttaatgcata    3900
acttcgtata atgtatgcta tacgaagtta tgttaattaa gggtgcagcg gcctccgcgc    3960
cgggttttgg cgcctcccgc gggcgccccc tcctcacgg cgagcgctgc cacgtcagac    4020
gaagggcgca ggagcgttcc tgatccttcc gcccggacgc tcaggacagc ggcccgctgc    4080
tcataagact cggccttaga acccagtat cagcagaagg acattttagg acgggacttg    4140
ggtgactcta gggcactggt tttctttcca gagagcggaa caggcgagga aaagtagtcc    4200
cttctcggcg attctgcgga gggatctccg tggggcggtg aacgccgatg attatataag    4260
gacgcgccgg ggtgtggcaca gctagttccg tcgcagccgg gatttgggtc gcggttcttg    4320
tttgtggatc gctgtgatcg tcacttggtg agttgcgggc tgctgggctg ccggggctt    4380
```

```
tcgtggccgc cgggccgctc ggtgggacgg aagcgtgtgg agagaccgcc aagggctgta    4440
gtctgggtcc gcgagcaagg ttgccctgaa ctgggggttg gggggagcgc acaaaatggc    4500
ggctgttccc gagtcttgaa tggaagacgc ttgtaaggcg ggctgtgagg tcgttgaaac    4560
aaggtggggg gcatggtggg cggcaagaac ccaaggtctt gaggccttcg ctaatgcggg    4620
aaagctctta ttcgggtgag atgggctggg gcaccatctg ggaccctga cgtgaagttt    4680 gtcactgact ggagaactcg ggtttgtcgt ctggttgcgg gggcggcagt tatgcggtgc    4740
cgttgggcag tgcacccgta cctttgggag cgcgcgcctc gtcgtgtcgt gacgtcaccc    4800
gttctgttgg cttataatgc agggtggggc cacctgccgg taggtgtgcg gtaggcttt    4860 ctccgtcgca ggacgcaggg ttcgggccta gggtaggctc tcctgaatcg acaggcgccg    4920
gacctctggt gaggggaggg ataagtgagg cgtcagtttc tttggtcggt tttatgtacc    4980
tatcttctta agtagctgaa gctccggttt tgaactatgc gctcggggtt ggcgagtgtg    5040
ttttgtgaag ttttttaggc accttttgaa atgtaatcat ttgggtcaat atgtaattt    5100 cagtgttaga ctagtaaatt gtccgctaaa ttctggccgt ttttggcttt tttgttagac    5160
gaagcttggg ctgcaggtcg actctagtgt aacgccacca tgaccgagta caagcctacc    5220
gtgaggctgg ccacccggga cgacgtgccc agagccgtga ggacactggc cgccgccttc    5280
gccgactacc ccgccacccg gcacaccgtg gaccccgacc ggcacatcga gcgggtgacc    5340
gagctgcagg aactgttcct gaccagagtg ggcctggata tcggcaaagt gtgggtggcc    5400
gacgacggag ccgccgtggc cgtgtggacc accccgagt ccgtggaggc cggagccgtg    5460
tttgccgaga tcggccccag gatggccgag ctgtccggca gcaggctggc cgcccagcag    5520
cagatggaag gcctgctggc ccctcaccgg cccaaagagc ccgcctggtt cctggccacc    5580
gtgggcgtga gccccgacca ccagggcaag ggcctgggca gcgccgtggt gctgccaggc    5640
gtggaagccg ccgagagggc cggagtgccc gccttcctgg aaaccagcgc ccccaggaac    5700
ctgcccttct acgagcggct gggctttacc gtgaccgccg acgtggaggt gccagagggc    5760
cccaggacct ggtgcatgac ccggaagcca ggcgcctgag aaaagcttat aacttcgtat    5820
aatgtatgct atacgaagtt ataacttgtt tattgcagct tataatggtt acaaataaag    5880
caatagcatc acaaatttca caaataaagc atttttttca ctgcattcta gttgtggttt    5940
gtccaaactc atcaatgtat cttatcatgt ctgtgcggtg ggctctatgg cttctgaggc    6000
ggaaagaacc agctggggct ctaggggta tcccctctag agtactaggg acaggattgg    6060
tgacagaaaa gccccatcct taggcctcct ccttcctagt ctcctgatat tgggtctaac    6120
ccccacctcc tgttaggcag attccttatc tggtgacaca ccccatttc ctggagccat    6180 ctctctcctt gccagaacct ctaaggtttg cttacgatgg agccagagag gatcctggga    6240
gggagagctt ggcaggggt gggagggaag gggggatgc gtgacctgcc cggttctcag    6300
tggccaccct gcgctaccct ctcccagaac ctgagctgct ctgacgcggc tgtctggtgc    6360
gtttcactga tcctggtgct gcagcttcct tacacttccc aagaggagaa gcagtttgga    6420
aaaacaaaat cagaataagt tggtcctgag ttctaacttt ggctcttcac ctttctagtc    6480
cccaatttat attgttcctc cgtgcgtcag ttttacctgt gagataaggc cagtagccag    6540
ccccgtcctg gcagggctgt ggtgaggagg ggggtgtccg tgtggaaaac tccctttgtg    6600
agaatggtgc gtcctaggtg ttcaccaggt cgtggccgcc tctactccct ttctctttct    6660
ccatccttct ttccttaaag agtccccagt gctatctggg acatattcct ccgcccagag    6720
```

| | |
|---|---|
| cagggtcccg cttccctaag gccctgctct gggcttctgg gtttgagtcc ttggcaagcc | 6780 |
| caggagaggc gctcaggctt ccctgtcccc cttcctcgtc caccatctca tgcccctggc | 6840 |
| tctcctgccc cttccctaca ggggttcctg gctctgctct tcagact | 6887 |

<210> SEQ ID NO 8
<211> LENGTH: 2497
<212> TYPE: DNA
<213> ORGANISM: Artificial Sequence
<220> FEATURE:
<223> OTHER INFORMATION: laboratory made

<400> SEQUENCE: 8

| | |
|---|---|
| ataacttcgt ataatgtatg ctatacgaag ttatggcgcg ccgaagttcc tattcttcta | 60 |
| gaagaatagg aacttccgaa taggaacttc ctgcacgtga acttgtttat tgcagcttat | 120 |
| aatggttaca aataaagcaa tagcatcaca aatttcacaa ataaagcatt ttttcactg | 180 |
| cattctagtt gtggtttgtc caaactcatc aatgtatctt atcatgtctg tgagctgaag | 240 |
| gtacgctgta tctcagtcag tcaagctagc tcaggtttag ttcctggtgt acttgagggg | 300 |
| gatgagttcc tcaatggtgg ttttgaccag cttgccattc atctcaatga gcacaaagca | 360 |
| gtcaggagca tagtcagaga tcagctctct acacatgcca caggggctga ccaccctgat | 420 |
| ggatctgtcc acctcatcag gtaggggtg cctgacagcc acaatggtgt caaagtcctt | 480 |
| ctgcccgttg ctcacagcag acccaatggc aatggcttca gcacagacag tgaccctgcc | 540 |
| aatgtaggct tcaatgtgga cagcagagat gatctcccca gtcttggtcc tgatggccgc | 600 |
| cccgacatgg tgcttgttgt cctcatagag catggtgatc ttctcagtgg cgacctccac | 660 |
| cagctccaga tcctgctgag agatgttgaa ggttttcatg ttgggatcca cgtggagctc | 720 |
| tgcttatata gacctcccac cgtacacgcc taccgcccat ttgcgtcaac ggggcggggt | 780 |
| tattacgaca ttttggaaag tcccgttgat tttggtgcca aaacaaactc ccattgacgt | 840 |
| caatggggtg gagacttgga atccccgtg agtcaaaccg ctatccacgc ccattggtgt | 900 |
| actgccaaaa ccgcatcacc atggtgaagt cctattctc tagaaagaat aggaacttcc | 960 |
| gaataggaac ttcggtacgg gaggtattgg acaggccgca ataaaatatc tttatttca | 1020 |
| ttacatctgt gtgttggttt tttgtgtgaa tcgatagtac taacatacgc tctccatcaa | 1080 |
| aacaaaacga aacaaaacaa actagcaaaa taggctgtcc ccagtgcaag tgcaggtgcc | 1140 |
| agaacatttc tctggcctaa ctggccggta cctgagctcg ctagcggagg aaaaactgtt | 1200 |
| tcatacagaa ggcgtggagg aaaaactgtt tcatacagaa ggcgtggagg aaaaactgtt | 1260 |
| tcatacagaa ggcgtagatc tagactctag agggtatata atggaagctc gaattccagc | 1320 |
| ttggcattcc ggtactgttg gtaaaaagct tggcaatccg gtactgcctg caggaccgcc | 1380 |
| atggctcagt cactggctct gagcctcctt atcctggttc tggcctttgg catcccagg | 1440 |
| acccaaggca gtgatggagg ggctcaggac tgttgcctca agtacagcca aggaagatt | 1500 |
| cccgccaagg ttgtccgcag ctaccggaag caggaaccaa gcttaggctg ctccatccca | 1560 |
| gctatcctgt tcttgccccg caagcgctct caggcagagc tatgtgcaga cccaaaggag | 1620 |
| ctctgggtgc agcagctgat gcagcatctg acaagacac catccccaca gaaaccagcc | 1680 |
| cagggctgca ggaaggacag gggggcctcc aagactggca agaaggaaa gggctccaaa | 1740 |
| ggctgcaaga ggactgagcg gtcacagacc cctaagaat cgcggccgc ggtcatagct | 1800 |
| gtttcctgaa cagatcccgg gtggcatccc tgtgacccct ccccagtgcc tctcctggcc | 1860 |
| ctggaagttg ccactccagt gcccaccagc cttgtcctaa taaaattaag ttgcatcatt | 1920 |

| | |
|---|---|
| ttgtctgact aggtgtcctt ctataatatt atggggtgga gggggtggt atggagcaag | 1980 |
| gggcaagttg ggaagacaac ctgtagggcc tgcggggtct attgggaacc aagctggagt | 2040 |
| gcagtggcac aatcttggct cactgcaatc tccgcctcct gggttcaagc gattctcctg | 2100 |
| cctcagcctc ccgagttgtt gggattccag gcatgcatga ccaggctcag ctaattttg | 2160 |
| ttttttggt agagacgggg tttcaccata ttggccaggc tggtctccaa ctcctaatct | 2220 |
| caggtgatct acccaccttg gcctcccaaa ttgctgggat tacaggcgtg aaccactgct | 2280 |
| cccttccctg tccttctgat tttaaaataa ctataccagc aggaggacgt ccagacacag | 2340 |
| cataggctac ctggccatgc ccaaccggtg ggacatttga gttgcttgct tggcactgtc | 2400 |
| ctctcatgcg ttgggtccac tcagtagatg cctgttgaat tgggtacgcg gccagcttaa | 2460 |
| tgcataactt cgtataatgt atgctatacg aagttat | 2497 |

```
<210> SEQ ID NO 9
<211> LENGTH: 1211
<212> TYPE: DNA
<213> ORGANISM: Artificial Sequence
<220> FEATURE:
<223> OTHER INFORMATION: laboratory made

<400> SEQUENCE: 9
```

| | |
|---|---|
| ggcctccgcg ccgggttttg gcgcctcccg cgggcgcccc cctcctcacg gcgagcgctg | 60 |
| ccacgtcaga cgaagggcgc aggagcgttc ctgatccttc cgcccggacg ctcaggacag | 120 |
| cggcccgctg ctcataagac tcggccttag aaccccagta tcagcagaag gacattttag | 180 |
| gacgggactt gggtgactct agggcactgg ttttctttcc agagagcgga acaggcgagg | 240 |
| aaaagtagtc ccttctcggc gattctgcgg agggatctcc gtgggcggt gaacgccgat | 300 |
| gattatataa ggacgcgccg ggtgtggcac agctagttcc gtcgcagccg ggatttgggt | 360 |
| cgcggttctt gtttgtggat cgctgtgatc gtcacttggt gagttgcggg ctgctgggct | 420 |
| ggccggggct ttcgtggccg ccgggccgct cggtgggacg gaagcgtgtg gagagaccgc | 480 |
| caagggctgt agtctgggtc gcgagcaag gttgccctga actggggtt gggggagcg | 540 |
| cacaaaatgg cggctgttcc cgagtcttga atggaagacg cttgtaaggc gggctgtgag | 600 |
| gtcgttgaaa caaggtgggg ggcatggtgg gcggcaagaa cccaaggtct tgaggccttc | 660 |
| gctaatgcgg gaaagctctt attcgggtga gatgggctgg ggcaccatct ggggaccctg | 720 |
| acgtgaagtt tgtcactgac tggagaactc gggtttgtcg tctggttgcg ggggcggcag | 780 |
| ttatgcggtc ccgttgggca gtgcacccgt acctttggga gcgcgcgcct cgtcgtgtcg | 840 |
| tgacgtcacc cgttctgttg gcttataatg cagggtgggg ccacctgccg gtaggtgtgc | 900 |
| ggtaggcttt tctccgtcgc aggacgcagg gttcgggcct agggtaggct ctcctgaatc | 960 |
| gacaggcgcc ggacctctgg tgaggggagg gataagtgag gcgtcagttt ctttggtcgg | 1020 |
| ttttatgtac ctatcttctt aagtagctga agctccggtt ttgaactatg cgctcggggt | 1080 |
| tggcgagtgt gttttgtgaa gtttttttagg cacctttga aatgtaatca tttgggtcaa | 1140 |
| tatgtaattt tcagtgttag actagtaaat tgtccgctaa attctggccg tttttggctt | 1200 |
| ttttgttaga c | 1211 |

```
<210> SEQ ID NO 10
<211> LENGTH: 500
<212> TYPE: DNA
<213> ORGANISM: Artificial Sequence
<220> FEATURE:
```

<223> OTHER INFORMATION: laboratory made

<400> SEQUENCE: 10

```
gggtagggga ggcgcttttc caaggcagt ctggagcatg cgctttagca gccccgctgg      60
gcacttggcg ctacacaagt ggcctctggc ctcgcacaca ttccacatcc accggtaggc     120
gccaaccggc tccgttcttt ggtggcccct tcgcgccacc ttctacccct ccctagtca     180
ggaagttccc cccgccccg cagctcgcgt catgcaggac gtgacaaatg aagtagcac      240
gtctcactag tctcgtgcaa atggacagca ccgctgagca atggaagcgg gtaggccctt    300
ggggcagcgg ccaatagcag ctttgctcct tcgctttctg ggctcagagg ctgggaaggg    360
gtgggtccgg gggcgggctc aggggcgggc tcaggggcgg ggcgggcgcc cgaaggtcct    420
ccggaggccc ggcattccgc acgcttcaaa agcgcacgtc tgccgcgctg ttctcttctt    480
cctcatctcc gggcctttcg                                                500
```

<210> SEQ ID NO 11
<211> LENGTH: 508
<212> TYPE: DNA
<213> ORGANISM: Artificial Sequence
<220> FEATURE:
<223> OTHER INFORMATION: laboratory made

<400> SEQUENCE: 11

```
cgttacataa cttacggtaa atggcccgcc tggctgaccg cccaacgacc cccgcccatt     60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catgctgatg cggttttggc agtacatcaa tgggcgtgga tagcggtttg actcacgggg    360
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagct                                       508
```

<210> SEQ ID NO 12
<211> LENGTH: 254
<212> TYPE: PRT
<213> ORGANISM: Artificial Sequence
<220> FEATURE:
<223> OTHER INFORMATION: laboratory made

<400> SEQUENCE: 12

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
```

```
            100                 105                 110
Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
                195                 200                 205

Val Ser Phe Cys Leu Val Met Val Leu Leu Phe Ala Val Asp Thr Gly
        210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 13
<211> LENGTH: 765
<212> TYPE: DNA
<213> ORGANISM: Artificial Sequence
<220> FEATURE:
<223> OTHER INFORMATION: laboratory made

<400> SEQUENCE: 13
atgtggcagc tgctgctgcc tacagctctc ctgctgctgg tgtccgccgg catgagaacc      60
gaggatctgc ctaaggccgt ggtgttcctg aaccccagt ggtacagagt gctggaaaag     120 acagcgtga ccctgaagtg ccagggcgcc tacagcccg aggacaatag cacccagtgg     180
ttccacaacg agagcctgat cagcagccag gccagcagct acttcatcga cgccgccacc    240
gtggacgaca cggcgagta tagatgccag accaacctga gcaccctgag cgaccccgtg    300
cagctggaag tgcacatcgg atggctgctg ctgcaggccc ccagatgggt gttcaaagaa    360
gaggacccca tccacctgag atgccactct tggaagaaca ccgccctgca caaagtgacc    420
tacctgcaga acggcaaggg cagaaagtac ttccaccaca cagcgactt ctacatcccc     480 aaggccaccc tgaaggactc cggctcctac ttctgcagag gctcgtggg cagcaagaac    540 gtgtccagcg agacagtgaa catcaccatc acccagggcc tggccgtgtc taccatcagc    600 agcttttttcc cacccggcta ccaggtgtcc ttctgcctcg tgatggtgct gctgttcgcc    660
gtggacaccg gcctgtactt cagcgtgaaa acaaacatca gaagcagcac ccgggactgg    720
aaggaccaca gttcaagtg gcggaaggac ccccaggaca agtga                     765

<210> SEQ ID NO 14
<211> LENGTH: 483
<212> TYPE: DNA
<213> ORGANISM: Artificial Sequence
<220> FEATURE:
<223> OTHER INFORMATION: laboratory made

<400> SEQUENCE: 14
atgtaccgga tgcagctgct gagctgtatc gccctgtctc tggccctcgt gaccaacagc     60
gcccctacca gcagcagcac caagaaaacc cagctgcagc tggaacatct gctgctggac    120
```

```
ctgcagatga tcctgaacgg catcaacaac tacaagaacc ccaagctgac ccggatgctg      180
accttcaagt tctacatgcc caagaaggcc accgaactga acatctgca gtgcctggaa       240 gaggaactga agcccctgga agaagtgctg aacctggccc agagcaagaa cttccacctg      300
aggcccaggg acctgatcag caacatcaac gtgatcgtgc tggaactgaa aggcagcgag      360
acaaccttca tgtgcgagta cgccgacgag acagctacca tcgtggaatt tctgaaccgg      420 tggatcaccct tctgccagag catcatcagc accctgaccg gctccgagaa ggacgagctg     480
tga                                                                   483
```

```
<210> SEQ ID NO 15
<211> LENGTH: 164
<212> TYPE: PRT
<213> ORGANISM: Artificial Sequence
<220> FEATURE:
<223> OTHER INFORMATION: laboratory made

<400> SEQUENCE: 15
```

| Met | Tyr | Arg | Met | Gln | Leu | Leu | Ser | Cys | Ile | Ala | Leu | Ser | Leu | Ala | Leu |
|---|---|---|---|---|---|---|---|---|---|---|---|---|---|---|---|
| 1 | | | | 5 | | | | | 10 | | | | | 15 | |

| Val | Thr | Asn | Ser | Ala | Pro | Thr | Ser | Ser | Ser | Thr | Lys | Lys | Thr | Gln | Leu |
|---|---|---|---|---|---|---|---|---|---|---|---|---|---|---|---|
| | | | 20 | | | | | 25 | | | | | 30 | | |

| Gln | Leu | Glu | His | Leu | Leu | Leu | Asp | Leu | Gln | Met | Ile | Leu | Asn | Gly | Ile |
|---|---|---|---|---|---|---|---|---|---|---|---|---|---|---|---|
| | | 35 | | | | | 40 | | | | | 45 | | | |

| Asn | Asn | Tyr | Lys | Asn | Pro | Lys | Leu | Thr | Arg | Met | Leu | Thr | Phe | Lys | Phe |
|---|---|---|---|---|---|---|---|---|---|---|---|---|---|---|---|
| | 50 | | | | | 55 | | | | | 60 | | | | |

| Tyr | Met | Pro | Lys | Lys | Ala | Thr | Glu | Leu | Lys | His | Leu | Gln | Cys | Leu | Glu |
|---|---|---|---|---|---|---|---|---|---|---|---|---|---|---|---|
| 65 | | | | | 70 | | | | | 75 | | | | | 80 |

| Glu | Glu | Leu | Lys | Pro | Leu | Glu | Glu | Val | Leu | Asn | Leu | Ala | Gln | Ser | Lys |
|---|---|---|---|---|---|---|---|---|---|---|---|---|---|---|---|
| | | | | 85 | | | | | 90 | | | | | 95 | |

| Asn | Phe | His | Leu | Arg | Pro | Arg | Asp | Leu | Ile | Ser | Asn | Ile | Asn | Val | Ile |
|---|---|---|---|---|---|---|---|---|---|---|---|---|---|---|---|
| | | | 100 | | | | | 105 | | | | | 110 | | |

| Val | Leu | Glu | Leu | Lys | Gly | Ser | Glu | Thr | Thr | Phe | Met | Cys | Glu | Tyr | Ala |
|---|---|---|---|---|---|---|---|---|---|---|---|---|---|---|---|
| | | | 115 | | | | | 120 | | | | | 125 | | |

| Asp | Glu | Thr | Ala | Thr | Ile | Val | Glu | Phe | Leu | Asn | Arg | Trp | Ile | Thr | Phe |
|---|---|---|---|---|---|---|---|---|---|---|---|---|---|---|---|
| | 130 | | | | | 135 | | | | | 140 | | | | |

| Cys | Gln | Ser | Ile | Ile | Ser | Thr | Leu | Thr | Gly | Ser | Glu | Lys | Asp | Glu | Leu |
|---|---|---|---|---|---|---|---|---|---|---|---|---|---|---|---|
| 145 | | | | | 150 | | | | | 155 | | | | | 160 |

| Lys | Asp | Glu | Leu |
|---|---|---|---|
| | | | |

```
<210> SEQ ID NO 16
<211> LENGTH: 297
<212> TYPE: DNA
<213> ORGANISM: Artificial Sequence
<220> FEATURE:
<223> OTHER INFORMATION: laboratory made

<400> SEQUENCE: 16
```

```
atggccctgc tactggccct cagcctgctg gttctctgga cttccccagc cccaactctg      60
agtggcacca atgatgctga agactgctgc ctgtctgtga cccagaaacc catccctggg      120
tacatcgtga ggaacttcca ctaccttctc atcaaggatg ctgcagggt gcctgctgta      180 gtgttcacca cactgagggg ccgccagctc tgtgcacccc agaccagcc ctgggtagaa       240 cgcatcatcc agagactgca gaggacctca gccaagatga gcgccgcag cagttaa          297
```

```
<210> SEQ ID NO 17
<211> LENGTH: 60
```

```
<212> TYPE: DNA
<213> ORGANISM: Artificial Sequence
<220> FEATURE:
<223> OTHER INFORMATION: laboratory made

<400> SEQUENCE: 17
cagtgcacca actacgccct gctgaagctg gccggcgacg tggagagcaa ccctggccct    60

<210> SEQ ID NO 18
<211> LENGTH: 54
<212> TYPE: DNA
<213> ORGANISM: Artificial Sequence
<220> FEATURE:
<223> OTHER INFORMATION: laboratory made

<400> SEQUENCE: 18
gagggcagag gcagcctgct gacctgcggc gatgtggagg aaaacccagg ccca          54

<210> SEQ ID NO 19
<211> LENGTH: 806
<212> TYPE: DNA
<213> ORGANISM: Artificial Sequence
<220> FEATURE:
<223> OTHER INFORMATION: laboratory made

<400> SEQUENCE: 19
tgctttctct gacctgcatt ctctcccctg ggcctgtgcc gctttctgtc tgcagcttgt    60
ggcctgggtc acctctacgg ctggcccaga tccttccctg ccgcctcctt caggttccgt   120
cttcctccac tccctcttcc ccttgctctc tgctgtgttg ctgcccaagg atgtctcttc   180
cggagcactt ccttctcggc gctgcaccac gtgatgtcct ctgagcggat cctccccgtg   240
tctgggtcct ctccgggcat ctctcctccc tcacccaacc ccatgccgtc ttcactcgct   300
gggttccctt ttccttctcc ttctggggcc tgtgccatct ctcgtttctt aggatggcct   360
tctccgacgg atgtctccct tgcgtcccgc ctccccttct tgtaggcctg catcatcacc   420 gttttttctgg acaaccccaa agtaccccgt ctccctggct ttagccacct ctccatcctc   480
ttgctttctt tgcctggaca ccccgttctc ctgtggattc gggtcacctc tcactccttt   540
catttgggca gctcccctac ccccccttacc tctctagtct gtgctagctc ttccagcccc   600
ctgtcatggc atcttccagg ggtccgagag ctcagctagt cttcttcctc caacccgggc   660
ccctatgtcc acttcaggac agcatgtttg ctgcctccag ggatcctgtg tccccgagct   720
gggaccacct tatattccca gggccggtta atgtggctct ggttctgggt actttatct    780 gtcccctcca ccccacagtg gggtac                                       806

<210> SEQ ID NO 20
<211> LENGTH: 1178
<212> TYPE: DNA
<213> ORGANISM: Artificial Sequence
<220> FEATURE:
<223> OTHER INFORMATION: Laboratory made

<400> SEQUENCE: 20
gctccggtgc ccgtcagtgg gcagagcgca catcgcccac agtccccgag aagttggggg    60
gaggggtcgg caattgaacc ggtgcctaga gaaggtggcg cggggtaaac tgggaaagtg   120
atgtcgtgta ctggctccgc cttttttccg agggtggggg agaaccgtat ataagtgcag   180
tagtcgccgt gaacgttctt tttcgcaacg ggtttgccgc cagaacacag gtaagtgccg   240
tgtgtggttc ccgcgggcct ggcctcttta cgggttatgg cccttgcgtg ccttgaatta   300
```

-continued

| | |
|---|---|
| cttccacctg gctgcagtac gtgattcttg atcccgagct tcgggttgga agtgggtggg | 360 |
| agagttcgag gccttgcgct taaggagccc cttcgcctcg tgcttgagtt gaggcctggc | 420 |
| ctgggcgctg gggccgccgc gtgcgaatct ggtggcacct tcgcgcctgt ctcgctgctt | 480 |
| tcgataagtc tctagccatt taaaattttt gatgacctgc tgcgacgctt tttttctggc | 540 |
| aagatagtct tgtaaatgcg ggccaagatc tgcacactgg tatttcggtt tttggggccg | 600 |
| cgggcggcga cggggcccgt gcgtcccagc gcacatgttc ggcgaggcgg ggcctgcgag | 660 |
| cgcggccacc gagaatcgga cggggggtagt ctcaagctgg ccggcctgct ctggtgcctg | 720 |
| gcctcgcgcc gccgtgtatc gccccgcccct gggcggcaag gctggcccgg tcggcaccag | 780 |
| ttgcgtgagc ggaaagatgg ccgcttcccg gccctgctgc agggagctca aaatggagga | 840 |
| cgcggcgctc gggagagcgg gcgggtgagt cacccacaca aggaaaagg gcctttccgt | 900 |
| cctcagccgt cgcttcatgt gactccacgg agtaccgggc gccgtccagg cacctcgatt | 960 |
| agttctcgag cttttggagt acgtcgtctt taggttgggg ggagggggttt tatgcgatgg | 1020 |
| agtttcccca cactgagtgg gtggagactg aagttaggcc agcttggcac ttgatgtaat | 1080 |
| tctccttgga atttgcccctt tttgagtttg gatcttggtt cattctcaag cctcagacag | 1140 |
| tggttcaaag tttttttctt ccatttcagg tgtcgtga | 1178 |

```
<210> SEQ ID NO 21
<211> LENGTH: 19
<212> TYPE: DNA
<213> ORGANISM: Artificial Sequence
<220> FEATURE:
<223> OTHER INFORMATION: laboratory made

<400> SEQUENCE: 21
```

| | |
|---|---|
| taatacgact cactatagg | 19 |

```
<210> SEQ ID NO 22
<211> LENGTH: 1116
<212> TYPE: DNA
<213> ORGANISM: Artificial Sequence
<220> FEATURE:
<223> OTHER INFORMATION: laboratory made

<400> SEQUENCE: 22
```

| | |
|---|---|
| atgaaaagcg tgctggtggt ggctctcctt gtcatttttcc aggtatgcct gtgtcaagat | 60 |
| gaggtcacgg acgattacat cggagacaac accacagtgg actacacttt gttcgagtct | 120 |
| ttgtgctcca agaaggacgt gcggaacttt aaagcctggt tcctcccctat catgtactcc | 180 |
| atcatttgtt tcgtgggcct actgggcaat gggctggtcg tgttgaccta tatctatttc | 240 |
| aagaggctca agaccatgac cgataccttac ctgctcaacc tggcggtggc agacatcctc | 300 |
| ttcctcctga cccttcccctt ctgggcctac agcgcggcca agtcctgggt cttcggtgtc | 360 |
| cacttttgca agctcatctt tgccatctac aagatgagct tcttcagtgg catgctccta | 420 |
| cttctttgca tcagcattga ccgctacgtg gccatcgtcc aggctgtctc agctcaccgc | 480 |
| caccgtgccc gcgtccttct catcagcaag ctgtcctgtg tgggcatctg gatactagcc | 540 |
| acagtgctct ccatcccaga gctcctgtac agtgacctcc agaggagcag cagtgagcaa | 600 |
| gcgatgcgat gctctctcat cacagagcat gtggaggcct ttatcaccat ccaggtggcc | 660 |
| cagatggtga tcggctttct ggtccccctg ctgccatga gcttctgtta ccttgtcatc | 720 |
| atccgcaccc tgctccaggc acgcaacttt gagcgcaaca aggccatcaa ggtgatcatc | 780 |
| gctgtggtcg tggtcttcat agtcttccag ctgccctaca atgggggtgg cctggcccag | 840 |

```
acggtggcca acttcaacat caccagtagc acctgtgagc tcagtaagca actcaacatc    900
gcctacgacg tcacctacag cctggcctgc gtccgctgct gcgtcaaccc tttcttgtac    960
gccttcatcg gcgtcaagtt ccgcaacgat ctcttcaagc tcttcaagga cctgggctgc   1020
ctcagccagg agcagctccg gcagtggtct tcctgtcggc acatccggcg ctcctccatg   1080
agtgtggagg ccgagaccac caccaccttc tcccca                             1116
```

<210> SEQ ID NO 23
<211> LENGTH: 66
<212> TYPE: DNA
<213> ORGANISM: Artificial Sequence
<220> FEATURE:
<223> OTHER INFORMATION: laboratory made

<400> SEQUENCE: 23

```
ggatctggag ctactaactt cagcctgctg aagcaggctg agacgtggag ggagaaccct     60
ggacct                                                                66
```

<210> SEQ ID NO 24
<211> LENGTH: 69
<212> TYPE: DNA
<213> ORGANISM: Artificial Sequence
<220> FEATURE:
<223> OTHER INFORMATION: laboratory made

<400> SEQUENCE: 24

```
atggactgga tctggcggat tctgtttctc gtgggagctg ccacaggcgc tcattctgct     60
cagcctgcc                                                             69
```

<210> SEQ ID NO 25
<211> LENGTH: 1152
<212> TYPE: DNA
<213> ORGANISM: Artificial Sequence
<220> FEATURE:
<223> OTHER INFORMATION: laboratory made

<400> SEQUENCE: 25

```
gatatccaga tgacccagac aacaagcagc ctgagcgcct ctctgggcga tagagtgaca     60
atcagctgca gagccagcca ggacatcagc aagtacctga actggtatca gcagaaaccc    120
gacggcaccg tgaagctgct gatctaccac acaagcagac tgcacagcgg cgtgccaagc    180
agattttctg gcagcggcag cggcaccgat tacagcctga ccatcagcaa cctggaacag    240
gaagatatcg ctacctactt ctgtcagcag ggcaacaccc tgccttacac ctttggcggc    300
ggaacaaagc tggaactgaa agaggcggc ggaggaagcg gaggcggagg atctggggc     360 ggaggctctg gcgaggggg atctgaagtg cagctgcagc agtctggacc tggactggtg    420
gctccttctc agtccctgtc tgtgacctgt acagtgtctg gcgtgtccct gcctgattac    480
ggcgtgtcct ggatcagaca gcctcccaga aaaggcctgg aatggctggg agtgatctgg    540
ggcagcgaga caacctacta caacagcgcc ctgaagtccc ggctgaccat catcaaggac    600
aacagcaaga gccaggtgtt cctgaagatg aacagcctgc agaccgacga caccgccatc    660
tactactgcg ccaagcacta ctactacggc ggcagctacg ccatggatta ttggggccag    720
ggcaccaccg tgacagtgtc atctgcggcc gcgctgagca acagcatcat gtacttcagc    780
cacttcgtgc ctgtgttcct gcctgccaag cctacaacaa caccagcccc tagacctcca    840
acccctgccc ctacaattgc ctctcagcct ctgtctctga ggcccgaagc ttgtagacct    900
```

-continued

```
gctgctggcg gagctgtgca caccagagga ctggatttcg cctgcttttg ggtgctggtg    960
gtcgtgggcg gagtgctggc ttgttattct ctgctggtca ccgtggcctt catcatcttt   1020
tgggtccgac tgaagatcca ggtccgaaag gccgccatca ccagctacga aagtctgat    1080 ggcgtgtaca ccggcctgag caccagaaac caggaaacct acgagacact gaagcacgag   1140
aagccccccc ag                                                       1152
```

<210> SEQ ID NO 26
<211> LENGTH: 765
<212> TYPE: DNA
<213> ORGANISM: Artificial Sequence
<220> FEATURE:
<223> OTHER INFORMATION: laboratory made

<400> SEQUENCE: 26

```
atgtggcagc tgctgctgcc tacagctctc ctgctgctgg tgtccgccgg catgagaacc     60
gaggatctgc ctaaggccgt ggtgttcctg aaccccagt ggtacagagt gctggaaaag    120
gacagcgtga ccctgaagtg ccagggcgcc tacagccccg aggacaatag cacccagtgg   180
ttccacaacg agagcctgat cagcagccag gccagcagct acttcatcga cgccgccacc   240
gtggacgaca gcgcgagta tagatgccag accaacctga gcaccctgag cgaccccgtg    300
cagctggaag tgcacatcgg atggctgctg ctgcaggccc ccagatgggt gttcaaagaa    360
gaggacccca tccacctgag atgccactct tggaagaaca ccgccctgca aaagtgacc    420 tacctgcaga acggcaaggg cagaaagtac ttccaccaca acagcgactt ctacatcccc    480
aaggccaccc tgaaggactc cggctcctac ttctgcagag gctcgtggg cagcaagaac    540 gtgtccagcg agacagtgaa catcaccatc acccagggcc tggccgtgtc taccatcagc    600 agcttttttcc cacccggcta ccaggtgtcc ttctgcctcg tgatggtgct gctgttcgcc    660
gtggacaccg gcctgtactt cagcgtgaaa acaaacatca gaagcagcac ccgggactgg    720
aaggaccaca agttcaagtg gcggaaggac ccccaggaca gtga                    765
```

<210> SEQ ID NO 27
<211> LENGTH: 597
<212> TYPE: DNA
<213> ORGANISM: Artificial Sequence
<220> FEATURE:
<223> OTHER INFORMATION: laboratory made

<400> SEQUENCE: 27

```
aattccgccc ctctcccccc ccccctctc cctcccccc cctaacgtt actggccgaa      60 gccgcttgga ataaggccgg tgtgcgtttg tctatatgtt attttccacc atattgccgt    120
cttttggcaa tgtgagggcc cggaaacctg gccctgtctt cttgacgagc attcctaggg   180
gtctttcccc tctcgccaaa ggaatgcaag gtctgttgaa tgtcgtgaag gaagcagttc    240
ctctggaagc ttcttgaaga caaacaacgt ctgtagcgac cctttgcagg cagcggaacc    300
ccccacctgg cgacaggtgc ctctgcggcc aaaagccacg tgtataagat acacctgcaa   360
aggcggcaca ccccagtgc cacgttgtga gttggatagt tgtggaaaga gtcaaatggc    420
tctcctcaag cgtattcaac aaggggctga aggatgccca gaaggtaccc cattgtatgg    480
gatctgatct ggggcctcgg tgcacatgct ttacatgtgt ttagtcgagg ttaaaaaaac    540
gtctaggccc cccgaaccac ggggacgtgg ttttccttgg aaaaacacga taaccgc      597
```

<210> SEQ ID NO 28
<211> LENGTH: 483

<212> TYPE: DNA
<213> ORGANISM: Artificial Sequence
<220> FEATURE:
<223> OTHER INFORMATION: laboratory made

<400> SEQUENCE: 28

```
atgtaccgga tgcagctgct gagctgtatc gccctgtctc tggccctcgt gaccaacagc    60
gcccctacca gcagcagcac caagaaaacc cagctgcagc tggaacatct gctgctggac   120
ctgcagatga tcctgaacgg catcaacaac tacaagaacc ccaagctgac ccggatgctg   180
accttcaagt tctacatgcc caagaaggcc accgaactga acatctgca gtgcctggaa    240
gaggaactga agcccctgga agaagtgctg aacctggccc agagcaagaa cttccacctg   300
aggcccaggg acctgatcag caacatcaac gtgatcgtgc tggaactgaa aggcagcgag   360
acaaccttca tgtgcgagta cgccgacgag acagctacca tcgtggaatt tctgaaccgg   420
tggatcaccct tctgccagag catcatcagc accctgaccg gctccgagaa ggacgagctg   480
tga                                                                  483
```

<210> SEQ ID NO 29
<211> LENGTH: 252
<212> TYPE: DNA
<213> ORGANISM: Artificial Sequence
<220> FEATURE:
<223> OTHER INFORMATION: laboratory made

<400> SEQUENCE: 29

```
acgagatttc gattccaccg ccgccttcta tgaaaggttg ggcttcggaa tcgtttttccg    60
ggacgccggc tggatgatcc tccagcgcgg ggatctcatg ctggagttct tcgcccaccc   120
caacttgttt attgcagctt ataatggtta caaataaagc aatagcatca caaatttcac   180
aaataaagca tttttttcac tgcattctag ttgtggtttg tccaaactca tcaatgtatc   240
ttatcatgtc tg                                                        252
```

<210> SEQ ID NO 30
<211> LENGTH: 844
<212> TYPE: DNA
<213> ORGANISM: Artificial Sequence
<220> FEATURE:
<223> OTHER INFORMATION: laboratory made

<400> SEQUENCE: 30

```
ctagggacag gattggtgac agaaaagccc catccttagg cctcctcctt cctagtctcc    60
tgatattggg tctaaccccc acctcctgtt aggcagattc cttatctggt gacacacccc   120
catttcctgg agccatctct ctccttgcca gaacctctaa ggtttgctta cgatggagcc   180
agagaggatc ctgggaggga gagcttggca ggggtgggga gggaagggggg ggatgcgtga   240
cctgcccggt tctcagtggc caccctgcgc taccctctcc cagaacctga gctgctctga   300
cgcggctgtc tggtgcgttt cactgatcct ggtgctgcag cttccttaca cttcccaaga   360
ggagaagcag tttggaaaaa caaaatcaga ataagttggt cctgagttct aactttggct   420
cttcaccttt ctagtcccca atttatattg ttcctccgtg cgtcagtttt acctgtgaga   480
taaggccagt agccagcccc gtcctggcag ggctgtggtg aggaggggggg tgtccgtgtg   540
gaaaactccc tttgtgagaa tggtgcgtcc taggtgttca ccaggtcgtg gccgcctcta   600
ctcccttttct ctttctccat ccttcttttcc ttaaagagtc cccagtgcta tctgggacat   660
attcctccgc ccagagcagg gtcccgcttc cctaaggccc tgctctgggc ttctgggttt   720
```

```
gagtccttgg caagcccagg agaggcgctc aggcttccct gtccccttc ctcgtccacc      780 atctcatgcc cctggctctc ctgccccttc cctacagggg ttcctggctc tgctcttcag      840
actg                                                                   844
```

```
<210> SEQ ID NO 31
<211> LENGTH: 41
<212> TYPE: PRT
<213> ORGANISM: Artificial Sequence
<220> FEATURE:
<223> OTHER INFORMATION: laboratory made

<400> SEQUENCE: 31
```

Leu Lys Ile Gln Val Arg Lys Ala Ala Ile Thr Ser Tyr Glu Lys Ser
1               5                   10                  15

Asp Gly Val Tyr Thr Gly Leu Ser Thr Arg Asn Gln Glu Thr Tyr Glu
            20                  25                  30

Thr Leu Lys His Glu Lys Pro Pro Gln
        35                  40

```
<210> SEQ ID NO 32
<211> LENGTH: 123
<212> TYPE: DNA
<213> ORGANISM: Artificial Sequence
<220> FEATURE:
<223> OTHER INFORMATION: laboratory made

<400> SEQUENCE: 32
ctgaagatcc aggtccgaaa ggccgccatc accagctacg agaagtctga tggcgtgtac      60
accggcctga gcaccagaaa ccaggaaacc tacgagacac tgaagcacga aagccccccc      120
cag                                                                    123
```

```
<210> SEQ ID NO 33
<211> LENGTH: 64
<212> TYPE: PRT
<213> ORGANISM: Artificial Sequence
<220> FEATURE:
<223> OTHER INFORMATION: laboratory made

<400> SEQUENCE: 33
```

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60

```
<210> SEQ ID NO 34
<211> LENGTH: 192
<212> TYPE: DNA
<213> ORGANISM: Artificial Sequence
<220> FEATURE:
<223> OTHER INFORMATION: laboratory made

<400> SEQUENCE: 34
ctgagcaaca gcatcatgta cttcagccac ttcgtgcctg tgttcctgcc tgccaagcct      60
acaacaacac cagcccctag acctccaacc cctgccccta caattgcctc tcagcctctg      120
tctctgaggc ccgaagcttg tagacctgct gctggcggag ctgtgcacac cagaggactg      180
```

```
gatttcgcct gc                                                          192
```

<210> SEQ ID NO 35
<211> LENGTH: 28
<212> TYPE: PRT
<213> ORGANISM: Artificial Sequence
<220> FEATURE:
<223> OTHER INFORMATION: laboratory made

<400> SEQUENCE: 35

Phe Trp Val Leu Val Val Val Gly Gly Val Leu Ala Cys Tyr Ser Leu
1               5                   10                  15

Leu Val Thr Val Ala Phe Ile Ile Phe Trp Val Arg
            20                  25

<210> SEQ ID NO 36
<211> LENGTH: 84
<212> TYPE: DNA
<213> ORGANISM: Artificial Sequence
<220> FEATURE:
<223> OTHER INFORMATION: laboratory made

<400> SEQUENCE: 36

```
ttttgggtgc tggtggtcgt gggcggagtg ctggcttgtt attctctgct ggtcaccgtg    60
gccttcatca tcttttgggt ccga                                           84
```

<210> SEQ ID NO 37
<211> LENGTH: 133
<212> TYPE: PRT
<213> ORGANISM: Artificial Sequence
<220> FEATURE:
<223> OTHER INFORMATION: laboratory made

<400> SEQUENCE: 37

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60

Phe Trp Val Leu Val Val Val Gly Gly Val Leu Ala Cys Tyr Ser Leu
65                  70                  75                  80

Leu Val Thr Val Ala Phe Ile Ile Phe Trp Val Arg Leu Lys Ile Gln
                85                  90                  95

Val Arg Lys Ala Ala Ile Thr Ser Tyr Glu Lys Ser Asp Gly Val Tyr
            100                 105                 110

Thr Gly Leu Ser Thr Arg Asn Gln Glu Thr Tyr Glu Thr Leu Lys His
        115                 120                 125

Glu Lys Pro Pro Gln
    130

<210> SEQ ID NO 38
<211> LENGTH: 399
<212> TYPE: DNA
<213> ORGANISM: Artificial Sequence
<220> FEATURE:
<223> OTHER INFORMATION: laboratory made

<400> SEQUENCE: 38

-continued

```
ctgagcaaca gcatcatgta cttcagccac ttcgtgcctg tgttcctgcc tgccaagcct      60
acaacaacac cagcccctag acctccaacc cctgcccctg caattgcctc tcagcctctg     120
tctctgaggc ccgaagcttg tagacctgct gctggcggag ctgtgcacac cagaggactg     180
gatttcgcct gcttttgggt gctggtggtc gtgggcggag tgctggcttg ttattctctg     240
ctggtcaccg tggccttcat catcttttgg gtccgactga agatccaggt ccgaaaggcc     300
gccatcacca gctacgagaa gtctgatggc gtgtacaccg gcctgagcac cagaaaccag     360
gaaacctacg agacactgaa gcacgagaag ccccccccag                          399
```

<210> SEQ ID NO 39
<211> LENGTH: 252
<212> TYPE: PRT
<213> ORGANISM: Artificial Sequence
<220> FEATURE:
<223> OTHER INFORMATION: laboratory made

<400> SEQUENCE: 39

```
Ala Gln Pro Ala Asp Ile Gln Met Thr Gln Thr Thr Ser Ser Leu Ser
1               5                   10                  15

Ala Ser Leu Gly Asp Arg Val Thr Ile Ser Cys Arg Ala Ser Gln Asp
            20                  25                  30

Ile Ser Lys Tyr Leu Asn Trp Tyr Gln Gln Lys Pro Asp Gly Thr Val
        35                  40                  45

Lys Leu Leu Ile Tyr His Thr Ser Arg Leu His Ser Gly Val Pro Ser
    50                  55                  60

Arg Phe Ser Gly Ser Gly Ser Gly Thr Asp Tyr Ser Leu Thr Ile Ser
65                  70                  75                  80

Asn Leu Glu Gln Glu Asp Ile Ala Thr Tyr Phe Cys Gln Gln Gly Asn
                85                  90                  95

Thr Leu Pro Tyr Thr Phe Gly Gly Gly Thr Lys Leu Glu Leu Lys Arg
            100                 105                 110

Gly Gly Gly Gly Ser Gly Gly Gly Ser Gly Gly Gly Ser
        115                 120                 125

Gly Gly Gly Ser Glu Val Gln Leu Gln Gln Ser Gly Pro Gly Leu Val
    130                 135                 140

Ala Pro Ser Gln Ser Leu Ser Val Thr Cys Thr Val Ser Gly Val Ser
145                 150                 155                 160

Leu Pro Asp Tyr Gly Val Ser Trp Ile Arg Gln Pro Pro Arg Lys Gly
                165                 170                 175

Leu Glu Trp Leu Gly Val Ile Trp Gly Ser Glu Thr Thr Tyr Tyr Asn
            180                 185                 190

Ser Ala Leu Lys Ser Arg Leu Thr Ile Ile Lys Asp Asn Ser Lys Ser
        195                 200                 205

Gln Val Phe Leu Lys Met Asn Ser Leu Gln Thr Asp Asp Thr Ala Ile
    210                 215                 220

Tyr Tyr Cys Ala Lys His Tyr Tyr Gly Gly Ser Tyr Ala Met Asp
225                 230                 235                 240

Tyr Trp Gly Gln Gly Thr Thr Val Thr Val Ser Ser
                245                 250
```

<210> SEQ ID NO 40
<211> LENGTH: 113
<212> TYPE: PRT
<213> ORGANISM: Artificial Sequence
<220> FEATURE:
<223> OTHER INFORMATION: laboratory made

<400> SEQUENCE: 40

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 41
<211> LENGTH: 1410
<212> TYPE: DNA
<213> ORGANISM: Artificial Sequence
<220> FEATURE:
<223> OTHER INFORMATION: laboratory made

<400> SEQUENCE: 41
atggactgga tctggcggat cctgtttctc gtgggagctg ccacaggcgc tcattctgct     60
cagcctgccg atatccagat gacccagaca caagcagcc tgagcgcctc tctgggcgat    120
agagtgacaa tcagctgcag agccagccag gacatcagca gtacctgaa ctggtatcag    180 cagaaacccg acggcaccgt gaagctgctg atctaccaca agcagact gcacagcggc    240 gtgccaagca gattttctgg cagcggcagc ggcaccgatt acagcctgac catcagcaac    300
ctggaacagg aagatatcgc tacctacttc tgtcagcaag caacaccct gccttacacc    360 tttggcggcg aacaaagct ggaactgaaa agaggcggcg aggaagcgg aggcggagga    420 tctgggggcg aggctctgg cggaggggga tctgaagtgc agctgcagca gtctggacct    480
ggactggtgg ctccttctca gtccctgtct gtgacctgta cagtgtctgg cgtgtccctg    540
cctgattacg gcgtgtcctg gatcagacag cctcccagaa aaggcctgga atggctggga    600
gtgatctggg gcagcgagac aacctactac aacagcgccc tgaagtcccg gctgaccatc    660
atcaaggaca cagcaagag ccaggtgttc ctgaagatga cagcctgca gaccgacgac    720 accgccatct actactgcgc caagcactac tactacggcg gcagctacgc catggattat    780
tggggccagg gcaccaccgt gacagtgtca tctgctgctg ctctgttcgt gcctgtgttc    840
ctgcctgcca gcctacaac aacaccagcc cctagacctc aaccctgc ccctacaatt    900 gcctctcagc ctctgtctct gaggcccgaa gcttgtagac tgctgctgg cggagctgtg    960 cacaccagag gactggattt cgcctgcttt tgggtgctgg tggtcgtggg cggagtgctg   1020
gcttgttatt ctctgctggt caccgtggcc ttcatcatct ttgggtccg agtgaagttc   1080 agcagatccg ccgatgcccc tgcttaccag cagggccaga tcagctgta caacgagctg   1140 aacctgggca gacgggaaga gtacgacgtg ctggataaga gaagaggcag agatcccgag   1200
atgggcggca gccccagag aagaaagaat ccccaggaag cctgtataa cgaactgcag   1260 aaagacaaga tggccgaggc ctacagcgag atcggcatga agggcgagag aagaagaggc   1320

```
aagggccacg atggactgta ccagggactg agcacagcca ccaaggatac ctacgatgcc   1380
ctgcacatgc aggccctgcc tccaagataa                                    1410
```

<210> SEQ ID NO 42
<211> LENGTH: 153
<212> TYPE: PRT
<213> ORGANISM: Artificial Sequence
<220> FEATURE:
<223> OTHER INFORMATION: laboratory made

<400> SEQUENCE: 42

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 43
<211> LENGTH: 160
<212> TYPE: PRT
<213> ORGANISM: Artificial Sequence
<220> FEATURE:
<223> OTHER INFORMATION: laboratory made

<400> SEQUENCE: 43

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125
```

Asp Glu Thr Ala Thr Ile Val Glu Phe Leu Asn Arg Trp Ile Thr Phe
    130                 135                 140

Cys Gln Ser Ile Ile Ser Thr Leu Thr Gly Ser Glu Lys Asp Glu Leu
145                 150                 155                 160

<210> SEQ ID NO 44
<211> LENGTH: 372
<212> TYPE: PRT
<213> ORGANISM: Artificial Sequence
<220> FEATURE:
<223> OTHER INFORMATION: laboratory made

<400> SEQUENCE: 44

Met Lys Ser Val Leu Val Val Ala Leu Leu Val Ile Phe Gln Val Cys
1               5                   10                  15

Leu Cys Gln Asp Glu Val Thr Asp Asp Tyr Ile Gly Asp Asn Thr Thr
                20                  25                  30

Val Asp Tyr Thr Leu Phe Glu Ser Leu Cys Ser Lys Lys Asp Val Arg
            35                  40                  45

Asn Phe Lys Ala Trp Phe Leu Pro Ile Met Tyr Ser Ile Ile Cys Phe
    50                  55                  60

Val Gly Leu Leu Gly Asn Gly Leu Val Val Leu Thr Tyr Ile Tyr Phe
65                  70                  75                  80

Lys Arg Leu Lys Thr Met Thr Asp Thr Tyr Leu Leu Asn Leu Ala Val
                85                  90                  95

Ala Asp Ile Leu Phe Leu Leu Thr Leu Pro Phe Trp Ala Tyr Ser Ala
                100                 105                 110

Ala Lys Ser Trp Val Phe Gly Val His Phe Cys Lys Leu Ile Phe Ala
            115                 120                 125

Ile Tyr Lys Met Ser Phe Phe Ser Gly Met Leu Leu Leu Leu Cys Ile
    130                 135                 140

Ser Ile Asp Arg Tyr Val Ala Ile Val Gln Ala Val Ser Ala His Arg
145                 150                 155                 160

His Arg Ala Arg Val Leu Leu Ile Ser Lys Leu Ser Cys Val Gly Ile
                165                 170                 175

Trp Ile Leu Ala Thr Val Leu Ser Ile Pro Glu Leu Leu Tyr Ser Asp
            180                 185                 190

Leu Gln Arg Ser Ser Ser Glu Gln Ala Met Arg Cys Ser Leu Ile Thr
    195                 200                 205

Glu His Val Glu Ala Phe Ile Thr Ile Gln Val Ala Gln Met Val Ile
210                 215                 220

Gly Phe Leu Val Pro Leu Leu Ala Met Ser Phe Cys Tyr Leu Val Ile
225                 230                 235                 240

Ile Arg Thr Leu Leu Gln Ala Arg Asn Phe Glu Arg Asn Lys Ala Ile
                245                 250                 255

Lys Val Ile Ile Ala Val Val Val Phe Ile Val Phe Gln Leu Pro
                260                 265                 270

Tyr Asn Gly Val Val Leu Ala Gln Thr Val Ala Asn Phe Asn Ile Thr
            275                 280                 285

Ser Ser Thr Cys Glu Leu Ser Lys Gln Leu Asn Ile Ala Tyr Asp Val
    290                 295                 300

Thr Tyr Ser Leu Ala Cys Val Arg Cys Cys Val Asn Pro Phe Leu Tyr
305                 310                 315                 320

Ala Phe Ile Gly Val Lys Phe Arg Asn Asp Leu Phe Lys Leu Phe Lys
                325                 330                 335

Asp Leu Gly Cys Leu Ser Gln Glu Gln Leu Arg Gln Trp Ser Ser Cys
             340                 345                 350

Arg His Ile Arg Arg Ser Ser Met Ser Val Glu Ala Glu Thr Thr Thr
             355                 360                 365

Thr Phe Ser Pro
    370

<210> SEQ ID NO 45
<211> LENGTH: 98
<212> TYPE: PRT
<213> ORGANISM: Artificial Sequence
<220> FEATURE:
<223> OTHER INFORMATION: laboratory made

<400> SEQUENCE: 45

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 46
<211> LENGTH: 134
<212> TYPE: PRT
<213> ORGANISM: Artificial Sequence
<220> FEATURE:
<223> OTHER INFORMATION: laboratory made

<400> SEQUENCE: 46

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 47
<211> LENGTH: 1083

<212> TYPE: DNA
<213> ORGANISM: Artificial Sequence
<220> FEATURE:
<223> OTHER INFORMATION: laboratory made

<400> SEQUENCE: 47

```
atggaagatt ttaacatgga gagtgacagc tttgaagatt tctggaaagg tgaagatctt      60
agtaattaca gttacagctc taccctgccc ccttttctac tagatgccgc cccatgtgaa     120
ccagaatccc tggaaatcaa caagtatttt gtggtcatta tctatgccct ggtattcctg     180
ctgagcctgc tgggaaactc cctcgtgatg ctggtcatct atacagcag gtcggccgc       240
tccgtcactg atgtctacct gctgaaccta gccttggccg acctactctt tgccctgacc     300
ttgcccatct gggccgcctc caaggtgaat ggctggattt ttggcacatt cctgtgcaag     360
gtggtctcac tcctgaagga agtcaacttc tatagtggca tcctgctact ggcctgcatc     420
agtgtggacc gttacctggc cattgtccat gccacacgca cactgaccca gaagcgctac     480
ttggtcaaat tcatatgtct cagcatctgg ggtctgtcct tgctcctggc cctgcctgtc     540
ttacttttcc gaaggaccgt ctactcatcc aatgttagcc cagcctgcta tgaggacatg     600
ggcaacaata cagcaaactg gcggatgctg ttacggatcc tgccccagtc ctttggcttc     660
atcgtgccac tgctgatcat gctgttctgc tacggattca ccctgcgtac gctgtttaag     720
gcccacatgg ggcagaagca ccgggccatg cgggtcatct ttgctgtcgt cctcatcttc     780
ctgctctgct ggctgcccta caacctggtc ctgctggcag acaccctcat gaggacccag     840
gtgatccagg agacctgtga gcgccgcaat cacatcgacc gggctctgga tgccaccgag     900
attctgggca tccttcacag ctgcctcaac ccctcatct acgccttcat ggccagaag      960
tttcgccatg gactcctcaa gattctagct atacatggct tgatcagcaa ggactccctg    1020
cccaaagaca gcaggccttc ctttgttggc tcttcttcag ggcacacttc cactactctc    1080
taa                                                                   1083
```

<210> SEQ ID NO 48
<211> LENGTH: 360
<212> TYPE: PRT
<213> ORGANISM: Artificial Sequence
<220> FEATURE:
<223> OTHER INFORMATION: laboratory made

<400> SEQUENCE: 48

```
Met Glu Asp Phe Asn Met Glu Ser Asp Ser Phe Glu Asp Phe Trp Lys
1               5                   10                  15
Gly Glu Asp Leu Ser Asn Tyr Ser Tyr Ser Ser Thr Leu Pro Pro Phe
            20                  25                  30
Leu Leu Asp Ala Ala Pro Cys Glu Pro Glu Ser Leu Glu Ile Asn Lys
        35                  40                  45
Tyr Phe Val Val Ile Ile Tyr Ala Leu Val Phe Leu Leu Ser Leu Leu
    50                  55                  60
Gly Asn Ser Leu Val Met Leu Val Ile Leu Tyr Ser Arg Val Gly Arg
65                  70                  75                  80
Ser Val Thr Asp Val Tyr Leu Leu Asn Leu Ala Leu Ala Asp Leu Leu
                85                  90                  95
Phe Ala Leu Thr Leu Pro Ile Trp Ala Ala Ser Lys Val Asn Gly Trp
            100                 105                 110
Ile Phe Gly Thr Phe Leu Cys Lys Val Val Ser Leu Leu Lys Glu Val
        115                 120                 125
```

Asn Phe Tyr Ser Gly Ile Leu Leu Ala Cys Ile Ser Val Asp Arg
            130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu
                165                 170                 175

Ala Leu Pro Val Leu Leu Phe Arg Arg Thr Val Tyr Ser Ser Asn Val
                180                 185                 190

Ser Pro Ala Cys Tyr Glu Asp Met Gly Asn Asn Thr Ala Asn Trp Arg
                195                 200                 205

Met Leu Leu Arg Ile Leu Pro Gln Ser Phe Gly Phe Ile Val Pro Leu
            210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
275                 280                 285

Arg Asn His Ile Asp Arg Ala Leu Asp Ala Thr Glu Ile Leu Gly Ile
            290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
                340                 345                 350

Ser Gly His Thr Ser Thr Thr Leu
                355                 360

<210> SEQ ID NO 49
<211> LENGTH: 336
<212> TYPE: DNA
<213> ORGANISM: Artificial Sequence
<220> FEATURE:
<223> OTHER INFORMATION: laboratory made

<400> SEQUENCE: 49
atgtccctgc tcccacgccg cgcccctccg gtcagcatga ggctcctggc ggccgcgctg      60
ctcctgctgc tgctggcgct gtacaccgcg cgtgtggacg ggtccaaatg caagtgctcc     120
cggaagggac ccaagatccc ctacagcgac gtgaagaagc tggaaatgaa gccaaagtac     180
ccgcactgcg aggagaagat ggttatcatc accaccaaga gcgtgtccag gtaccgaggt     240
caggagcact gcctgcaccc caagctgcag agcaccaagc gcttcatcaa gtggtacaac     300
gcctggaacg agaagcgcag ggtctacgaa gaatag                               336

<210> SEQ ID NO 50
<211> LENGTH: 111
<212> TYPE: PRT
<213> ORGANISM: Artificial Sequence
<220> FEATURE:
<223> OTHER INFORMATION: laboratory made

<400> SEQUENCE: 50

Met Ser Leu Leu Pro Arg Arg Ala Pro Pro Val Ser Met Arg Leu Leu
1               5                   10                  15

Ala Ala Ala Leu Leu Leu Leu Leu Ala Leu Tyr Thr Ala Arg Val
            20                  25                  30

Asp Gly Ser Lys Cys Lys Cys Ser Arg Lys Gly Pro Lys Ile Arg Tyr
        35                  40                  45

Ser Asp Val Lys Lys Leu Glu Met Lys Pro Lys Tyr Pro His Cys Glu
50                  55                  60

Glu Lys Met Val Ile Ile Thr Thr Lys Ser Val Ser Arg Tyr Arg Gly
65                  70                  75                  80

Gln Glu His Cys Leu His Pro Lys Leu Gln Ser Thr Lys Arg Phe Ile
                85                  90                  95

Lys Trp Tyr Asn Ala Trp Asn Glu Lys Arg Arg Val Tyr Glu Glu
            100                 105                 110

<210> SEQ ID NO 51
<211> LENGTH: 1119
<212> TYPE: DNA
<213> ORGANISM: Artificial Sequence
<220> FEATURE:
<223> OTHER INFORMATION: laboratory made

<400> SEQUENCE: 51
atgatatttc catggaaatg tcagagcacc cagagggact tatggaacat cttcaagttg     60 tggggggtgga caatgctctg ttgtgatttc ctggcacatc atggaaccga ctgctggact    120
taccattatt ctgaaaaacc catgaactgg caaagggcta aagattctg ccgagacaat     180 tacacagatt tagttgccat acaaaacaag gcggaaattg agtatctgga aagactctg     240 cctttcagtc gttcttacta ctggatagga atccggaaga taggaggaat atggacgtgg    300
gtgggaacca acaaatctct tactgaagaa gcagagaact ggggagatgg tgagcccaac    360
aacaagaaga acaaggagga ctgcgtggag atctatatca agagaaacaa agatgcaggc    420
aaatggaacg atgacgcctg ccacaaacta aaggcagccc tctgttacac agcttcttgc    480
cagccctggt catgcagtgg ccatggagaa tgtgtagaaa tcatcaataa ttacacctgc    540
aactgtgatg tggggtacta tgggccccag tgtcagtttg tgattcagtg tgagcctttg    600
gaggccccag agctgggtac catggactgt actcacccct tgggaaactt cagcttcagc    660
tcacagtgtg ccttcagctg ctctgaagga caaacttaa ctgggattga agaaaccacc     720 tgtgaccat ttggaaactg gtcatctcca gaaccaacct gtcaagtgat tcagtgtgag     780
cctctatcag caccagattt ggggatcatg aactgtagcc atcccctggc cagcttcagc    840
tttacctctg catgtaccctt catctgctca gaaggaactg agttaattgg gaagaagaaa    900
accatttgtg aatcatctgg aatctggtca atcctagtc caatatgtca aaaattggac    960
aaaagtttct caatgattaa ggagggtgat tataaccccc tcttcattcc agtggcagtc   1020
atggttactg cattctctgg gttggcattt atcatttggc tggcaaggag attaaaaaaa    1080
ggcaagaaat ccaagagaag tatgaatgac ccatattaa                           1119

<210> SEQ ID NO 52
<211> LENGTH: 372
<212> TYPE: PRT
<213> ORGANISM: Artificial Sequence
<220> FEATURE:
<223> OTHER INFORMATION: laboratory made

<400> SEQUENCE: 52

Met Ile Phe Pro Trp Lys Cys Gln Ser Thr Gln Arg Asp Leu Trp Asn
1               5                   10                  15

```
Ile Phe Lys Leu Trp Gly Trp Thr Met Leu Cys Cys Asp Phe Leu Ala
             20                  25                  30

His His Gly Thr Asp Cys Trp Thr Tyr His Tyr Ser Glu Lys Pro Met
         35                  40                  45

Asn Trp Gln Arg Ala Arg Arg Phe Cys Arg Asp Asn Tyr Thr Asp Leu
    50                  55                  60

Val Ala Ile Gln Asn Lys Ala Glu Ile Glu Tyr Leu Glu Lys Thr Leu
65                  70                  75                  80

Pro Phe Ser Arg Ser Tyr Tyr Trp Ile Gly Ile Arg Lys Ile Gly Gly
                85                  90                  95

Ile Trp Thr Trp Val Gly Thr Asn Lys Ser Leu Thr Glu Glu Ala Glu
            100                 105                 110

Asn Trp Gly Asp Gly Glu Pro Asn Asn Lys Asn Lys Glu Asp Cys
            115                 120                 125

Val Glu Ile Tyr Ile Lys Arg Asn Lys Asp Ala Gly Lys Trp Asn Asp
130                 135                 140

Asp Ala Cys His Lys Leu Lys Ala Ala Leu Cys Tyr Thr Ala Ser Cys
145                 150                 155                 160

Gln Pro Trp Ser Cys Ser Gly His Gly Glu Cys Val Glu Ile Ile Asn
                165                 170                 175

Asn Tyr Thr Cys Asn Cys Asp Val Gly Tyr Tyr Gly Pro Gln Cys Gln
            180                 185                 190

Phe Val Ile Gln Cys Glu Pro Leu Glu Ala Pro Glu Leu Gly Thr Met
            195                 200                 205

Asp Cys Thr His Pro Leu Gly Asn Phe Ser Phe Ser Ser Gln Cys Ala
    210                 215                 220

Phe Ser Cys Ser Glu Gly Thr Asn Leu Thr Gly Ile Glu Glu Thr Thr
225                 230                 235                 240

Cys Gly Pro Phe Gly Asn Trp Ser Ser Pro Glu Pro Thr Cys Gln Val
                245                 250                 255

Ile Gln Cys Glu Pro Leu Ser Ala Pro Asp Leu Gly Ile Met Asn Cys
            260                 265                 270

Ser His Pro Leu Ala Ser Phe Ser Phe Thr Ser Ala Cys Thr Phe Ile
        275                 280                 285

Cys Ser Glu Gly Thr Glu Leu Ile Gly Lys Lys Lys Thr Ile Cys Glu
290                 295                 300

Ser Ser Gly Ile Trp Ser Asn Pro Ser Pro Ile Cys Gln Lys Leu Asp
305                 310                 315                 320

Lys Ser Phe Ser Met Ile Lys Glu Gly Asp Tyr Asn Pro Leu Phe Ile
                325                 330                 335

Pro Val Ala Val Met Val Thr Ala Phe Ser Gly Leu Ala Phe Ile Ile
            340                 345                 350

Trp Leu Ala Arg Arg Leu Lys Lys Gly Lys Lys Ser Lys Arg Ser Met
        355                 360                 365

Asn Asp Pro Tyr
    370

<210> SEQ ID NO 53
<211> LENGTH: 300
<212> TYPE: DNA
<213> ORGANISM: Artificial Sequence
<220> FEATURE:
<223> OTHER INFORMATION: laboratory made

<400> SEQUENCE: 53
```

```
atgacttcca agctggccgt ggctctcttg gcagccttcc tgatttctgc agctctgtgt      60
gaaggtgcag ttttgccaag gagtgctaaa gaacttagat gtcagtgcat aaagacatac    120
tccaaacctt tccacccaa atttatcaaa gaactgagag tgattgagag tggaccacac      180
tgcgccaaca cagaaattat tgtaaagctt tctgatggaa gagagctctg tctggacccc    240
aaggaaaact gggtgcagag ggttgtggag aagttttga agagggctga gaattcataa      300
```

<210> SEQ ID NO 54
<211> LENGTH: 99
<212> TYPE: PRT
<213> ORGANISM: Artificial Sequence
<220> FEATURE:
<223> OTHER INFORMATION: laboratory made

<400> SEQUENCE: 54

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 55
<211> LENGTH: 324
<212> TYPE: DNA
<213> ORGANISM: Artificial Sequence
<220> FEATURE:
<223> OTHER INFORMATION: laboratory made

<400> SEQUENCE: 55

```
atggcccgcg ctgctctctc cgccgccccc agcaatcccc ggctcctgcg agtggcactg      60
ctgctcctgc tcctggtagc cgctggccgg cgcgcagcag gagcgtccgt ggccactgaa    120
ctgcgctgcc agtgcttgca ccctgcag ggaattcacc ccaagaacat ccaaagtgtg      180
aacgtgaagt ccccggacc ccactgcgcc caaaccgaag tcatagccac actcaagaat      240
gggcggaaag cttgcctcaa tcctgcatcc cccatagtta agaaaatcat cgaaagatg      300 ctgaacagtg acaaatccaa ctga                                           324
```

<210> SEQ ID NO 56
<211> LENGTH: 107
<212> TYPE: PRT
<213> ORGANISM: Artificial Sequence
<220> FEATURE:
<223> OTHER INFORMATION: laboratory made

<400> SEQUENCE: 56

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
          35                  40                  45

Leu Gln Gly Ile His Pro Lys Asn Ile Gln Ser Val Asn Val Lys Ser
 50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105

<210> SEQ ID NO 57
<211> LENGTH: 762
<212> TYPE: DNA
<213> ORGANISM: Artificial Sequence
<220> FEATURE:
<223> OTHER INFORMATION: laboratory made

<400> SEQUENCE: 57
atgtggcccc ctgggtcagc ctcccagcca ccgccctcac ctgccgcggc cacaggtctg      60
catccagcgg ctcgccctgt gtccctgcag tgccggctca gcatgtgtcc agcgcgcagc     120
ctcctccttg tggctaccct ggtcctcctg gaccacctca gtttggccag aaacctcccc     180
gtggccactc cagacccagg aatgttccca tgccttcacc actcccaaaa cctgctgagg     240
gccgtcagca acatgctcca gaaggccaga caaactctag aattttaccc ttgcactttc     300
gaagagattg atcatgaaga tatcacaaaa gataaaacca gcacagtgga ggcctgttta     360
ccattggaat taaccaagaa tgagagttgc ctaaattcca gagagacctc tttcataact     420
aatgggagtt gcctggcctc cagaaagacc tcttttatga tggccctgtg ccttagtagt     480
atttatgaag acttgaagat gtaccaggtg gagttcaaga ccatgaatgc aaagcttctg     540
atggatccta gaggcagatc tttctagat caaaacatgc tggcagttat tgatgagctg     600
atgcaggccc tgaatttcaa cagtgagact gtgccacaaa aatcctccct tgaagaaccg     660 gattttttata aaactaaaat caagctctgc atacttcttc atgctttcag aattcgggca     720
gtgactattg atagagtgat gagctatctg aatgcttcct aa                        762

<210> SEQ ID NO 58
<211> LENGTH: 253
<212> TYPE: PRT
<213> ORGANISM: Artificial Sequence
<220> FEATURE:
<223> OTHER INFORMATION: laboratory made

<400> SEQUENCE: 58

Met Trp Pro Pro Gly Ser Ala Ser Gln Pro Pro Ser Pro Ala Ala
 1               5                  10                  15

Ala Thr Gly Leu His Pro Ala Ala Arg Pro Val Ser Leu Gln Cys Arg
                 20                  25                  30

Leu Ser Met Cys Pro Ala Arg Ser Leu Leu Val Ala Thr Leu Val
             35                  40                  45

Leu Leu Asp His Leu Ser Leu Ala Arg Asn Leu Pro Val Ala Thr Pro
 50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250

<210> SEQ ID NO 59
<211> LENGTH: 987
<212> TYPE: DNA
<213> ORGANISM: Artificial Sequence
<220> FEATURE:
<223> OTHER INFORMATION: laboratory made

<400> SEQUENCE: 59

```
atgtgtcacc agcagttggt catctcttgg tttccctgg ttttctggc atctcccctc      60
gtggccatat gggaactgaa gaaagatgtt tatgtcgtag aattggattg gtatccggat     120
gccctggag aaatggtggt cctcacctgt gacacccctg aagaagatgg tatcacctgg     180
accttggacc agagcagtga ggtcttaggc tctggcaaaa ccctgaccat ccaagtcaaa     240
gagtttggag atgctggcca gtacacctgt cacaaaggag cgaggttct aagccattcg     300
ctcctgctgc ttcacaaaaa ggaagatgga atttggtcca ctgatatttt aaaggaccag     360
aaagaaccca aaaataagac cttctctaaga tgcgaggcca gaattattc tggacgtttc     420
acctgctggt ggctgacgac aatcagtact gatttgacat tcagtgtcaa aagcagcaga     480
ggctcttctg accccaagg ggtgacgtgc ggagctgcta cactctctgc agagagagtc     540
agagggaca acaaggagta tgagtactca gtggagtgcc aggaggacag tgcctgccca     600
gctgctgagg agagtctgcc cattgaggtc atggtggatg ccgttcacaa gctcaagtat     660
gaaaactaca ccagcagctt cttcatcagg gacatcatca aacctgaccc acccaagaac     720
ttgcagctga agccattaaa gaattctcgg caggtggagg tcagctggga gtaccctgac     780
acctggagta ctccacattc ctacttctcc ctgacattct gcgttcaggt ccagggcaag     840
agcaagagag aaaagaaaga tagagtcttc acggacaaga cctcagccac ggtcatctgc     900
cgcaaaaatg ccagcattag cgtgcgggcc caggaccgct actatagctc atcttggagc     960
gaatgggcat ctgtgccctg cagttag                                        987
```

<210> SEQ ID NO 60
<211> LENGTH: 328
<212> TYPE: PRT
<213> ORGANISM: Artificial Sequence
<220> FEATURE:
<223> OTHER INFORMATION: laboratory made

<400> SEQUENCE: 60

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 61
<211> LENGTH: 536
<212> TYPE: PRT
<213> ORGANISM: Artificial Sequence
<220> FEATURE:
<223> OTHER INFORMATION: laboratory made

<400> SEQUENCE: 61

Met Gly His Gln Gln Leu Val Ile Ser Trp Phe Ser Leu Val Phe Leu

-continued

```
1               5                   10                  15
Ala Ser Pro Leu Val Ala Ile Trp Glu Leu Lys Lys Asp Val Tyr Val
                20                  25                  30
Val Glu Leu Asp Trp Tyr Pro Asp Ala Pro Gly Glu Met Val Val Leu
                35                  40                  45
Thr Cys Asp Thr Pro Glu Glu Asp Gly Ile Thr Trp Thr Leu Asp Gln
                50                  55                  60
Ser Ser Glu Val Leu Gly Ser Gly Lys Thr Leu Thr Ile Gln Val Lys
65                  70                  75                  80
Glu Phe Gly Asp Ala Gly Gln Tyr Thr Cys His Lys Gly Gly Glu Val
                85                  90                  95
Leu Ser His Ser Leu Leu Leu Leu His Lys Lys Glu Asp Gly Ile Trp
                100                 105                 110
Ser Thr Asp Ile Leu Lys Asp Gln Lys Glu Pro Lys Asn Lys Thr Phe
                115                 120                 125
Leu Arg Cys Glu Ala Lys Asn Tyr Ser Gly Arg Phe Thr Cys Trp Trp
                130                 135                 140
Leu Thr Thr Ile Ser Thr Asp Leu Thr Phe Ser Val Lys Ser Ser Arg
145                 150                 155                 160
Gly Ser Ser Asp Pro Gln Gly Val Thr Cys Gly Ala Ala Thr Leu Ser
                165                 170                 175
Ala Glu Arg Val Arg Gly Asp Asn Lys Glu Tyr Glu Tyr Ser Val Glu
                180                 185                 190
Cys Gln Glu Asp Ser Ala Cys Pro Ala Ala Glu Glu Ser Leu Pro Ile
                195                 200                 205
Glu Val Met Val Asp Ala Val His Lys Leu Lys Tyr Glu Asn Tyr Thr
                210                 215                 220
Ser Ser Phe Phe Ile Arg Asp Ile Ile Lys Pro Asp Pro Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
                260                 265                 270
Phe Cys Val Gln Val Gln Gly Lys Ser Lys Arg Glu Lys Lys Asp Arg
                275                 280                 285
Val Phe Thr Asp Lys Thr Ser Ala Thr Val Ile Cys Arg Lys Asn Ala
                290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser Val Pro Gly Val Gly Val Pro Gly
                325                 330                 335
Val Gly Ala Arg Asn Leu Pro Val Ala Thr Pro Asp Pro Gly Met Phe
                340                 345                 350
Pro Cys Leu His His Ser Gln Asn Leu Leu Arg Ala Val Ser Asn Met
                355                 360                 365
Leu Gln Lys Ala Arg Gln Thr Leu Glu Phe Tyr Pro Cys Thr Ser Glu
                370                 375                 380
Glu Ile Asp His Glu Asp Ile Thr Lys Asp Lys Thr Ser Thr Val Glu
385                 390                 395                 400
Ala Cys Leu Pro Leu Glu Leu Thr Lys Asn Glu Ser Cys Leu Asn Ser
                405                 410                 415
Arg Glu Thr Ser Phe Ile Thr Asn Gly Ser Cys Leu Ala Ser Arg Lys
                420                 425                 430
```

```
        Thr Ser Phe Met Met Ala Leu Cys Leu Ser Ser Ile Tyr Glu Asp Ser
                435                 440                 445

Lys Met Tyr Gln Val Glu Phe Lys Thr Met Asn Ala Lys Leu Leu Met
            450                 455                 460

Asp Pro Lys Arg Gln Ile Phe Leu Asp Gln Asn Met Leu Ala Val Ile
        465                 470                 475                 480

Asp Glu Leu Met Gln Ala Leu Asn Phe Asn Ser Glu Thr Val Pro Gln
                        485                 490                 495

Lys Ser Ser Leu Glu Glu Pro Asp Phe Tyr Lys Thr Lys Ile Lys Leu
                    500                 505                 510

Cys Ile Leu Leu His Ala Phe Arg Ile Arg Ala Val Thr Ile Asp Arg
                515                 520                 525

Val Met Ser Tyr Leu Asn Ala Ser
            530                 535

<210> SEQ ID NO 62
<211> LENGTH: 1611
<212> TYPE: DNA
<213> ORGANISM: Artificial Sequence
<220> FEATURE:
<223> OTHER INFORMATION: laboratory made

<400> SEQUENCE: 62
atgggtcacc agcagttggt catctcttgg tttttccctgg ttttttctggc atctcccctc      60 gtggccatat gggaactgaa gaaagatgtt tatgtcgtag aattggattg gtatccggat      120 gccccctggag aaatggtggt cctcacctgt gacaccccctg aagaagatgg tatcacctgg      180
accttggacc agagcagtga ggtcttaggc tctggcaaaa ccctgaccat ccaagtcaaa      240
gagtttggaa tgctggcca gtacacctgt cacaaaggag cgaggttct aagccattcg      300 ctcctgctgc ttcacaaaaa ggaagatgga atttggtcca ctgatatttt aaaggaccag      360
aaagaaccca aaaataagac ctttctaaga tgcgaggcca agaattattc tggacgtttc      420
acctgctggt ggctgacgac aatcagtact gatttgacat tcagtgtcaa aagcagaga      480 ggctcttctg acccccaagg ggtgacgtgc ggagctgcta cactctctgc agagagtc      540 agaggggaca caaggagta tgagtactca gtggagtgcc aggaggacag tgcctgccca      600
gctgctgagg agagtctgcc cattgaggtc atggtggatg ccgttcacaa gctcaagtat      660
gaaaactaca ccagcagctt cttcatcagg gacatcatca acctgaccc acccaagaac      720 ttgcagctga gccattaaa gaattctcgg caggtggagg tcagctggga gtaccctgac      780
acctggagta ctccacattc ctacttctcc ctgacattct gcgttcaggt ccagggcaag      840
agcaagagaa aaagaaaga tagagtcttc acggacaaga cctcagccac ggtcatctgc      900
cgcaaaaatg ccagcattag cgtgcgggcc caggaccgct actatagctc atcttggagc      960
gaatgggcat ctgtgccctg cagtgttcct ggagtagggg tacctgggt gggcgccaga     1020 aacctccccg tggccactcc agacccagga atgttcccat gccttcacca ctcccaaaac     1080
ctgctgaggg ccgtcagcaa catgctccag aaggccagac aaactctaga attttaccct     1140
tgcacttctg aagagattga tcatgaagat atcacaaaag ataaaaccag cacagtggag     1200
gcctgtttac cattggaatt aaccaagaat gagagttgcc taaattccag agagacctct     1260
ttcataacta atgggagttg cctggcctcc agaaagacct cttttatgat ggccctgtgc     1320
cttagtagta tttatgaaga ctcgaagatg taccaggtgg agttcaagac catgaatgca     1380
aagcttctga tggatcctaa gaggcagatc tttctagatc aaaacatgct ggcagttatt     1440
```

-continued

```
gatgagctga tgcaggccct gaatttcaac agtgagactg tgccacaaaa atcctccctt    1500
gaagaaccgg attttataa aactaaaatc aagctctgca tacttcttca tgctttcaga    1560
attcgggcag tgactattga tagagtgatg agctatctga atgcttccta a              1611
```

<210> SEQ ID NO 63
<211> LENGTH: 477
<212> TYPE: DNA
<213> ORGANISM: Artificial Sequence
<220> FEATURE:
<223> OTHER INFORMATION: laboratory made

<400> SEQUENCE: 63

```
atgggtcggg ggctgctcag gggcctgtgg ccgctgcaca tcgtcctgtg gacgcgtatc     60
gccagcacga tcccaccgca cgttcagaag tcggttaata cgacatgat agtcactgac    120 aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga aggaaaaaaa aaagcctggt gagactttct tcatgtgttc ctgtagctct    420
gatgagtgca atgacaacat catcttctca gaagaatata acaccagcaa tcctgac      477
```

<210> SEQ ID NO 64
<211> LENGTH: 159
<212> TYPE: PRT
<213> ORGANISM: Artificial Sequence
<220> FEATURE:
<223> OTHER INFORMATION: laboratory made

<400> SEQUENCE: 64

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp
145                 150                 155
```

<210> SEQ ID NO 65
<211> LENGTH: 933
<212> TYPE: DNA
<213> ORGANISM: Artificial Sequence
<220> FEATURE:

<223> OTHER INFORMATION: laboratory made

<400> SEQUENCE: 65

| | | | | | |
|---|---|---|---|---|---|
| atgggtcggg | ggctgctcag | gggcctgtgg | ccgctgcaca | tcgtcctgtg | gacgcgtatc | 60 |
| gccagcacga | tcccaccgca | cgttcagaag | tcggttaata | cgacatgat | agtcactgac | 120 |
| aacaacggtg | cagtcaagtt | tccacaactg | tgtaaatttt | gtgatgtgag | attttccacc | 180 |
| tgtgacaacc | agaaatcctg | catgagcaac | tgcagcatca | cctccatctg | tgagaagcca | 240 |
| caggaagtct | gtgtggctgt | atggagaaag | aatgacgaga | acataacact | agagacagtt | 300 |
| tgccatgacc | ccaagctccc | ctaccatgac | tttattctgg | aagatgctgc | ttctccaaag | 360 |
| tgcattatga | aggaaaaaaa | aaagcctggt | gagactttct | tcatgtgttc | ctgtagctct | 420 |
| gatgagtgca | atgacaacat | catcttctca | gaagaatata | acaccagcaa | tcctgacgga | 480 |
| ggtggaggaa | gtggaggagg | tggaagtggt | ggtggaggta | gtacgatccc | accgcacgtt | 540 |
| cagaagtcgg | ttaataacga | catgatagtc | actgacaaca | acggtgcagt | caagtttcca | 600 |
| caactgtgta | aattttgtga | tgtgagattt | tccacctgtg | acaaccagaa | atcctgcatg | 660 |
| agcaactgca | gcatcacctc | catctgtgag | aagccacagg | aagtctgtgt | ggctgtatgg | 720 |
| agaaagaatg | acgagaacat | aacactagag | acagtttgcc | atgaccccaa | gctcccctac | 780 |
| catgacttta | ttctggaaga | tgctgcttct | ccaaagtgca | ttatgaagga | aaaaaaaaag | 840 |
| cctggtgaga | ctttcttcat | gtgttcctgt | agctctgatg | agtgcaatga | caacatcatc | 900 |
| ttctcagaag | aatataacac | cagcaatcct | gac | | | 933 |

<210> SEQ ID NO 66
<211> LENGTH: 311
<212> TYPE: PRT
<213> ORGANISM: Artificial Sequence
<220> FEATURE:
<223> OTHER INFORMATION: laboratory made

<400> SEQUENCE: 66

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Gly
145                 150                 155                 160

Gly Gly Gly Ser Gly Gly Gly Ser Gly Gly Gly Gly Ser Thr Ile
                165                 170                 175

```
Pro Pro His Val Gln Lys Ser Val Asn Asn Asp Met Ile Val Thr Asp
        180                 185                 190

Asn Asn Gly Ala Val Lys Phe Pro Gln Leu Cys Lys Phe Cys Asp Val
            195                 200                 205

Arg Phe Ser Thr Cys Asp Asn Gln Lys Ser Cys Met Ser Asn Cys Ser
    210                 215                 220

Ile Thr Ser Ile Cys Glu Lys Pro Gln Glu Val Cys Val Ala Val Trp
225                 230                 235                 240

Arg Lys Asn Asp Glu Asn Ile Thr Leu Glu Thr Val Cys His Asp Pro
                245                 250                 255

Lys Leu Pro Tyr His Asp Phe Ile Leu Glu Asp Ala Ala Ser Pro Lys
            260                 265                 270

Cys Ile Met Lys Glu Lys Lys Lys Pro Gly Glu Thr Phe Phe Met Cys
        275                 280                 285

Ser Cys Ser Ser Asp Glu Cys Asn Asp Asn Ile Ile Phe Ser Glu Glu
    290                 295                 300

Tyr Asn Thr Ser Asn Pro Asp
305                 310

<210> SEQ ID NO 67
<211> LENGTH: 510
<212> TYPE: DNA
<213> ORGANISM: Artificial Sequence
<220> FEATURE:
<223> OTHER INFORMATION: Laboratory made

<400> SEQUENCE: 67
atgcgcatca gcaagcccca cctgcgcagc atcagcatcc agtgctacct gtgcctgctg    60
ctgaacagcc acttcctgac cgaggccggc atccacgtgt tcatcctggg ctgcttcagc   120
gccggcctgc ccaagaccga ggccaactgg gtgaacgtga tcagcgacct gaagaagatc   180
gaggacctga tccagagcat gcacatcgac gccaccctgt acaccgagag cgacgtgcac   240
cccagctgca aggtgaccgc catgaagtgc ttcctgctgg agctgcaggt gatcagcctg   300
gagagcggcg acgccagcat ccacgacacc gtggagaacc tgatcatcct ggccaacaac   360
agcctgagca gcaacggcaa cgtgaccgag agcggctgca aggagtgcga ggagctggag   420
gagaagaaca tcaaggagtt cctgcagagc ttcgtgcaca tcgtgcagat gttcatcaac   480
accagcggct ccgagaagga cgagctgtaa                                    510

<210> SEQ ID NO 68
<211> LENGTH: 1215
<212> TYPE: DNA
<213> ORGANISM: Artificial Sequence
<220> FEATURE:
<223> OTHER INFORMATION: Laboratory made

<400> SEQUENCE: 68
atggactgga tctggcggat tctgtttctc gtgggagctg ccacaggcgc tcattctgct    60
cagcctgcca acatccagat gacccagtct ccatcttctg tgtctgcatc tgtaggagac   120
agagtcacca tcacttgtcg ggcgagtcag gatattagcc gctggttagc ctggtatcag   180
cagaaaccag ggaaagcccc taaactcctg atctatgctg catccagttt gcaaagtggg   240
gtcccatcga ggttcagcgg cagtggatct gggacagatt cgctctcac tatcagcagc   300 ctgcagcctg aagattttgc aacttactat tgtcaacagg ctgacagtcg tttctcgatc   360
accttcggcc aagggacacg actggagatt aaaggcggcg gaggaagcgg aggcggagga   420
```

```
tctgggggcg gaggctctgg cggaggggga tctgaggtgc agctggtgca gtctggggga       480
ggcttggtac agcctggggg gtccctgaga ctctcctgtg cagcctctgg attcaccttc       540
agtagctata gcatgaactg ggtccgccag gctccaggga aggggctgga gtgggtttca       600
tacattagta gtagtagtag taccatacag tacgcagact ctgtgaaggg ccgattcacc       660
atctccagag acaatgccaa gaactcactg tatctgcaaa tgaacagcct gagagacgag       720
gacacggctg tgtattactg tgcgagaggg gactactact acggtatgga cgtctggggc       780
caagggacca cggtcaccgt gagctcagcg gccgcgctga gcaacagcat catgtacttc       840
agccacttcg tgcctgtgtt cctgcctgcc aagcctacaa caacaccagc cctagacct        900 ccaaccctg ccctacaat tgcctctcag cctctgtctc tgaggcccga agcttgtaga        960
cctgctgctg gcggagctgt gcacaccaga ggactggatt tcgcctgctt ttgggtgctg      1020
gtggtcgtgg gcggagtgct ggcttgttat tctctgctgg tcaccgtggc cttcatcatc      1080
ttttgggtcc gactgaagat ccaggtccga aaggccgcca tcaccagcta cgagaagtct      1140
gatggcgtgt acaccggcct gagcaccaga aaccaggaaa cctacgagac actgaagcac      1200
gagaagcccc cccag                                                       1215
```

<210> SEQ ID NO 69
<211> LENGTH: 405
<212> TYPE: PRT
<213> ORGANISM: Artificial Sequence
<220> FEATURE:
<223> OTHER INFORMATION: Laboratory made

<400> SEQUENCE: 69

```
Met Asp Trp Ile Trp Arg Ile Leu Phe Leu Val Gly Ala Ala Thr Gly
1               5                   10                  15

Ala His Ser Ala Gln Pro Ala Asn Ile Gln Met Thr Gln Ser Pro Ser
            20                  25                  30

Ser Val Ser Ala Ser Val Gly Asp Arg Val Thr Ile Thr Cys Arg Ala
        35                  40                  45

Ser Gln Asp Ile Ser Arg Trp Leu Ala Trp Tyr Gln Gln Lys Pro Gly
    50                  55                  60

Lys Ala Pro Lys Leu Leu Ile Tyr Ala Ala Ser Ser Leu Gln Ser Gly
65                  70                  75                  80

Val Pro Ser Arg Phe Ser Gly Ser Gly Ser Gly Thr Asp Phe Ala Leu
                85                  90                  95

Thr Ile Ser Ser Leu Gln Pro Glu Asp Phe Ala Thr Tyr Tyr Cys Gln
            100                 105                 110

Gln Ala Asp Ser Arg Phe Ser Ile Thr Phe Gly Gln Gly Thr Arg Leu
        115                 120                 125

Glu Ile Lys Gly Gly Gly Gly Ser Gly Gly Gly Ser Gly Gly Gly
    130                 135                 140

Gly Ser Gly Gly Gly Ser Glu Val Gln Leu Val Gln Ser Gly Gly
145                 150                 155                 160

Gly Leu Val Gln Pro Gly Gly Ser Leu Arg Leu Ser Cys Ala Ala Ser
                165                 170                 175

Gly Phe Thr Phe Ser Ser Tyr Ser Met Asn Trp Val Arg Gln Ala Pro
            180                 185                 190

Gly Lys Gly Leu Glu Trp Val Ser Tyr Ile Ser Ser Ser Ser Ser Thr
        195                 200                 205

Ile Gln Tyr Ala Asp Ser Val Lys Gly Arg Phe Thr Ile Ser Arg Asp
    210                 215                 220
```

```
Asn Ala Lys Asn Ser Leu Tyr Leu Gln Met Asn Ser Leu Arg Asp Glu
225                 230                 235                 240

Asp Thr Ala Val Tyr Tyr Cys Ala Arg Gly Asp Tyr Tyr Tyr Gly Met
                245                 250                 255

Asp Val Trp Gly Gln Gly Thr Thr Val Thr Val Ser Ser Ala Ala Ala
            260                 265                 270

Leu Ser Asn Ser Ile Met Tyr Phe Ser His Phe Val Pro Val Phe Leu
        275                 280                 285

Pro Ala Lys Pro Thr Thr Thr Pro Ala Pro Arg Pro Pro Thr Pro Ala
    290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Phe Trp Val Leu Val Val Val Gly Gly Val Leu Ala Cys Tyr Ser Leu
                340                 345                 350

Leu Val Thr Val Ala Phe Ile Ile Phe Trp Val Arg Leu Lys Ile Gln
            355                 360                 365

Val Arg Lys Ala Ala Ile Thr Ser Tyr Glu Lys Ser Asp Gly Val Tyr
    370                 375                 380

Thr Gly Leu Ser Thr Arg Asn Gln Glu Thr Tyr Glu Thr Leu Lys His
385                 390                 395                 400

Glu Lys Pro Pro Gln
                405
```